US008604167B2

(12) United States Patent
Singh et al.

(10) Patent No.: US 8,604,167 B2
(45) Date of Patent: Dec. 10, 2013

(54) CD133 EPITOPES

(71) Applicant: ImmunoCellular Therapeutics, Ltd., Woodland Hills, CA (US)

(72) Inventors: Manish Singh, Woodland Hills, CA (US); James Bender, Rancho Santa Margarita, CA (US)

(73) Assignee: ImmunoCellular Therapeutics, Ltd., Calabasas, CA (US)

( * ) Notice: Subject to any disclaimer, the term of this patent is extended or adjusted under 35 U.S.C. 154(b) by 0 days.

(21) Appl. No.: 13/737,491

(22) Filed: Jan. 9, 2013

(65) Prior Publication Data

US 2013/0115279 A1 May 9, 2013

Related U.S. Application Data

(63) Continuation of application No. 12/776,200, filed on May 7, 2010, now Pat. No. 8,383,768.

(60) Provisional application No. 61/176,302, filed on May 7, 2009.

(51) Int. Cl.
C07K 5/00 (2006.01)

(52) U.S. Cl.
USPC .......................................... 530/328; 514/19.3

(58) Field of Classification Search
None
See application file for complete search history.

(56) References Cited

U.S. PATENT DOCUMENTS

| | | |
|---|---|---|
| 4,690,915 A | 9/1987 | Rosenberg |
| 4,844,893 A | 7/1989 | Honsik et al. |
| 5,635,363 A | 6/1997 | Altman et al. |
| 5,643,786 A | 7/1997 | Cohen et al. |
| 5,788,963 A | 8/1998 | Murphy et al. |
| 5,843,633 A | 12/1998 | Yin et al. |
| 5,844,075 A | 12/1998 | Kawakami et al. |
| 5,849,589 A | 12/1998 | Tedder et al. |
| 5,851,756 A | 12/1998 | Steinman et al. |
| 5,994,126 A | 11/1999 | Steinman et al. |
| 6,010,905 A | 1/2000 | Cohen et al. |
| 6,037,135 A | 3/2000 | Kubo et al. |
| 6,300,090 B1 | 10/2001 | Steinman et al. |
| 6,455,678 B1 | 9/2002 | Yin et al. |
| 6,458,585 B1 | 10/2002 | Vachula et al. |
| 6,479,286 B1 | 11/2002 | Nelson et al. |
| 6,482,405 B1 | 11/2002 | Tahara et al. |
| 6,566,395 B1 | 5/2003 | Moran |
| 6,632,459 B2 | 10/2003 | Graus et al. |
| 6,984,522 B2 | 1/2006 | Clarke et al. |
| 7,115,360 B2 | 10/2006 | Clarke et al. |
| 7,186,409 B2 | 3/2007 | Snyder et al. |
| 7,204,982 B2 | 4/2007 | Liau |
| 7,247,480 B2 | 7/2007 | Waldmann et al. |
| 7,311,916 B2 | 12/2007 | Wild et al. |
| 7,368,531 B2 | 5/2008 | Rosen et al. |
| 7,504,490 B1 | 3/2009 | Weinstock et al. |
| 8,097,256 B2 | 1/2012 | Yu et al. |
| 2002/0034819 A1 | 3/2002 | Smith et al. |
| 2002/0045261 A1 | 4/2002 | Snyder et al. |
| 2002/0076707 A1 | 6/2002 | Mack et al. |
| 2002/0115213 A1 | 8/2002 | Snyder et al. |
| 2002/0119121 A1 | 8/2002 | Vitiello et al. |
| 2002/0182194 A1 | 12/2002 | Ju et al. |
| 2003/0064916 A1 | 4/2003 | Sherman |
| 2003/0095955 A1 | 5/2003 | Noessner et al. |
| 2003/0185823 A1 | 10/2003 | Lum et al. |
| 2003/0190682 A1 | 10/2003 | Law et al. |
| 2003/0202963 A1 | 10/2003 | Crystal et al. |
| 2003/0204052 A1 | 10/2003 | Herrmann et al. |
| 2003/0204071 A1 | 10/2003 | Moore et al. |
| 2004/0057935 A1 | 3/2004 | Yu et al. |
| 2004/0072246 A1 | 4/2004 | Martin et al. |
| 2004/0197903 A1 | 10/2004 | Pestano |
| 2004/0203143 A1 | 10/2004 | Tjoa et al. |
| 2005/0059151 A1 | 3/2005 | Bosch |
| 2005/0119198 A1 | 6/2005 | Carmeliet et al. |
| 2005/0169897 A1 | 8/2005 | Snyder et al. |
| 2006/0003323 A1 | 1/2006 | Alsobrook et al. |
| 2006/0204509 A1 | 9/2006 | Harty et al. |
| 2007/0020297 A1 | 1/2007 | Wheeler et al. |
| 2007/0098776 A1 | 5/2007 | Fikes et al. |
| 2007/0167375 A1 | 7/2007 | Okada et al. |
| 2008/0107668 A1 | 5/2008 | Philip et al. |
| 2008/0199484 A1 | 8/2008 | Yu et al. |
| 2008/0206286 A1 | 8/2008 | Yu |
| 2008/0311141 A1 | 12/2008 | Yu et al. |
| 2008/0311142 A1 | 12/2008 | Yu et al. |
| 2009/0093052 A1 | 4/2009 | Yin et al. |
| 2010/0040637 A1 | 2/2010 | Van Orden et al. |
| 2010/0135975 A1 | 6/2010 | Yu et al. |
| 2010/0310643 A1 | 12/2010 | Singh et al. |

FOREIGN PATENT DOCUMENTS

| | | |
|---|---|---|
| WO | WO 89/06692 | 7/1989 |
| WO | WO 94/26293 | 11/1994 |
| WO | WO 95/21862 | 8/1995 |

(Continued)

OTHER PUBLICATIONS

Akasaki et al., "Antitumor effect of immunizations with fusions of dendritic and glioma cells in a mouse brain tumor model," J. Immunother., 24:106-113 (2001).

Akasaki et al., "Dendritic cell-based immunotherapy for malignant gliomas," Expert Rev. Neurother., 5:497-508 (2005).

Akasaki et al., "Induction of a CD4+ T regulatory type 1 response by cyclooxygenase-2-overexpressing glioma," J. Immunol., 173:4352-59 (2004).

Akasaki et al., "T cell immunity in patients with malignant glioma: recent progress in dendritic cell-based immunotherapeutic approaches," Front. Biosci., 10:2908-21 (2005).

Al-Hajj et al., "Prospective identification of tumorigenic breast cancer cells," Proc. Natl. Acad. Sci. USA, 7:3983-88 (2003).

(Continued)

Primary Examiner — Sheela J Huff
(74) Attorney, Agent, or Firm — Fish & Richardson P.C.

(57) ABSTRACT

An immunogen includes an isolated peptide that includes the amino sequence of any one of SEQ ID NOs:1-21 with four or fewer amino acid substitutions.

20 Claims, 3 Drawing Sheets

(56) References Cited

FOREIGN PATENT DOCUMENTS

| WO | WO 96/18409 | 6/1996 |
|---|---|---|
| WO | WO 00/24778 | 5/2000 |
| WO | WO 00/38730 | 7/2000 |
| WO | WO 00/66713 | 11/2000 |
| WO | WO 01/41741 | 6/2001 |
| WO | WO 01/68148 | 9/2001 |
| WO | WO 03/010301 | 2/2003 |
| WO | WO 03/014335 | 2/2003 |
| WO | WO 03/035004 | 5/2003 |
| WO | WO 03/066097 | 8/2003 |
| WO | WO 2005/037995 | 4/2005 |
| WO | WO 2005/043155 | 5/2005 |
| WO | WO 2005/079581 | 9/2005 |
| WO | WO 2006/034334 | 3/2006 |
| WO | WO 2007/062138 | 5/2007 |
| WO | WO 2008/039874 | 4/2008 |
| WO | WO 2008/039969 | 4/2008 |
| WO | WO 2008/039974 | 4/2008 |
| WO | WO 2008/052740 | 5/2008 |
| WO | WO 2008/054716 | 5/2008 |
| WO | WO 2010/028066 | 3/2010 |
| WO | WO 2010/129895 | 11/2010 |

OTHER PUBLICATIONS

Altaner, "Glioblastoma and stem cells," Neoplasma, 55:369-374 (2008).
Beier et al., "CD133+ and CD133− glioblastoma-derived cancer stem cells show differential growth characteristics and molecular profiles," Cancer Res., 67:4010-15 (2007).
Bjerkvig et al., "Opinion: the origin of the cancer stem cell: current controversies and new insights," Nat. Rev. Cancer, 11:899-904 (2005).
Boman et al., "Cancer stem cells: a step toward the cure," J. Clin. Oncol., 26:2795-99 (2008).
Borbulevych et al., "Increased immunogenicity of an anchor-modified tumor-associated antigen is due to the enhanced stability of the peptide/MHC complex: implications for vaccine design," J. Immunol., 174:4812-20 (2005).
Borras et al., "Findings on T cell specificity revealed by synthetic combinatorial libraries," J. Immunol. Methods, 267:79-97 (2002).
Bowles, Jr. et al., "Long-term remission of malignant brain tumors after intracranial infection: a report of four cases," Neurosurgery, 44:636-642 (1999).
Brown et al., "Recognition and killing of brain tumor stem-like initiating cells by CD8+ cytolytic T cells," Cancer Res., 69:8886-93 (2009).
Candido et al., "Local administration of dendritic cells inhibits established breast tumor growth: implications for apoptosis-inducing agents," Cancer Res., 61:228-236 (2001).
Casey et al., "Heat shock protein derived from a non-autologous tumour can be used as an anti-tumour vaccine," Immunology, 110:105-111 (2003).
Castro et al., "Current and future strategies for the treatment of malignant brain tumors," Pharmacol. Ther., 98:71-108 (2003).
Chandler et al., "Long-term survival in patients with glioblastoma multiforme," Neurosurgery, 32:716-720 (1993).
Cho et al., "Recent advances of dendritic cells (DCs)-based immunotherapy for malignant gliomas," Cell Transplant., 18:977-983 (2009).
Curran et al., "Recursive partitioning analysis of prognostic factors in three radiation therapy oncology group malignant glioma trials," J. Natl. Cancer Inst., 85:704-710 (1993).
Dietz, "Engineering dendritic cell grafts for clinical trials in cellular immunotherapy of cancer: example of chronic myelogenous leukemia," Croatian Med. J., 42:428-435 (2001).
Ehtesham et al., "Intratumoral dendritic cell vaccination elicits potent tumoricidal immunity against malignant glioma in rats," J. Immunother., 26:107-116 (2003).
Ehtesham et al., "Recent progress in immunotherapy for malignant glioma: treatment strategies and results from clinical trials," Cancer Control, 11:192-207 (2004).

European Patent Office Communication for European Application No. 09812172.6, mailed May 23, 2012, 5 pages.
Falk et al., "Allele-specific motifs revealed by sequencing of self-peptides eluted from MHC molecules," Nature, 351:290-296 (1991).
Friedman et al., "Temozolomide and treatment of malignant glioma," Clin. Cancer Res., 6:2585-97 (2000).
Galli et al., "Isolation and characterization of tumorigenic, stem-like neural precursors from human glioblastoma," Cancer Res., 64:7011-21 (2004).
Garcia-Hernandez et al., "Prostate Stem Cell Antigen Vaccination Induces a Long-term Protective Immune Response against Prostate Cancer in the Absence of Autoimmunity", Cancer Res., vol. 68, No. 3, (2008), pp. 861-869.
Gatza et al., "Tumor cell lysate-pulsed dendritic cells are more effective than TCR Id protein vaccines for active immunotherapy of T cell lymphoma," J. Immunol., 169:5227-35 (2002).
Geiger et al., "Vaccination of pediatric solid tumor patients with tumor lysate-pulsed dendritic cells can expand specific T cells and mediate tumor regression," Cancer Res., 61:8513-19 (2001).
Geschwind et al., "A genetic analysis of neural progenitor differentiation," Neuron, 2:325-39 (2001).
Ghods et al., "Spheres isolated from 9L gliosarcoma rat cell line possess chemoresistant and aggressive cancer stem-like cells," Stem Cells, 7:1645-53 (2007).
Gilboa et al., "Immunotherapy of cancer with dendritic-cell-based vaccines," Cancer Immunol. Immunother., 46:82-87 (1998).
Harada et al., "Melanoma-reactive CD8+ T cells recognize a novel tumor antigen expressed in a wide variety of tumor types," J. Immunother., 24:323-333 (2001).
Harizi et al., "Prostaglandin E2 modulates dendritic cell function via EP2 and EP4 receptor subytpes," J. Leukocyte Biol., 73:756-763 (2003).
Haynes et al., "Molecular characterization of the B" regulatory subunit gene family of *Arabidopsis* protein phosphatase 2A", Euro J. Biochem., vol. 260, (1999), pp. 127-136.
Heimberger et al., "Bone marrow-derived dendritic cells pulsed with tumor homogenate induce immunity against syngeneic intracerebral glioma," J. Neuroimmunol., 103:16-25 (2000).
Hemmati et al., "Cancerous stem cells can arise from pediatric brain tumors," Proc. Natl. Acad. Sci. USA, 25:15178-83 (2003).
Hemmer et al., "Contribution of Individual Amino Acids Within MHC Molecule or Antigenic Peptide to TCR Ligand Potency," J. Immunol., 164:861-871 (2000).
Hirschmann-Jax et al., "A distinct 'side population' of cells with high drug efflux capacity in human tumor cells," Proc. Natl. Acad. Sci. USA, 39:14228-33 (2004).
Hori et al., "Neural progenitor cells lack immunogenecity and resist destruction as allografts," Stem Cells, 21:405-416 (2003).
Inoue et al., "Dendritic cells coinjected with tumor cells treated with an anticancer drug to induce tumor rejection," Surg. Today, 33:269-276 (2003).
International Preliminary Report on Patentability of International Application No. PCT/US2009/055759, mailed Mar. 17, 2011, 8 pages.
International Preliminary Report on Patentability of International Application No. PCT/US2010/034082, mailed Nov. 17, 2011, 5 pages.
International Search Report and the Written Opinion of the International Searching Authority for International Application No. PCT/US2009/055759, mailed Jun. 28, 2010, 16 pages.
International Search Report and Written Opinion of International Application No. PCT/US2010/034082, mailed Feb. 22, 2011.
Irvin et al., "T cells enhance stem-like properties and conditional malignancy in gliomas," PLoS One, 5(6):e10974 (2010).
Ji et al., "Glioma stem cell research for the development of immunotherapy," Neurosurg. Clin. N. Am., 21:159-66 (2010).
Kalinski et al., "Prostaglandin E2 induces the final maturation of IL-12 deficient CD1a+CD83+ dendritic cells: the levels of IL-12 are determined during the final dendritic cell maturation and are resistant to further modulation," J. Immunol, 161:2804-09 (1998).
Kikuchi et al., "Intratumoral injection of dendritic and irradiated glioma cells induces anti-tumor effects in a mouse brain tumor model," Cancer Immunol. Immumother., 51:424-430 (2002).

(56) References Cited

OTHER PUBLICATIONS

Kikuchi et al., "Results of a phase I clinical trial of vaccination of glioma patients with fusions of dendritic and glioma cells," Cancer Immunol. Immumother., 50:337-344 (2001).
Kimchi-Sarfaty et al., "A "Silent" Polymorphism in the MDR1 Gene Changes Substrate Specificity", Science, vol. 315, (2007), pp. 525-528 (Erratum, 1 page).
Knutson et al., "Technology evaluation: DCVax, Northwest Biotherapeutics," Curr. Opin. Mol. Ther., 4:403-407 (2002).
Kuby et al., Immunology, W. H. Freeman and Co., pp. 523-524 (1992).
La Rosa et al., "Enhanced immune activity of cytotoxic T-lymphocyte epitope analogs derived from positional scanning synthetic combinatorial libraries," Blood, 97:1776-86 (2001).
Lee et al., "Isolation of neural stem cells from the postnatal cerebellum," Nat. Neurosci., 6:723-729 (2005).
Lefranc, "Editorial: On the road to multi-modal and pluri-disciplinary treatment of glioblastomas," Acta Neurochir. (Wien), 151:109-112 (2009).
Lemmel et al., "Differential quantitative analysis of MHC ligands by mass spectrometry using stable isotope labeling," Nat. Biotechnol., 22:450-454 (2004).
Liau et al., "Treatment of intracranial gliomas with bone marrow-derived dendritic cells pulsed with tumor antigens," J. Neurosurg., 90:1115-24 (1999).
Liu et al., "AIM-2: a novel tumor antigen is expressed and presented by human glioma cells," J. Immunother., 27:220-226 (2004).
Liu et al., "Analysis of gene expression and chemoresistance of CD133+ cancer stem cells in glioblastoma," Mol. Cancer, 5:67 (2006).
Liu et al., "Cancer vaccines: a novel strategy to sensitize malignant glioma to chemotherapy," Expert Rev. Neurother., 7:1235-37 (2007).
Liu et al., "Cell-mediated immunotherapy: a new approach to the treatment of malignant glioma," Cancer Control, 10:138-147 (2003).
Liu et al., "Chemoresistance of stem-like cells isolated from glioblastoma," Proc. Amer. Assoc. Cancer Res., 47:75, abstract #320 (2006).
Liu et al., "Cytotoxic T cell targeting of TRP-2 sensitizes human malignant glioma to chemotherapy," Oncogene, 24:5226-34 (2005).
Liu et al., "HER-2, gp100, and MAGE-1 are expressed in human glioblastoma and recognized by cytotoxic T cells," Cancer Res., 64:4980-86 (2004).
Liu et al., "Molecular and functional analysis of tyrosinase-related protein (TRP)-2 as a cytotoxic T lymphocyte target in patients with malignant glioma," J. Immunother., 26:301-312 (2003).
Liu et al., "Sensitization of malignant glioma to chemotherapy through dendritic cell vaccination," Expert Rev. Vaccines, 5:233-247 (2006).
Liu et al., "Small interference RNA modulation of IL-10 in human monocyte-derived dendritic cells enhances the Th1 response," Eur. J. Immunol., 34:1680-87 (2004).
Luptrawan et al., "Dendritic cell immunotherapy for malignant gliomas," Rev. Recent Clin. Trials, 3:10-21 (2008).
Lustgarten et al., "Identification of cross-reactive peptides using combinatorial libraries circumvents tolerance against Her-2/neu-immunodominant epitope," J. Immunol., 176:1796-1805 (2006).
Maitland et al., "Prostate cancer stem cells: a new target for therapy," J. Clin. Oncol., 26:2862-70 (2008).
Mammolenti et al., "Absence of major histocompatibility complex class I on neural stem cells does not permit natural killer cell killing and prevents recognition by alloreactive cytotoxic T lymphocytes in vitro," Stem Cells, 22:1101-10 (2004).
Mehta-Damani et al., "Generation of antigen-specific CD4+ T cell lines from naive precursors," Eur. J. Immunol., 5.1206-11 (1995).
Mehta-Damani et al., "Generation of antigen-specific CD8+ CTLs from naive precursors," J. Immunol., 153:996-1003 (1994).
Melcher et al., "Dendritic cells for the immunotherapy of cancer," Clin. Oncol., 14:185-192 (2002).
Merrick et al., "Autologous versus allogeneic peptide-pulsed dendritic cells for anti-tumour vaccination: expression of allogeneic MHC supports activation of antigen specific T cells, but impairs early naive cytotoxic priming and anti-tumour therapy," Cancer Immunol Immunother., 57:897-906 (2008).
Mi et al., "Induced apoptosis supports spread of adenovirus vectors in tumors," Hum. Gene Ther., 12:1343-52 (2001).
Mizrak et al., "CD133: molecule of the moment," J. Pathol., 214:3-9 (2008).
NCBI GenBank Accession No. NM_006017 (Jul. 13, 2008).
Neuzil et al., "Tumour-initiating cells vs. cancer 'stem' cells and CD133: what's in the name?" Biochem. Biophys. Res. Commun., 355:855-859 (2007).
Ngo, J. et al., "Computational Complexity, Protein Structure Prediction and the Levinthal Paradox", (1994), The Protein Folding Problem and Tertiary Structure Prediction, Merz et al. (eds.), Birkhauser Boston: Boston, MA, pp. 433 and 492-495.
Nielsen et al., "Reliable prediction of T-cell epitopes using neural networks with novel sequence representations," Protein Sci., 12:1007-1017 (2003).
Nowak et al., "Synergy between chemotherapy and immunotherapy in the treatment of established murine solid tumors," Cancer Res., 63:4490-96 (2003).
O'Brien et al., "A human colon cancer cell capable of initiating tumour growth in immunodeficient mice," Nature, 7123:106-110 (2007).
Okada et al., "Autologous glioma cell vaccine admixed with interleukin-4 gene transfected fibroblasts in the treatment of recurrent glioblastoma: preliminary observations in a patient with a favorable response to therapy," J. Neurooncol., 64:13-20 (2003).
Okada et al., "Bone marrow-derived dendritic cells pulsed with a tumor-specific peptide elicit effective anti-tumor immunity against intracranial neoplasms," Int. J. Cancer, 78:196-201 (1998).
Okano et al., "Identification of a novel HLA-A*0201-restricted, cytotoxic T lymphocyte epitope in a human glioma-associated antigen, interleukin 13 receptor 12 chain," Clin. Cancer Res., 8:2851-55 (2002).
Osada et al., "Dendritic cells activate antitumor immunity for malignant intracranial germ cell tumor: a case report," Jpn. J. Clin. Oncol., 31:403-406 (2001).
Parkhurst et al., "Identification of a shared HLA-A*0201-restricted T-cell epitope from the melanoma antigen tyrosinase-related protein 2 (TRP2)," Cancer Res., 58:4895-4901 (1998).
Parkhurst et al., "Improved Induction of Melanoma-Reactive CTL with Peptides from the Melanoma Antigen gp100 Modified at HLA-A*0201-Binding Residues," J. Immunol., 157:2539-2548 (1996).
Parmiani et al., "Cancer immunotherapy with peptide-based vaccines: What have we achieved? Where are we going?" J. Natl. Cancer Inst., 94:805-818 (2002).
Parney et al., "Glioma immunology and immunotherapy," Neurosurgery, 46:778-792 (2000).
Pellegatta et al., "Dendritic cell vaccines for cancer stem cells," Methods Mol. Biol., 568:233-247 (2009).
Pellegatta et al., "Neurospheres enriched in cancer stem-like cells are highly effective in eliciting a dendritic cell-mediated immune response against malignant gliomas," Cancer Res., 66:10247-52 (2006).
Phuphanich et al., "Immune response correlation with progression-free survival in glioblastoma following dendritic cell immunotherapy (ICT-107)," J. Clin. Oncol., 28(15 suppl.):2097 (abstract) (2010).
Phuphanich et al., "Immune response correlation with progression-free survival in glioblastoma following dendritic cell immunotherapy (ICT-107)," poster presented at 2010 ASCO Annual Meeting, Jun. 4-8, 2010.
Pinilla et al., "Investigation of antigen-antibody interactions using a soluble, non-support-bound synthetic decapeptide library composed of four trillion ($4 \times 10^{12}$) sequences," Biochem. J., 301:847-853 (1994).
Pinilla et al., "Rapid identification of high affinity peptide ligands using positional scanning synthetic peptide combinatorial libraries," Biotechniques, 13:901-905 (1992).
Pirtskhalaishvili et al., "Cytokine-mediated protection of human dendritic cells from prostate cancer induced apoptosis is regulated by the Bcl-2 family of proteins," Br. J. Cancer, 83:506-513 (2000).

(56) References Cited

OTHER PUBLICATIONS

Pollack et al., "Exploitation of immune mechanisms in the treatment of central nervous system cancer," Semin. Pediatr. Neurol., 7:131-143 (2000).
Posnett et al., "A novel method for producing anti-peptide antibodies. Production of site-specific antibodies to the T cell antigen receptor beta-chain," J. Biol. Chem., 263:1719-25 (1988).
Reichardt et al., "Idiotype vaccination of multiple myeloma patients using monocyte-derived dendritic cells," Haematologica, 88:1139-49 (2003).
Reya et al., "Stem cells, cancer, and cancer stem cells," Nature, 6859:105-111 (2001).
Reynolds et al, "A multipotent EGF-responsive striatal embryonic progenitor cell produces neurons and astrocytes," J. Neurosci., 11:4565-74 (1992).
Reynolds et al., "Generation of neurons and astrocytes from isolated cells of the adult mammalian central nervous system," Science, 5052:1707-10 (1992).
Rissoan et al., "Reciprocal control of T helper cell and dendritic cell differentiation," Science, 283:1183-86 (1999).
Rosenberg et al , "Immunologic and therapeutic evaluation of a synthetic peptide vaccine for the treatment of patients with metastatic melanoma," Nat. Med., 4:321-327 (1998).
Rudinger, J. "Characteristics of the amino acids as components of a peptide hormone sequence", Peptide Hormones, University Park Press: Baltimore, MD, pp. 107, 1976.
Sanai et al., "Neural stem cells and the origin of gliomas," N. Eng. J. Med., 8:811-822 (2005).
Shin et al., "Antitumor effect of intratumoral administration of dendritic cell combination with vincristine chemotherapy in a murine fibrosarcoma model," Histol. Histopathol., 18:435-447 (2003).
Singh et al., "Cancer stem cells in nervous tumors," Oncogene, 23:7267-73 (2004).
Singh et al., "Identification of a cancer stem cell in human brain tumors," Cancer Res., 63:5821-28 (2003).
Singh et al., "Identification of human brain tumor initiating cells," Nature, 7015:396-401 (2004).
Singh, "ImmunoCellular Therapeutics, Ltd.," presentation at 13th Annual BIO CEO & Investor Conference, Feb. 14, 2011.
Smith et al., "CD133/prominin-1 is a potential therapeutic target for antibody-drug conjugates in hepatocellular and gastric cancers," Br. J. Cancer, 99:100-109 (2008).
Söling et al., "Dendritic cell therapy of primary brain tumors," Mol. Med., 7:659-667 (2001).
Song et al., "Strategies to improve dendritic cell-based immunotherapy against cancer," Yonsei Med. J., 45(Suppl):48-52 (2004).
Steinbrink et al., "CD4+ and CD8+ anergic T cells induced by interleukin-10—treated human dendritic cells display antigen-specific suppressor activity," Blood, 99:2468-76 (2002).
Steinman, "Some interfaces of dendritic cell biology," APMIS, 111:675-697 (2003).
Stupp et al., "Recent Developments in the Management of Malignant Glioma," American Society of Clinical Oncology Educational Book, 779-788 (2003).
Supplementary European Search Report for European Application No. 09812172.6, mailed May 4, 2012, 6 pages.
Takagi et al., "Anti-tumor effects of dendritic and tumor cell fusions are not dependent on expression of MHC class I and II by dendritic cells," Cancer Lett., 213:49-55 (2004).
Tanaka et al., "Intratumoral injection of dendritic cells after treatment of anticancer drugs induces tumor-specific antitumor effect in vivo," Int. J. Cancer, 101:265-269 (2002).
Tanaka et al., "Intratumoral injection of immature dendritic cells enhances antitumor effect of hyperthermia using magnetic nanoparticles," Int. J. Cancer, 116:624-633 (2005).
Tong et al., "Combined intratumoral injection of bone marrow-derived dendritic cells and systemic chemotherapy to treat pre-existing murine tumors," Cancer Res., 61:7530-35 (2001).
Tunici et al., "Brain tumor stem cells: new targets for clinical treatments?" Neurosurg. Focus, 4:E27 (2006).
Tunici et al., "Genetic alterations and in vivo tumorigenicity of neurospheres derived from an adult glioblastoma," Mol. Cancer, 3:25 (2004).
USPTO Final Office Action in U.S. Appl. No. 12/552,945, mailed Aug. 16, 2012, 13 pages.
USPTO Non-Final Office Action in U.S. Appl. No. 12/552,945, mailed Mar. 12, 2012, 20 pages.
Voet, D. and Voet, J., "Biochemistry", Section 6-3. Chemical Evolution, John Wiley and Sons, (1990), pp. 126-128.
Wang et al., "An effective cancer vaccine modality: lentiviral modification of dendritic cells expressing multiple cancer-specific antigens," Vaccine, 24:3477-89 (2006).
Wei et al., "Dendritic cells expressing a combined PADRE/MUC4-derived polyepitope DNA vaccine induce multiple cytotoxic T-cell responses," Cancer Biother. Radiopharm., 23:121-128 (2008).
Weigel et al., "Dendritic cells pulsed or fused with AML cellular antigen provide comparable in vivo antitumor protective responses," Exp. Hematol., 34:1403-12 (2006).
Weigmann et al., "Prominin, a novel microvilli-specific polytopic membrane protein of the apical surface of epithelial cells, is targeted to plasmalemmal protrusions of non-epithelial cells", Cell Biology, Proc. Natl. Acad. Sci. USA, vol. 94, (1997), pp. 12425-12430.
Westphal et al., "Other experimental therapies for glioma," Recent Results Cancer Res., 171:155-164 (2009).
Wheeler et al., "Cellular immunity in the treatment of brain tumors," Clin. Neurosurg., 51:132-139 (2004).
Wheeler et al., "Clinical responsiveness of glioblastoma multiforme to chemotherapy after vaccination," Clin. Cancer Res., 10:5316-26 (2004).
Wheeler et al., "Thymic CD8+ T cell production strongly influences tumor antigen recognition and age-dependent glioma mortality," J. Immunol., 171:4927-33 (2003).
Wheeler et al., "Vaccination elicits correlated immune and clinical responses in glioblastoma multiforme patients," Cancer Res., 68:5955-64 (2008).
Wu et al., "Expression of MHC I and NK ligands on human CD133+ glioma cells: possible targets of immunotherapy," J. Neurooncol., 83:121-131 (2007).
Xu et al., "Antigen-specific T-cell response from dendritic cell vaccination using cancer stem-like cell-associated antigens," Stem Cells, 27:1734-40 (2009).
Yamazaki et al., "Direct expansion of functional CD25+ CD4+ regulatory T cells by antigen-processing dendritic cells," J. Exp. Med., 198:235-247 (2003).
Yang et al., "Dendritic cells infected with a vaccinia vector carrying the human gp100 gene simultaneously present multiple specificities and elicit high-affinity T cells reactive to multiple epitopes and restricted by HLA-A2 and -A3," J Immunol., 164:4204-11 (2000).
Yang et al., "Modulation of major histocompatibility complex Class I molecules and major histocompatibility complex-bound immunogenic peptides induced by interferon-alpha and interferon-gamma treatment of human glioblastoma multiforme," J. Neurosurg., 100:310-319 (2004).
Yasuda et al., "Dendritic cell-tumor cell hybrids enhance the induction of cytotoxic T lymphocytes against murine colon cancer: a comparative analysis of antigen loading methods for the vaccination of immunotherapeutic dendritic cells," Oncol. Rep., 16:1317-24 (2006).
Yin et al., "AC133, a novel marker for human hematopoietic stem and progenitor cells," Blood, 90:5002-12 (1997).
Yin et al., "Expression and regulation of major histocompatibility complex on neural stem cells and their lineages," Stem Cells Dev., 17:53-65 (2008).
Young et al., "Dendritic cells stimulate primary human cytolytic lymphocyte responses in the absence of CD4+ helper T cells," J. Exp. Med., 171:1315-32 (1990).
Yu et al. "CD133 as a Potential Target of Anti-Cancer Stem Cell Immunotherapy: Identification of an HLA-A*02 Restricted CD133 Epitope. Abstract", Journal of Immunotherapy, Nov.-Dec. 2008, p. 928.

(56) References Cited

OTHER PUBLICATIONS

Yu et al., "AC133-2, a novel isoform of human AC133 stem cell antigen," J. Biol. Chem., 23:20711-16 (2002).
Yu et al., "Effective combination of chemotherapy and dendritic cell administration for the treatment of advanced-stage experimental breast cancer," Clin. Cancer Res., 9:285-294 (2003).
Yu et al., "Mahaley Clinical Research Award: chemosensitization of glioma through dendritic cell vaccination," Clin. Neurosurg., 53:345-351 (2006).
Yu et al., "Vaccination of malignant glioma patients with peptide-pulsed dendritic cells elicits systemic cytotoxicity and intracranial T-cell infiltration," Cancer Res., 61:842-847 (2001).
Yu et al., "Vaccination with tumor lysate-pulsed dendritic cells elicits antigen-specific, cytotoxic T-cells in patients with malignant glioma," Cancer Res., 64:4973-79 (2004).
Yuan et al., "Isolation of cancer stem cells from adult glioblastoma multiforme," Oncogene, 58:9392-9400 (2004).
Zabierowski et al., "Melanoma stem cells: the dark seed of melanoma," J. Clin. Oncol., 26:2890-94 (2008).
Zagzag et al., "Downregulation of major histocompatibility complex antigens in invading glioma cells: stealth invasion of the brain," Lab. Invest., 85:328-341 (2005).
Zeidler et al., "Tumor cell-derived prostaglandin E2 inhibits monocyte function by interfering with CCR5 and Mac-1," FASEB J., 14:661-668 (2000).
Zhang et al., "Antigenic profiling of glioma cells to generate allogeneic vaccines or dendritic cell-based therapeutics," Clin. Cancer Res., 13:566-575 (2007).
Zhu et al., "Insertion of the dibasic motif in the flanking region of a cryptic self-determinant leads to activation of the epitope-specific T cells," J. Immunol., 175:2252-60 (2005).
Zitvogel et al., "Therapy of murine tumors with tumor peptide-pulsed dendritic cells: dependence on T cells, B7 costimulation, and T helper cell-1 associated cytokines," J. Exp. Med., 183:87-97 (1996).
Zou, "Cancer initiating cells or cancer stem cells in the gastrointestinal tract and liver," J. Cell. Physiol., 217:598-604 (2008).

```
Hsap  MALVLGSLLLLGLCGNSFSGGQPSSTDAPKAWNYELPATNYETQDSHKAGPIGILFELVH  60
Ptro  MALVLGSLLLLGLCGNSFSGGQPSSTDAPKAWNYELPATNYETQDSHKAGPIGILFELVH  60
Mmul  MALVLGSLLLLGLCGNSFSGGQPSSTDAPKAWNYELPATNYETQDSHTAGPIGILFELVH  60
Rnor  MALVFSVLLLLGLCGKMASGGQPAFDNTPGALNYELPTTEYETQDTFNAGIIDPLYQMVH  60
Mmus  MALVFSALLLLGLCGKISSEGQPAFHNTPGAMNYELPTTKYETQDTFNAGIVGPLYKMVH  60
Cfam  MALLLGFLLLLELCWDTSALGPLSSTKGSDGLEFELPATNYETKDSNQAGPISVLFQIVQ  60
Btau  MALLLGFLLLLGLCEDTLSEELSSSGYRPDGLEFQLPPTSYQTSDSYDPGLAGFFFQIVR  60
      ***::. **** **  .  :      :    . . :::**.*.*:*.*:   .*  . :::*:

Hsap  IFLYVVQPRDFPEDTLRKFLQ-KAYESKIDYDKPETVILGLKIVYYEAGIILCCVLGLLF  119
Ptro  IFLYVVQPRDFPEDTLRKVIQ-KAYESKIDYDKPETVILGLKIVYYEAGIILCCVLGLLF  119
Mmul  IFLYVVQPRDFPEDTLRKVIQ-KARESKIDYDKPETLILGLKIIYYEAGIILCSVLGLLF  119
Rnor  IFLNVVQPNDFPQDLVKKLIQ-KRFDISVDTKE----------VAIYEIGVLICVILGLLF  110
Mmus  IFLSVVQPNDFPLDLIKKLIQNKKFDISVDSKEPEIIVLALKIALYEIGVLICAILGLLF  120
Cfam  VFLQVVQPHPFPEDILRKILQ-KKFDFSTDYDK----------IIYYEIGIIICAVLGLLF  110
Btau  FFVQIVQPNAFPEDILRKIIQ-KKFDLSKEYDKPENVVLTLKIIYYEIGIIICAALGLLF  119
       .*: :***. ** *  ::*.:*  *    :  . :  .:         :   ** *:::*   *****

Hsap  IILMPLVGYFFCMCRCCNKCGGEMHQRQKENGPFLRKCFAISLLVICIIISIGIFYGFVA  179
Ptro  IILMPLVGYFFCMCRCCNKCGGEMHQRQKENGPFLRKCFAISLLVICIIISIGIFYGFVA  179
Mmul  IILMPLVGYFFCMCRCCNKCGGEMHQRQKENGLFLRKCFAISLLVICIIISIGIFCGFVA  179
Rnor  IFLMPLVGFFFCMCRCCNKCGGEMHQRQKQNESCRRKCLAISLLLICLLMSLGIAFGFVA  170
Mmus  IILMPLVGCFFCMCRCCNKCGGEMHQRQKQNAPCRRKCLGLSLLVICLLMSLGIIYGFVA  180
Cfam  VILMPLVGFCFGLCRCCNKCGGEMHQRQKKNGAFLRKYFTVSLLVICIFISVGIIYGFVA  170
Btau  VILMPLVGFFFCLCRCCNKCGGEMHQRQKKSGPFLKKYFTISLLVICVFISIGIIYGFAA  179
      :.******  *  :****************:.   :*  :  :***:**:::*:**  **.*

Hsap  NHQVRTRIKRSRKLADSNFKDLRTLLNETPEQIKYILAQYNTTKDKAFTDLNSINSVLGG  239
Ptro  NHQVRTRIKRSRKLADSNFKDLRTLLNETPEQIKYILAQYNTTKDKAFTDLNSINSVLGG  239
Mmul  NHQVRTRIKRSRKLADSNFKDLRTLLNETPEQIKYILAQYNTTKDKAFSDLNSINSVLGG  239
Rnor  NQQTRTRIQRTQKLAESNYRDLRALLTEAPKQIDYILGQYNTTKNKAFSDLDSIDSVLGG  230
Mmus  NQQTRTRIKGTQKLAKSNFRDFQTLLTETPKQIDYVVEQYTNTKNKAFSDLDGIGSVLGG  240
Cfam  NHHLRTRIEKTRKLAESNLKDLRTLLIGTPAQINYVLSQYASTKEKAFSDLDNIKSLLGG  230
Btau  NHYMRTNVEETRKLSESNLNDLRTLLNVVPGQIDYILDQFTLPKEKAFDDLDNINLLVGG  239
      *:   **.:: ::**:.** .*:::**  .* **.*:: *:   .*:*** **:.*   ::**

Hsap  GILDRLRPNIIPVLDEIKSMATA-------------------------IKETKEALENMN  274
Ptro  GILDRLRPNIIPVLDEIKSMATA-------------------------IKETKEALENMN  274
Mmul  GILDRLRPNIIPVLDEIKSMATA-------------------------IKETKEALENMN  274
Rnor  RIKGQLKPKVTPVLEEIKAMATA-------------------------IRQTKDALQNMS  265
Mmus  RIKDQLKPKVTPVLEEIKAMATA-------------------------IKQTKDALQNMS  275
Cfam  GIHDQLRPKVIPVLDDIKAMAEA-------------------------IKETREALLNVN  265
Btau  SIYERLKPKVLPVLKDIKDLAEDGKGFFPPLVSPVGASVLKQAVFLTDMKTNRDTLVRMN  299
       *  :*:*:::  ***.:**  :*  :*           ::  .:::*  .:.
```

FIG. 1A

```
Hsap  STLKSLHQQSTQLSSSLTSVKTSLRSSLNDPLCLVHPSSETCNSIRLSLSQLNSNPELRQ  334
Ptro  STLKSLHQQSTQLSSSLTSVKTSLRSSLNDPLCLVRPSSEICNSIRLSLSQLNSNPELRQ  334
Mmul  STLKSLHQQSTQLSSSLTSVKTSLRASLNDPLCSVRPSSETCNSIRLSLSQLNSNPELRQ  334
Rnor  SSLKSLRDASTQLSTNLTSVRNSIENSLNSNDCASDPASKICDSLRPQLSNLGSNHNGSQ  325
Mmus  SSLKSLQDAATQLNTNLSSVRNSIENSLSSSDCTSDPASKICDSIRPSLSSLGSSLNSSQ  335
Cfam  NTLKELKMSTAQLNTSLSDVKRNLEQSLNDPMCSVPPVATTCNNIRMSLGQLDDNTNLGQ  325
Btau  TVLTDMKQSSAQLRTSLRDVKTNMEQTLMDPQCSSPAAAPTCDSIRKSLSVLDGSANFDH  359
       . *..::  ::**  :.*  .*:  .:.  :*   .  *     .  :  *:.:*  .*.  *...  :    :

Hsap  LPPVDAELDNVNNVLRTDLDGLVQQGYQSLNDIPDRVQRQTTTVVAGIKRVLNSIGSDID  394
Ptro  LPPVDAELDNVNNVLRTDLDGLVQQGYQSLNDIPDRVQRQTTTVVAGIKRVLNSIGSDID  394
Mmul  LPSVDAELDKVNNVLRTDLDGLVQQGYQSLNDIPDRVQSQTKTVVAGIKRVLNSIGSDID  394
Rnor  LPSVDRELNTVNDVDRTDLESLVKRGYMSIDEIPNMIQNQTGDVIKDVKKTLDSVSSKVK  385
Mmus  LPSVDRELNTVTEVDKTDLESLVKRGYTTIDEIPNTIQNQTVDVIKDVKNTLDSISSNIK  395
Cfam  LPSLDKQIDNINNVLQTDLSSLVQKGYKSFNDIPEMVQNQFTDIVSDVKRTLNSLGSDIE  385
Btau  LPSLDGHITQLDGLLQTDLSGLVQKANESLSNIPEEVQNQTRDFISEFKKTLNSLQSDVK  419
       **.:*  .: :   :  : :***..**::.   ::.:*** :*  **    .:  .*..*:*:  *.::

Hsap  NVTQRLPIQDILSAFSVYVNNTESYIHRNLPTLEEYDSYWWLGGLVICSLLTLIVIFYYL  454
Ptro  NVTQRLPIQDILSEFSVYVNNTESYIHRNLPTLEEYDSYWWLGGLVICSLLTLIVIFYYL  454
Mmul  NVTQHLPIQNILSEFSVYVNNTESYIHRNLPTLEEYDSYWWLGGLVICSLLTLIVIFYYL  454
Rnor  NMSQSIPVEEVLLQFSHYLNDSNRYIHESLPRVEEYDSYWWLGGLIVCFLLTLIVTFFYL  445
Mmus  DMSQSIPIEDMLLQVSHYLNNSNRYLNQELPKLEEYDSYWWLGGLIVCFLLTLIVTFFFL  455
Cfam  NMSEQIPIQDKLSDFIGYINDTETYIHRNLPTLEEYDSYRWLGGLIVCCLLTLIVVFYYL  445
Btau  NISTKIPIQKTLSNFVRYINDSEDYILQYLPTMEECDSYRWLVCLVICCLLTLILIFYLL  479
       ::: :*::. *  .  *:*::: *: . ** :** *** ** *:* ***** *: *

Hsap  GLLCGVCGYDRHATPTTRGCVSNTGGVFLMVGVGLSFLFCWILMIIVVLTFVFGANVEKL  514
Ptro  GLLCGVCGYDRHATPTTRGCVSNTGGVFLMVGVGLSFLFCWILMIIVVLTFVFGANVEKL  514
Mmul  GLLCGVCGYDRHATPTTRGCVSNTGGVFLMVGVGLSFLFCWILMIIVVLTFVFGANVEKL  514
Rnor  GLLCGVFGYDKRATPTRRGCVSNTGGIFLMAGVGFSFLFCWILMILVVLTFVVGANVEKL  505
Mmus  GLLCGVFGYDKHATPTRRGCVSNTGGIFLMAGVGFGFLFCWILMILVVLTFVVGANVEKL  515
Cfam  GLMCGTFGYDRHATPTRRGCVSNTGGIFLMVGVGISFLFCWILMTIVVLTFVIGGNMEKL  505
Btau  GLLCGTLGYDQKATPTRRGCVSNTGGLLLMVGVGLSFFFSWIIMTIVVLTFVTGGNMEKL  539
       **:**. ***::****  **********::**.***:.*:*.**:* :****** *.*:***

Hsap  ICEPYTSKELFRVLDTPYLLNEDWEYYLSGKLFNKSKMKLTFEQVYSDCKKNRGTYGTLH  574
Ptro  ICEPYTSKELFQVLDTPYLLNEDWEYYLSGKLFNKSKMKLTFEQVYSDCKKNRGTYGTLH  574
Mmul  ICEPYTSKELFRVLDTPYLLNEDWEYYLSGKLFNKSEMKLTFQQVYSDCKKNRGTYGTLH  574
Rnor  LCEPYENKKLLQVLDTPYLLNDQWQFYLSGILLKNPDINMTFEQVYRDCKRGRGVYATFQ  565
Mmus  LCEPYENKKLLQVLDTPYLLKEQWQFYLSGMLFNNPDINMTFEQVYRDCKRGRGIYAAFQ  575
Cfam  VCEPYQNRKLFQILDTPYLLNENWKYYLSGMVLDKPDINLTFEQVYSDCKENKGIYSTLK  565
Btau  VCEPYRNKKLFQVLDTPYLLNEDWKYYLSGLVFNKPDINLTFEQVYSDCKENKGLYATLK  599
       :****  .,::*,:****.**:::*::****   :::..,:::***:*** ***...:*  *.:::
```

FIG. 1B

```
Hsap  LQNSFNISEHLNINEHTGSISSELESLKVNLN-IFLLGAAGRKNLQDFAACGIDRMNYDS  633
Ptro  LQNSFNISERLNINEHTGSISSELESLKVNLN-IFLLGAAGRKNLQDFAACGIDRMNYDS  633
Mmul  LENSFDISDYLNINEHTASISSELESLKVNLN-IFLLGAAGRKSLQDFAACGIDRMNYDT  633
Rnor  LENVFNITENFNIEERLSEDIVKELEKLNVNIDSIELLDKTGRKSLEDFAQSGIDRINYSM  625
Mmus  LENVVNVSDHFNIDQISENINTELENLNVNIDSIELLDNTGRKSLEDFAHSGIDTIDYST  635
Cfam  LENTYNISEHLNIQEHARNLSNDFKNMNVNIDNIVLLDAAGRKNLMDFSSSGVDTIDYNV  625
Btau  LDHIYNVSEQLNITKHTGDINSNLENMNIRIEDIELLDKTGMKTLMDLRSSGIDDIDYAA  659
      *::   ::::  :**  .  :  .:  .:::.:::..::   *  **. :*  *.*  *:   .*:*  ::*

Hsap  YLAQTGKSPAGVNLLSFAYDLEAKANSLPPGNLRNSLKRDAQTIKTIHQQRVLPIEQSLS  693
Ptro  YLAQTGKSPAGVNLLSFAYDLEAKANSLPPGNLRNSLKRDAQTIKTIHQQRVLPIEQSLS  693
Mmul  YLAQTGKSPAGVNLLSFAYDLEAKANSLPPGNLRNSLKRDAQTIKTIHQQRVLPIEQSLS  693
Rnor  YLQEAEKPPTKVDLLTFASFLETEANQLPDGNLKQAFLMDAQNIRAIHQQHVPPVQQSLN  685
Mmus  YLKETEKSPTEVNLLTFASTLEAKANQLPEGKPKQAFLLDVQNIRAIHQHLLPPVQQSLN  695
Cfam  YLAEMGKTPTKVNLLSFADDLDTKANNLPQGSLKQSLKNNAQNLKTIHHGQVMPLEQSMS  685
Btau  YLNATERSPTRVNLISFANNLRRKANQLPSGNLKTSLKSHTDTLFNIHENQVVPLQNSMN  719
      **        :.*:  *:*::**    *    :**.** *.  :  ::    ..:.:   **.     :  *:::*:.

Hsap  TLYQSVKILQRTGNGLLERVTRILASLDFAQNFITNNTSSVIIEETKKYGRTIIGYFEHY  753
Ptro  TLYQSVKILQRTGNGLLERVTRILASLDFAQNFITNNTSSVIIEETKKYGRTIIGYFEHY  753
Mmul  TLYQSVKILQRTGNGLLERVNRILASLDFAQNFITNNISSVIIEETKKYRKTIIGYFEHY  753
Rnor  SLKQSVWALKQTSSKLPEEVKKVLASLDSAQHFLTSNLSSIVIGETKKFGRTIIGYFEHY  745
Mmus  TLRQSVWTLQQTSNKLPEKVKKILASLDSVQHFLTNNVSLIVIGETKKFGKTILGYFEHY  755
Cfam  TINQSIKELQHKSSGLRVKVANILSSLDSAQDFLQTRISSVIVKESSKYGNMIIGYFEHY  745
Btau  AMHQQMKGLQYRTSGLKVRVSTTIFFLNSTQDFLTSQLSEVVVEESKQFGNKIISYFERY  779
      ::    *.:    *:       .   *  ,.*   :   *:  .*.*:  ..  *   :::   *:.::    .  *:.***:*

Hsap  LQWIEFSISEKVASCKPVATALDTAVDVFLCSYIIDPLNLFWFGIGKATVFLLPALIFAV  813
Ptro  LQWIEFSISEKVASCKPVATALDTAVDVFLCSYIIDPLNLFWFGIGKATVFLLPALIFAV  813
Mmul  MQWIEFSISEKVASCKPVATALDTAVDVFLCSYIIDPLNLFWFGIGKATVFLLPALIFAV  813
Rnor  LQWVLYAITEKMTSCKPMITAMDSAVNGILCSYVADPLNLFWFGIGKATMLLLPAVIIAI  805
Mmus  LHWVFYAITEKMTSCKPMATAMDSAVNGILCGYVADPLNLFWFGIGKATVLLLPAVIIAI  815
Cfam  LQWVKISITEQIAACKPVATALDSAVDVFLCSYIIDPMNLFWFGIGKATIFLLPAIIFAV  805
Btau  LQWVEMAITQQFAACRPVATALDSAVNVFLCSYIVDPLNLFWFGVGKATILLLPAVIFAV  839
      ::*:     :*::::..::*:*:  **:*:**   :**.*:   **:*****:****:::****:*:*:

Hsap  KLAKYYRRMDSEDVYDDVETIPMKNMENGNNGYHKDHVYGIHNPVMTSPSQH  865
Ptro  KLAKYYRRMDSEDVYDDVETIPMKNMENGNNGYHKDHVYGIHNPVMTSPSQH  865
Mmul  KLAKYYRRMDSEDVYDDVETIPMKNPSH-----------------------  841
Rnor  KLAKYYRRMDSEDVYDDVETVPMKNLENGSNGYHKDHLYGVHNPVMTSPSRY  857
Mmus  KLAKYYRRMDSEDVYDDVETVPMKNLEIGSNGYHKDHLYGVHNPVMTSPSRY  867
Cfam  KLAKYYRRMDSEDVYDE----------------------------------  822
Btau  KLAKYFRRMYSEDVYEDEPVNKVQSKPRAQTVPRVQTVPMVQTVPMTKAL--  889
      *****:***  *****::
```

FIG. 1C

CD133 EPITOPES

CLAIM OF PRIORITY

This application is a continuation of U.S. patent application Ser. No. 12/776,200, filed on May 7, 2010, which claims priority to U.S. Patent Application Ser. No. 61/176,302, filed on May 7, 2009, the entire contents of each of which are hereby incorporated by reference.

TECHNICAL FIELD

This invention relates to methods and compositions for the treatment of cancers.

BACKGROUND

The cell surface marker CD133 (Prominin 1) is expressed by neural stem cells and has been used to select for brain cancer stem cells. In addition, CD133 positive cells are highly enriched for cancer stem cells in colon cancer, hepatocellular carcinoma, prostate cancer, multiple myeloma, and melanoma.

SUMMARY

This invention is based, in part, on the discovery of peptides of human CD133 that bind to human leukocyte antigens (HLA) and can stimulate immune responses. These peptides can be used in immunotherapy of cancers. Accordingly, compositions for cancer immunotherapy and methods for inducing immune responses in cancer patients against tumor antigens are provided herein.

In one aspect, the invention features an immunogen that includes an isolated peptide that includes the amino sequence of any of SEQ ID NOs:1-21 with four or fewer (e.g., three or fewer, two or fewer, one, or zero) amino acid substitutions (e.g., conservative substitutions). In some embodiments, the immunogen is 800 amino acid residues or fewer (e.g., 700 amino acid residues or fewer, 600 amino acid residues or fewer, 500 amino acid residues or fewer, 400 amino acid residues or fewer, 300 amino acid residues or fewer, 200 amino acid residues or fewer, 150 amino acid residues or fewer, 100 amino acid residues or fewer, 80 amino acid residues or fewer, 60 amino acid residues or fewer, 50 amino acid residues or fewer, 40 amino acid residues or fewer, 30 amino acid residues or fewer, 20 amino acid residues or fewer, 15 amino acid residues or fewer, 14 amino acid residues or fewer, 13 amino acid residues or fewer, 12 amino acid residues or fewer, 11 amino acid residues or fewer, 10 amino acid residues or fewer, or 9 amino acid residues). In some embodiments, the immunogen comprises no more than 800 consecutive amino acid residues (e.g., no more than 700 amino acid residues, no more than 600 amino acid residues, no more than 500 amino acid residues, no more than 400 amino acid residues, no more than 300 amino acid residues, no more than 200 amino acid residues, no more than 150 amino acid residues, no more than 100 amino acid residues, no more than 80 amino acid residues, no more than 60 amino acid residues, no more than 50 amino acid residues, no more than 40 amino acid residues, no more than 30 amino acid residues, no more than 20 amino acid residues, no more than 15 amino acid residues, no more than 14 amino acid residues, no more than 13 amino acid residues, no more than 12 amino acid residues, no more than 11 amino acid residues, no more than 10 amino acid residues, or no more than or 9 amino acid residues) of SEQ ID NO:26. In some embodiments, the immunogen includes a superagonist variant of any of SEQ ID NOs:1-21. In some embodiments, the immunogen does not include the sequence FLLPALIFAV (SEQ ID NO:27).

In another aspect, the invention features compositions that include an immunogen described herein linked to an immunogenic carrier, e.g., a serum albumin, tetanus toxoid, keyhole limpet hemocyanin, dextran, an agonist of a Toll-like receptor (TLR), or a recombinant virus particle.

In another aspect, the invention features polynucleotides that include a nucleic acid sequence encoding an immunogen described herein. The polynucleotides can include an expression vector, e.g., a plasmid or a nonreplicative viral vector (e.g., vaccinia, fowlpox, Venezuelan equine encephalitis virus, adeno-associated virus, and adenovirus). In some embodiments the expression vector is a virus, e.g., an RNA or DNA virus.

In another aspect, the invention features compositions (e.g., pharmaceutical or vaccine compositions) that include an immunogen or polynucleotide described herein. The compositions can further include an adjuvant (e.g., complete Freund's adjuvant, incomplete Freund's adjuvant, Montanide ISA-51, LAG-3, aluminum phosphate, aluminum hydroxide, alum, or saponin), a cytokine (e.g., Interleukin-1 (IL-1), IL-2, IL-7, IL-12, IL-13, IL-15, tumor necrosis factor (TNF), stem cell factor (SCF), or granulocyte monocyte colony stimulating factor (GM-CSF)), and/or an agonist of a Toll-like receptor (TLR) (e.g., an agonist of TLR-3, TLR-4, TLR-7, or TLR-9). The compositions can include a vehicle, e.g., a liposome (e.g., an emulsion, a foam, a micel, an insoluble monolayer, a liquid crystal, a phospholipid dispersion, or a lamellar layer), an immuno stimulating complex (ISCOM), or a slow-releasing particle.

In a further aspect, the invention features methods of immunization that include administering to a subject an immunogen, polynucleotide, or composition described herein in an amount effective to stimulate an immune response (e.g., a therapeutic or prophylactic immune response). The invention also features the use of an immunogen, polynucleotide, or composition described herein in the preparation of a medicament for stimulating an immune response. The invention also features the use of an immunogen, polynucleotide, or composition described herein to stimulate an immune response.

In another aspect, the invention features methods for treating a subject with a cancer (e.g., a cancer characterized by tumor cells expressing a class I MHC molecule). The methods include administering to the subject an immunogen, polynucleotide, or composition described herein in an amount effective to induce a CTL response to the tumor cells. The invention also features the use of an immunogen, polynucleotide, or composition described herein in the preparation of a medicament for treating a subject with a cancer (e.g., a cancer characterized by tumor cells expressing a class I MHC molecule). The invention also features the use of an immunogen, polynucleotide, or composition described herein for treating a subject with a cancer (e.g., a cancer characterized by tumor cells expressing a class I MHC molecule).

In a further aspect, the invention features methods for treating a subject with a cancer characterized by tumor cells expressing HLA-A1, HLA-A2, or HLA-A3. The methods include administering to the subject induced cytotoxic T lymphocyte (CTLs) in an amount sufficient to destroy the tumor cells through direct lysis or to effect the destruction of the tumor cells indirectly through the elaboration of cytokines, wherein the CTLs are induced by a process that includes inducing a CTL in vitro that is specific for the tumor cells by contacting a precursor CTL with an immunogen described herein under conditions that generate a CTL response to the tumor cells. The invention also features the use of an immunogen, polynucleotide, or composition described herein in the preparation of a medicament for treating a subject with a cancer characterized by tumor cells expressing HLA-A1, HLA-A2, or HLA-A3. The invention also features the use of an immunogen, polynucleotide, or composition described herein for treating a subject with a cancer characterized by tumor cells expressing HLA-A1, HLA-A2, or HLA-A3.

In another aspect, the invention features methods for treating a subject with a cancer characterized by tumor cells expressing any class I MHC molecule. The methods include administering to the subject induced cytotoxic T lymphocyte (CTLs) in an amount sufficient to destroy the tumor cells through direct lysis or to effect the destruction of the tumor cells indirectly through the elaboration of cytokines, said CTLs are induced by a process comprising inducing a CTL in vitro that is specific for said tumor cells by contacting a precursor CTL with an immunogen described herein under conditions that generate a CTL response to the tumor cells.

In a further aspect, the invention features methods for inducing a cytotoxic T lymphocyte (CTL) in vitro that is specific for a tumor cell expressing HLA-A1, HLA-A2, or HLA-A3. The methods include contacting a precursor CTL with an immunogen described herein under conditions that generate a CTL response to the tumor cells.

In another aspect, the invention features methods for inducing a cytotoxic T lymphocyte (CTL) response in vitro that is specific for a tumor cell expressing HLA-A1, HLA-A2, or HLA-A3. The methods include contacting a precursor CTL with a cell that includes a polynucleotide having a nucleic acid sequence encoding at least one polypeptide that includes an immunogen described herein.

In a further aspect, the invention features methods for treating a subject with a cancer characterized by tumor cells expressing HLA-A1, HLA-A2, or HLA-A3. The methods include administering CTLs induced by a method described herein in an amount effective to destroy the tumor cells through direct lysis or to effect the destruction of the tumor cells indirectly through the elaboration of cytokines.

The invention also features methods for treating a cancer in a patient that include administering to the patient a composition comprising antigen-presenting cells (e.g., dendritic cells), wherein the antigen presenting cells present on their surface a peptide epitope comprising the amino sequence of any of SEQ ID NOs:1-21 with four or fewer (e.g., three or fewer, two or fewer, one, or zero) amino acid substitutions (e.g., conservative substitutions) or a superagonist variant of any of SEQ ID NOs:1-21. In some embodiments, the antigen presenting cells (e.g., dendritic cells) acquire the peptide epitopes in vitro by exposure to synthetic peptides having the peptide epitopes. The invention also features the use of antigen presenting cells that present on their surface an immunogen described herein in the preparation of a medicament for treating a subject with cancer. The invention also features the use of antigen presenting cells that present on their surface an immunogen described herein for treating a subject with cancer.

In a further aspect, the invention features methods for preparing a cell vaccine for treating a cancer. The methods include: obtaining bone marrow derived mononuclear cells from a patient, culturing the mononuclear cells in vitro under conditions in which mononuclear cells become adherent to a culture vessel; selecting a subset of the mononuclear cells comprising adherent cells; culturing the adherent cells in the presence of one or more cytokines under conditions in which the cells differentiate into antigen presenting cells; and culturing the antigen presenting cells in the presence of an immunogen described herein under conditions in which the cells present the peptides on major histocompatibility class I molecules, thereby preparing a cell vaccine.

In any of the above aspects, a cancer or tumor may include one or more cells that express CD133.

In another aspect, the invention features kits that include one or more immunogens, polynucleotides, and/or compositions described herein.

A "superagonist" or "superantigen" peptide is a peptide that includes one or more mutations (e.g., one, two, or three amino acid changes, relative to a native (wild type) sequence) and that elicits an antigen-specific immunological response that is more potent than a response elicited against a peptide having a native sequence. For example, a superagonist peptide stimulates higher levels of IFN-γ release by antigen-specific T cells, as compared to T cells stimulated with the native peptide. The increase in levels of IFN-γ release stimulated by a superagonist peptide is at least higher than levels stimulated by a native peptide by a statistically significant amount. In some embodiments, a superagonist stimulates IFN-γ levels that are at least 5%, 10%, 25%, 50%, 100%, 200%, or 500% higher than elicited by the native peptide.

Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); Sambrook and Russel, Molecular Cloning: A Laboratory Manual 3rd ed., Cold Spring Harbor Laboratory Press (Cold Spring Harbor, N.Y. 2001); and Lutz et al., Handbook of Dendritic Cells Biology, Diseases and Therapies, J. Wiley & Sons (New York, N.Y. 2006), provide one skilled in the art with a general guide to many of the terms used in the present application. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the description below. Other features, objects, and advantages of the invention will be apparent from the description and from the claims.

DESCRIPTION OF THE DRAWINGS

FIGS. 1A-C depict a multiple alignment of human (Hsap, SEQ ID NO:26), chimpanzee (Ptro, SEQ ID NO:30), Rhesus macaque (Mmul, SEQ ID NO:31), rat (Rnor, SEQ ID NO:32), mouse (Mmus, SEQ ID NO:33), dog (Cfam, SEQ ID NO:34), and cattle (Btau, SEQ ID NO:35) CD133 proteins. The multiple alignment was prepared using ClustalW2 (Larkin et al., 2007, Bioinformatics, 23:2947-48). "*", residues are identical in all sequences; ":", conserved substitutions; ".", semi-conserved substitutions.

DETAILED DESCRIPTION

The present invention relates to immunogens and immunogenic compositions, and methods of use thereof, for the prevention, treatment, and/or diagnosis of cancers. Described herein are immunogens that include proteins or polypeptides whose amino acid sequences include one or more epitopic oligopeptides. In addition, the invention further relates to polynucleotides that can be used to stimulate a CTL response against cancers.

Described herein are specific oligopeptide sequences with amino acid sequences shown in SEQ ID NOs:1-21, which represent epitopic peptides (i.e., immunogenic oligopeptide sequences) of at least about 9-10 amino acids in length.

CD 133 is present in several human cancers (Mizrak et al., 2008, J. Pathol., 214:3-9; Neuzil et al., 2007, Biochem. Biophys. Res. Commun., 355:855-859), including brain cancer, colon cancer, hepatocellular carcinoma, prostate cancer, multiple myeloma, and melanoma.

An exemplary human CD133 sequence has the following amino acid sequence (SEQ ID NO:26).

```
                                              (SEQ ID NO: 26)
MALVLGSLLLLGLCGNSFSGGQPSSTDAPKAWNYELPATNYETQDSHKA

GPIGILFELVHIFLYVVQPRDFPEDTLRKFLQKAYESKIDYDKPETVIL

GLKIVYYEAGIILCCVLGLLFIILMPLVGYFFCMCRCCNKCGGEMHQRQ

KENGPFLRKCFAISLLVICIIISIGIFYGFVANHQVRTRIKRSRKLADS

NFKDLRTLLNETPEQIKYILAQYNTTKDKAFTDLNSINSVLGGGILDRL

RPNIIPVLDEIKSMATAIKETKEALENMNSTLKSLHQQSTQLSSSLTSV

KTSLRSSLNDPLCLVHPSSETCNSIRLSLSQLNSNPELRQLPPVDAELD

NVNNVLRTDLDGLVQQGYQSLNDIPDRVQRQTTTVVAGIKRVLNSIGSD

IDNVTQRLPIQDILSAFSVYVNNTESYIHRNLPTLEEYDSYWWLGGLVI

CSLLTLIVIFYYLGLLCGVCGYDRHATPTTRGCVSNTGGVFLMVGVGLS

FLFCWILMIIVVLTFVFGANVEKLICEPYTSKELFRVLDTPYLLNEDWE

YYLSGKLFNKSKMKLTFEQVYSDCKKNRGTYGTLHLQNSFNISEHLNIN

EHTGSISSELESLKVNLNIFLLGAAGRKNLQDFAACGIDRMNYDSYLAQ

TGKSPAGVNLLSFAYDLEAKANSLPPGNLRNSLKRDAQTIKTIHQQRVL

PIEQSLSTLYQSVKILQRTGNGLLERVTRILASLDFAQNFITNNTSSVI

IEETKKYGRTIIGYFEHYLQWIEFSISEKVASCKPVATALDTAVDVFLC

SYIIDPLNLFWFGIGKATVFLLPALIFAVKLAKYYRRMDSEDVYDDVET

IPMKNMENGNNGYHKDHVYGIHNPVMTSPSQH
```

The polypeptides forming the immunogens described herein have amino acid sequences that include SEQ ID NOs: 1-21 and variants thereof with four or fewer (e.g., three or fewer, two or fewer, one, or zero) amino acid substitutions (e.g., conservative substitutions).

Such polypeptides can be of any desired length so long as they have immunogenic activity in that they are able, under a given set of conditions, to elicit in vitro or in vivo the activation of cytotoxic T lymphocytes (CTLs) (i.e., a CTL response) against a presentation of CD133 in vitro or in vivo by an antigen presenting cell (APC). Exemplary polypeptides include those of 800 amino acid residues or fewer (e.g., 700 amino acid residues or fewer, 600 amino acid residues or fewer, 500 amino acid residues or fewer, 400 amino acid residues or fewer, 300 amino acid residues or fewer, 200 amino acid residues or fewer, 150 amino acid residues or fewer, 100 amino acid residues or fewer, 80 amino acid residues or fewer, 60 amino acid residues or fewer, 50 amino acid residues or fewer, 40 amino acid residues or fewer, 30 amino acid residues or fewer, 20 amino acid residues or fewer, 15 amino acid residues or fewer, 14 amino acid residues or fewer, 13 amino acid residues or fewer, 12 amino acid residues or fewer, 11 amino acid residues or fewer, 10 amino acid residues or fewer, or 9 amino acid residues). The polypeptides forming the immunogens described herein can be naturally occurring or can be synthesized chemically. The polypeptides can include at least one of SEQ ID NOs:1-21.

In some embodiments, an immunogen described herein can a variant sequence such as the counterpart of any of SEQ ID NOs:1-21 from the CD133 protein of an animal species (e.g., chimpanzee, Rhesus macaque, rat, mouse, dog, or cattle). A counterpart peptide can be identified by aligning the human and animal CD133 proteins (e.g., as shown in FIGS. 1A-C) and selecting the sequence from the animal protein that aligns with the portion of the human sequence corresponding to the peptide of interest. For example, SEQ ID NO:11 and its animal counterparts are shown in underscore in FIG. 1C. In some instances, the counterpart sequence immunogen may have more than four amino acid differences as compared to the human sequence.

Oligopeptides as disclosed herein may themselves be prepared by methods well known to those skilled in the art. See, e.g., Grant, G. A., Synthetic Peptides: A User's Guide, 1992, W.H. Freeman and Company, New York; Coligan, J. E. et al, Current Protocols in Protein Science, 1999, John Wiley & Sons, Inc., New York.

Besides the sequences of SEQ ID NOs:1-21, the proteins and polypeptides forming the immunogens described herein can also include one or more other immunogenic amino acid stretches known to be associated with cancers, and which may stimulate a CTL response whereby the immunogenic peptides associate with HLA-A1, HLA-A2, HLA-A3, HLA-A1/A11, HLA supertypes, or any class I MHC (i.e., MHC-1) molecule.

The oligopeptides and polypeptides described herein can be derived by fractionation of naturally occurring proteins by methods such as protease treatment, or they can be produced by recombinant or synthetic methodologies that are well known and clear to the skilled artisan. See, e.g., Ausubel, F. M. et al, Current Protocols in Molecular Biology, 1999, John Wiley & Sons, Inc., New York; Coligan, J. E. et al, Current Protocols in Protein Science, 1999, John Wiley & Sons, Inc., New York; Molecular Cloning: A Laboratory Manual, 1989, Cold Spring Harbor Laboratory Press, Cold Spring Harbor. The polypeptide can include a recombinant or synthetic polypeptide that includes at least one of SEQ ID NOs:1-21, which sequences can also be present in multiple copies. Thus, oligopeptides and polypeptides disclosed herein can have one, two, three, or more such immunogenic peptides within the amino acid sequence of said oligopeptides and polypeptides, and said immunogenic peptides, or epitopes, can be the same or can be different, or can have any number of such sequences, wherein some of them are identical to each other in amino acid sequence while others within the same polypeptide sequence are different from each other and said epitopic sequences can occur in any order within said immunogenic polypeptide sequence. The location of such sequences within the sequence of a polypeptide forming an immunogen described herein can affect relative immunogenic activity. In addition, immunogens described herein can include more than one protein comprising the amino acid sequences disclosed herein. Such polypeptides can be part of a single composition or can themselves be covalently or non-covalently linked to each other.

The immunogenic peptides described herein can also be linked directly to, or through a spacer or linker to: an immunogenic carrier such as serum albumin, tetanus toxoid, keyhole limpet hemocyanin, dextran, or a recombinant virus particle; a Toll-like receptor (TLR) agonist; an immunogenic peptide known to stimulate a T helper cell type immune response; a cytokine such as interferon gamma or GM-CSF; a targeting agent such as an antibody or receptor ligand; a stabilizing agent such as a lipid; or a conjugate of a plurality of epitopes to a branched lysine core structure, such as the so-called "multiple antigenic peptide" described in Posneft et al., 1988, J. Biol. Chem., 263:1719-1725; a compound such as polyethylene glycol to increase the half life of the peptide; or additional amino acids such as a leader or secretory sequence, or a sequence employed for the purification of the mature sequence. Spacers and linkers typically include relatively small, neutral molecules, such as amino acids and which are substantially uncharged under physiological conditions. Such spacers are typically selected from the group of nonpolar or neutral polar amino acids, such as glycine, alanine, serine and other similar amino acids. Such optional spacers or linkers need not include the same residues and thus can be either homo- or hetero-oligomers. When present, such linkers will commonly be of length at least one or two, commonly 3, 4, 5, 6, and possibly as much as 10 or even up to 20 residues (in the case of amino acids). In addition, such linkers need not be composed of amino acids but any oligomeric structures will do as well so long as they provide the correct spacing so as to optimize the desired level of immunogenic activity of the immunogens described herein. The immunogen can therefore take any form that is capable of eliciting a CTL response.

In addition, the immunogenic peptides described herein can be part of an immunogenic structure via attachments other than conventional peptide bonds. Thus, any manner of attaching the peptides to an immunogen described herein, such as an immunogenic polypeptide, could provide an immunogenic structure. Thus, immunogens, such as proteins, oligopeptides and polypeptides, are structures that contain the peptides disclosed, but such immunogenic peptides may not necessarily be attached thereto by the conventional means of using ordinary peptide bounds. The immunogens described herein simply contain such peptides as part of their makeup, but how such peptides are to be combined to form the final immunogen is left to the talent and imagination of the user and is in no way restricted or limited by the disclosure contained herein.

It should be appreciated that an immunogen described herein can consist only of a peptide of SEQ ID NOs:1-21 (or a variant thereof), or include a peptide of SEQ ID NOs:1-21 (or a variant thereof), or include a plurality of peptides selected from SEQ ID NOs:1-21 (or one or more variants thereof), or include a polypeptide that itself includes one or more of the epitopic peptides of SEQ ID NOs:1-21 (or one or more variants thereof). In some embodiments, an immunogen, composition, or kit described herein can further include or exclude a polypeptide, epitope, or other antigenic composition described in US 2007/0020297; US 2008/0206296; US 2008/0311142; or WO 2010/028066, all of which are incorporated by reference herein.

Modified Peptides

The peptides that are naturally processed and bound to a class I MHC molecule, and which are recognized by a tumor-specific CTL, are not necessarily the optimal peptides for stimulating a CTL response. See, for example, Parkhurst et al., 1996, J. Immunol., 157:2539-48; Rosenberg et al., 1998, Nat. Med., 4:321-32. Thus, there can be utility in modifying a peptide, such that it more readily or effectively induces a CTL response. Typically, peptides can be modified at two types of positions. The peptides can be modified at amino acid residues that are predicted to interact with the class I MHC molecule, in which case the goal is to create a peptide that has a higher affinity for the class I MHC molecule than does the original peptide. The peptides can also be modified at amino acid residues that are predicted to interact with the T cell receptor on the CTL, in which case the goal is to create a peptide that has a higher affinity for the T cell receptor than does the original peptide. Both of these types of modifications can result in a variant peptide that is related to an original peptide, but which is better able to induce a CTL response than is the original peptide. As used herein, the term "original peptide" means an oligopeptide with the amino acid sequence selected from SEQ ID NOs:1-21.

The original peptides disclosed herein can be modified by the substitution of one or more residues at different, possibly selective, sites within the peptide chain. Such substitutions can be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these often show correlation with similarities in size, charge, polarity, and hydrophobicity between the original amino acid and its replacement, and such is the basis for defining "conservative substitutions."

Conservative substitutions are defined herein as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, Ile, Val, Cys); and Group 4—large, aromatic residues (Phe, Tyr, Tip).

Less conservative substitutions might involve the replacement of one amino acid by another that has similar characteristics, but is somewhat different in size, such as replacement of an alanine by an isoleucine residue. Highly nonconservative replacements might involve substituting an acidic amino acid for one that is polar, or even for one that is basic in character, or vice versa.

Such substitutions can also involve structures other than the common L-amino acids. Thus, D-amino acids might be substituted for the L-amino acids commonly found in the antigenic peptides described herein and yet still be encompassed by the present disclosure. In addition, amino acids possessing non-standard R groups (i.e., R groups other than those found in the 20 common amino acids of natural proteins) can also be used for substitution purposes to produce immunogens and immunogenic polypeptides.

Based on cytotoxicity assays, a substituted epitopic peptide is considered substantially identical to the reference peptide if it has at least 10% of the antigenic activity of the reference peptide as defined by the ability of the substituted peptide to reconstitute the epitope recognized by a CTL in comparison to the reference peptide. Thus, when comparing the lytic activity in the linear portion of the effector:target curves with equimolar concentrations of the reference and substituted peptides, the observed percent specific killing of the target cells incubated with the substituted peptide should be equal to that of the reference peptide at an effector:target ratio that is no greater than 10-fold above the reference peptide effector: target ratio at which the comparison is being made.

Thus, the epitopes described herein can be identical to naturally occurring tumor-associated or tumor-specific epitopes or can include epitopes that differ by no more than 4 residues from the reference peptide, as long as they have substantially identical antigenic activity.

Preparation of Immunogenic Peptides and Structures

The immunogenic peptides and polypeptides described herein can be prepared synthetically, by recombinant DNA technology, or they can be isolated from natural sources such as tumor cells expressing the original protein product.

The polypeptides and oligopeptides disclosed herein can be synthesized in solution or on a solid support in accordance with conventional techniques. Various automated peptide synthesizers are commercially available and can be used in accordance with known protocols. See, for example, Grant, G. A., Synthetic Peptides: A User's Guide, 1992, W.H. Freeman and Company, New York; Coligan, J. E. et al, Current Protocols in Protein Science, 1999, John Wiley & Sons, Inc., New York. Fragments of polypeptides described herein can also be synthesized as intermediates in the synthesis of a larger polypeptide.

Recombinant DNA technology can be employed wherein a nucleotide sequence that encodes an immunogenic peptide or polypeptide of interest is inserted into an expression vector, transformed or transfected into an appropriate host cell, and cultivated under conditions suitable for expression. These procedures are well known in the art to the skilled artisan, as described in, e.g., Coligan, J. E. et al, Current Protocols in Immunology, 2006, John Wiley & Sons, Inc., New York; Ausubel, F. M. et al, Current Protocols in Molecular Biology, 1999, John Wiley & Sons, Inc., New York; Molecular Cloning: A Laboratory Manual, 1989, Cold Spring Harbor Laboratory Press, Cold Spring Harbor. Thus, recombinantly produced peptides or polypeptides can be used as the immunogens described herein.

The coding sequences for peptides of the length contemplated herein can also be synthesized on commercially available automated DNA synthesizers using protocols that are well know in the art. See for example, Grant, G. A., Synthetic Peptides: A User's Guide, 1992, W.H. Freeman and Company, New York; Coligan, J. E. et al, Current Protocols in Protein Science, 1999, John Wiley & Sons, Inc., New York. The coding sequences can also be modified such that a peptide or polypeptide will be produced that incorporates a desired amino acid substitution. The coding sequence can be provided with appropriate linkers, be ligated into suitable expression vectors that are commonly available in the art, and the resulting DNA or RNA molecule can be transformed or transfected into suitable hosts to produce the desired fusion protein. A number of such vectors and suitable host systems are available, and their selection is left to the skilled artisan. For expression of the fusion proteins, the coding sequence will be provided with operably linked start and stop codons, promoter and terminator regions, and a replication system to provide an expression vector for expression in the desired host cell. For example, promoter sequences compatible with bacterial hosts are provided in plasmids containing convenient restriction sites for insertion of the desired coding sequence. The resulting expression vectors are transformed into suitable bacterial hosts. Yeast, insect, and mammalian host cells can also be used, employing suitable vectors and control sequences.

Host cells can be genetically engineered (e.g., transduced, transformed, or transfected) with the vectors described herein which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The present invention also includes recombinant constructs comprising one or more of the sequences as broadly described above. The constructs include a vector, such as a plasmid or viral vector, into which a sequence described herein has been inserted, in a forward or reverse orientation. In a preferred aspect of this embodiment, the construct further includes regulatory sequences, including, for example, a promoter, operably linked to the sequence. Large numbers of suitable vectors and promoters are known to those of skill in the art, and are commercially available.

Host Cells

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. See, e.g., Ausubel, F. M. et al, Current Protocols in Molecular Biology, 1999, John Wiley & Sons, Inc., New York; Molecular Cloning: A Laboratory Manual, 1989, Cold Spring Harbor Laboratory Press, Cold Spring Harbor. Such cells can routinely be utilized for assaying CTL activity by having said genetically engineered, or recombinant, host cells express the immunogenic peptides described herein.

Various mammalian cell culture systems can also be employed to express recombinant protein. Examples of mammalian expression systems include the COS-7 lines of monkey kidney fibroblasts, described by Gluzman, 1981, Cell, 23:175, and other cell lines capable of expressing a compatible vector, for example, the C127, 3T3, CHO, HeLa and BHK cell lines. Mammalian expression vectors will include an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites can be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature peptides and proteins. High performance liquid chromatography (HPLC) can be employed for final purification steps.

Antigen-Presenting Cells

Antigen presenting cells that are to be used to stimulate a CTL response are typically incubated with a peptide of an optimal length, for example a nonapeptide, that allows for direct binding of the peptide to the class I MHC molecule without additional processing. Larger oligopeptides and polypeptides are generally ineffective in binding to class I MHC molecules as they are not efficiently processed into an appropriately sized peptide in the extracellular milieu. A variety of approaches are known in the art, however, that allow oligopeptides and polypeptides to be exogenously acquired by a cell, which then allows for their subsequent processing and presentation by a class I MHC molecule. Representative, but non-limiting examples of such approaches include electroporation of the molecules into the cell (Harding, 1992, Eur. J. Immunol., 22:1865-69), encapsulation of the molecules in liposomes that are fused to the cells of interest (Reddy et al., 1991, J. Immunol. Methods, 141:157-163), or osmotic shock in which the molecules are taken up via pinocytosis (Moore et al., 1988, Cell, 54:777-785). Thus, oligopeptides and polypeptides that include one or more of the peptides described herein can be provided to antigen presenting cells in such a fashion that they are delivered to the cytoplasm of the cell, and are subsequently processed to allow presentation of the peptides.

Antigen presenting cells suitable for stimulating an in vitro CTL response that is specific for one or more of the peptides described herein can also be prepared by introducing polynucleotide vectors encoding the sequences into the cells. These polynucleotides can be designed such that they express only a single peptide, multiple peptides, or even a plurality of peptides. A variety of approaches are known in the art that allow polynucleotides to be introduced and expressed in a cell, thus providing one or more peptides described herein to the class I MHC molecule binding pathway. Representative, but non-limiting examples of such approaches include the introduction of plasmid DNA through particle-mediated gene transfer or electroporation (Tuting et al., 1998, J. Immunol., 160:1139-47), or the transduction of cells with an adenovirus expressing the polynucleotide of interest (Perez-Diez et al., 1998, Cancer Res., 58:5305-09). Thus, oligonucleotides that code for one or more of the peptides described herein can be provided to antigen presenting cells in such a fashion that the peptides associate with class I MHC molecules and are presented on the surface of the antigen presenting cell, and consequently are available to stimulate a CTL response.

In certain embodiments, the methods described herein include a method for inducing a CTL response in vitro that is specific for a tumor cell expressing a molecule from A1, A2, or A3 supertypes (A11 is a member of the A3 supertype), whereby the method includes contacting a CTL precursor lymphocyte with an antigen presenting cell that has bound to an immunogen comprising one or more of the peptides disclosed herein.

In specific embodiments, the methods described herein include a method for inducing a CTL response in vitro that is specific for a tumor cell expressing a molecule from A1, A2, or A3 supertypes, whereby the method includes contacting a CTL precursor lymphocyte with an antigen presenting cell that has exogenously acquired an immunogenic oligopeptide or polypeptide that includes one or more of the peptides disclosed according to the invention.

A yet additional embodiment described herein is directed to a process for inducing a CTL response in vitro that is specific for a tumor cell expressing a molecule from A1, A2, or A3 supertypes, comprising contacting a CTL precursor lymphocyte with an antigen presenting cell that is expressing a polynucleotide coding for a polypeptide described herein, and wherein said polynucleotide is operably linked to a promoter.

A variety of techniques exist for assaying the activity of CTL. These techniques include the labeling of target cells with radionuclides such as $Na_2^{51}CrO_4$ or $^3H$-thymidine, and measuring the release or retention of the radionuclides from the target cells as an index of cell death. Such assays are well-known in the art. Alternatively, CTL are known to release a variety of cytokines when they are stimulated by an appropriate target cell, such as a tumor cell expressing the relevant class I MHC molecule and the corresponding peptide. Non-limiting examples of such cytokines include IFN-γ, TNF-α, and GM-CSF. Assays for these cytokines are well known in the art. Methodology for measuring both target cell death and cytokine release as a measure of CTL reactivity are given in Coligan, J. E. et al. (Current Protocols in Immunology, 1999, John Wiley & Sons, Inc., New York).

After expansion of the antigen-specific CTLs, the latter can then be transferred back into the patient, where they will destroy their specific target cell. The utility of such adoptive transfer is demonstrated in North et al. (199, Infect. Immun., 67:2010-12) and Riddell et al. (1992, Science, 257:238-241). In determining the number of cells to reinfuse, the skilled physician will be guided by the total number of cells available, the activity of the CTL as measured in vitro, and the condition of the patient. Typically, about $1\times10^6$ to about $1\times10^{12}$ (e.g., about $1\times10^8$ to about $1\times10^{11}$ or about $1\times10^9$ to about $1\times10^{10}$) peptide-specific CTL are infused. Methods for reinfusing T cells into a patient are well known and exemplified in U.S. Pat. No. 4,844,893 to Honski, et al., and U.S. Pat. No. 4,690,915 to Rosenberg.

The peptide-specific CTL can be purified from the stimulator cells prior to infusion into the patient. For example, monoclonal antibodies directed toward the cell surface protein CD8, present on CTL, can be used in conjunction with a variety of isolation techniques such as antibody panning, flow cytometric sorting, and magnetic bead separation to purify the peptide-specific CTL away from any remaining non-peptide specific lymphocytes or from the stimulator cells. These methods are well known in the art. It should be appreciated that generation of peptide-specific CTL in this manner obviates the need for stimulating the CTL in the presence of tumor. Thus, there is no chance of inadvertently reintroducing tumor cells into the patient.

Thus, one embodiment of the present invention relates to a process for treating a subject who has cancer characterized by tumor cells expressing complexes of a molecule from A1, A2, or A3 supertypes, for example, HLA-A1, HLA-A2, HLA-A3, or HLAA11, whereby CTLs produced in vitro according to the methods described herein are administered in an amount sufficient to destroy the tumor cells through direct lysis or to effect the destruction of the tumor cells indirectly through the elaboration of cytokines.

Another embodiment of the present invention is directed to a process for treating a subject with cancer characterized by tumor cells expressing any class I MHC molecule and an epitope of SEQ ID NOs:1-21, whereby the CTLs are produced in vitro and are specific for the epitope or original protein and are administered in an amount sufficient to destroy the tumor cells through direct lysis or to effect the destruction of the tumor cells indirectly through the elaboration of cytokines.

The ex vivo generated CTL can be used to identify and isolate the T cell receptor molecules specific for the peptide. The genes encoding the alpha and beta chains of the T cell receptor can be cloned into an expression vector system and transferred and expressed in naive T cells from peripheral blood, T cells from lymph nodes, or T lymphocyte progenitor cells from bone marrow. These T cells, which would then be expressing a peptide-specific T cell receptor, would then have anti-tumor reactivity and could be used in adoptive therapy of cancers.

Screening and Diagnostic Methods

In addition to their use for therapeutic or prophylactic purposes, the immunogenic peptides described herein are useful as screening and diagnostic agents. Thus, the immunogenic peptides described herein, together with modern techniques of gene screening, make it possible to screen patients for the presence of genes encoding such peptides on cells obtained by biopsy of tumors detected in such patients. For example, patients can be screened using nucleic acids or antibodies to detect the expression of CD133. The results of such screening can help determine the efficacy of proceeding with the regimen of treatment disclosed herein using the immunogens described herein.

Alternatively, the immunogenic peptides disclosed herein, as well as functionally similar homologs thereof, can be used to screen a sample for the presence of CTLs that specifically recognize the corresponding epitopes. The lymphocytes to be screened in this assay will normally be obtained from the peripheral blood, but lymphocytes can be obtained from other sources, including lymph nodes, spleen, tumors, and pleural fluid. The peptides described herein can then be used as a diagnostic tool to evaluate the efficacy of the immunotherapeutic treatments disclosed herein. Thus, the in vitro generation of CTL as described above would be used to determine if patients are likely to respond to the peptide in vivo. Similarly, the in vitro generation of CTL could be done with samples of lymphocytes obtained from the patient before and after treatment with the peptides. Successful generation of CTL in vivo should then be recognized by a correspondingly easier ability to generate peptide-specific CTL in vitro from lymphocytes obtained following treatment in comparison to those obtained before treatment.

The oligopeptides described herein, such as SEQ ID NOs: 1-21, can also be used to prepare multimers (e.g., dimers, tetramers, or pentamers), which can be used, e.g., in conjunction with flow cytometry, to quantitate the frequency of peptide-specific CTL that are present in a sample of lymphocytes from an individual. For example, class I MHC molecules comprising peptides of SEQ ID NOs:1-21, could be combined to form tetramers as exemplified in U.S. Pat. No. 5,635, 363. The multimers (e.g., tetramers) can be used in monitoring the frequency of CTLs in the peripheral blood, lymph nodes, or tumor mass of an individual undergoing immunotherapy with the peptides, proteins, or polynucleotides described herein, and it would be expected that successful immunization would lead to an increase in the frequency of the peptide-specific CTL. A description of peptide tetramers and methods of using them can be found in Coligan et al, Current Protocols in Immunology, 2006, John Wiley & Sons, Inc., New York.

Methods of Therapy

A vaccine can include one or more of the polypeptides or fragments thereof described herein, or a composition, or pool, of immunogenic peptides disclosed herein. Two or more polypeptides and/or fragments thereof can be used as a physical mixture or as a fusion. The fusion fragment or fusion polypeptide can be produced, for example, by recombinant techniques or by the use of appropriate linkers for fusing previously prepared polypeptides or fragments.

The immunogenic molecules described herein, including vaccine compositions, can be utilized according to the methods described herein for purposes of inhibiting, suppressing, or treating diseases causing the expression of the immunogenic peptides disclosed herein, such as where the antigen is being expressed by tumor cells. As used in accordance with the present application, the term "inhibiting" relates to a process of prophylaxis in which an animal, especially a mammal, and most especially a human, is exposed to an immunogen described herein prior to the induction or onset of the disease process. This could be done where an individual has a genetic pedigree indicating a predisposition toward occurrence of the disease condition to be prevented. For example, this might be true of an individual whose ancestors show a predisposition toward certain types of cancer. Alternatively, the immunogen could be administered to the general population as is frequently done for infectious diseases.

The term "suppression" is often used to describe a scenario wherein the disease process has already begun, but obvious symptoms of said condition have yet to be realized. Thus, the cells of an individual may have become cancerous, but no outside signs of the disease have yet been clinically recognized. The term prophylaxis is used herein to encompass both inhibition and suppression. Conversely, the term "treatment" is used herein to mean the clinical application of agents to combat an already existing condition whose clinical presentation has already been realized in a patient. This would typically occur where an individual has already been diagnosed as having a tumor.

As used herein, the term "cancer" refers to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, hepatocellular cancer, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

Additional examples of cancers that can be treated using the methods and compositions described herein include brain and nervous system cancers, including, but not limited to, gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, neurofibromas, malignant peripheral nerve sheath tumors, schwannomas, and craniopharyngiomas.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. For example, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

It is understood that the suitable dosage of an immunogen described herein will depend upon the age, sex, health, and weight of the recipient, the kind of concurrent treatment, if any, the frequency of treatment, and the nature of the effect desired. However, the most preferred dosage can be tailored to the individual subject, as determined by the researcher or clinician. The total dose required for any given treatment will commonly be determined with respect to a standard reference dose as set by a manufacturer, such as is commonly done with vaccines, such dose being administered either in a single treatment or in a series of doses, the success of which will depend on the production of a desired immunological result (i.e., successful production of a CTL-mediated response to the antigen, which response gives rise to the inhibition and/or treatment desired). Thus, the overall administration schedule must be considered in determining the success of a course of treatment and not whether a single dose, given in isolation, would or would not produce the desired immunologically therapeutic result or effect.

The therapeutically effective amount of a composition containing one or more of the immunogens described herein, is an amount sufficient to induce an effective CTL response to inhibit or arrest disease progression. Thus, this dose will depend, among other things, on the identity of the immunogens used, the nature of the disease condition, the severity of the disease condition, the extent of any need to prevent such a condition where it has not already been detected, the manner of administration dictated by the situation requiring such administration, the weight and state of health of the individual receiving such administration, and the sound judgment of the clinician or researcher. Thus, for purposes of prophylactic or therapeutic administration, effective amounts would generally lie within the range of from 1.0 µg to about 5,000 µg of peptide for a 70 kg patient, followed by boosting dosages of from about 1.0 µg to about 1,000 µg of peptide pursuant to a boosting regimen over days, weeks or months, depending on the recipient's response and as necessitated by subsequent monitoring of CTL-mediated activity within the bloodstream. Of course, such dosages are to be considered only a general guide and, in a given situation, the actual dosage can exceed such suggested dosage regimens where the clinician believes that the recipient's condition warrants a more aggressive administration schedule. The efficacy of administering additional doses, and of increasing or decreasing the interval, can be re-evaluated on a continuing basis, in view of the recipient's immunocompetence (for example, the level of CTL activity with respect to tumor-associated or tumor-specific antigens).

For such purposes, the immunogenic compositions described herein can be used against a disease condition such as cancer by administration to an individual by a variety of routes. The compositions can be administered parenterally or orally, and, if parenterally, either systemically or topically. Parenteral routes include subcutaneous, intravenous, intradermal, intramuscular, intraperitoneal, intranasal, transdermal, or buccal routes. One or more such routes can be employed. Parenteral administration can be, for example, by bolus injection or by gradual perfusion over time.

Typically, vaccines are prepared as injectables, in the form of aqueous solutions or suspensions. Vaccines in an oil base are also well known such as for inhaling. Solid forms that are dissolved or suspended prior to use can also be formulated. Pharmaceutical carriers, diluents and excipients are generally added that are compatible with the active ingredients and acceptable for pharmaceutical use. Examples of such carriers include, but are not limited to, water, saline solutions, dextrose, or glycerol. Combinations of carriers can also be used. These compositions can be sterilized by conventional, well known sterilization techniques including sterile filtration. The resulting solutions can be packaged for use as is, or the aqueous solutions can be lyophilized, the lyophilized preparation being combined with sterile water before administration. Vaccine compositions can further incorporate additional substances to stabilize pH, or to function as adjuvants, wetting agents, or emulsifying agents, which can serve to improve the effectiveness of the vaccine.

The concentration of the CTL stimulatory peptides described herein in pharmaceutical formulations are subject to wide variation, including anywhere from less than 0.01% by weight to as much as 50% or more. Factors such as volume and viscosity of the resulting composition must also be considered. The solvents, or diluents, used for such compositions include water, dimethylsulfoxide, PBS (phosphate buffered saline), or saline itself, or other possible carriers or excipients.

The immunogens described herein can also be contained in artificially created structures such as liposomes, ISCOMS, slow-releasing particles, and other vehicles which increase the immunogenicity and/or half-life of the peptides or polypeptides in serum. Liposomes include emulsions, foams, micelles, insoluble monolayers, liquid crystals, phospholipid dispersions, lamellar layers and the like. Liposomes for use in the methods and compositions described herein are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York and U.S. Pat. Nos. 4,235,871, 4,501,728, 4,837,028, and 5,019,369. Liposomes containing the peptides or polypeptides described herein can be directed to the site of lymphoid cells where the liposomes then deliver the selected immunogens directly to antigen presenting cells. Targeting can be achieved by incorporating additional molecules such as proteins or polysaccharides into the outer membranes of said structures, thus resulting in the delivery of the structures to particular areas of the body, or to particular cells within a given organ or tissue. Such targeting molecules can include a molecule that binds to receptor on antigen presenting cells. For example an antibody that binds to CD80 could be used to direct liposomes to dendritic cells.

The immunogens described herein can also be administered as solid compositions. Conventional nontoxic solid carriers including pharmaceutical grades of mannitol, lactose, starch, magnesium, cellulose, glucose, sucrose, sodium saccharin, and the like. Such solid compositions will often be administered orally, whereby a pharmaceutically acceptable nontoxic composition is formed by incorporating the peptides and polypeptides described herein with any of the carriers listed above. Generally, such compositions will contain 10-95% active ingredient, and more preferably 25-75% active ingredient.

Aerosol administration is also an alternative, requiring only that the immunogens be properly dispersed within the aerosol propellant. Typical percentages of the peptides or polypeptides described herein are 0.01%-20% by weight, e.g., 1%-10%. The use of a surfactant to properly disperse the immunogen may be required. Representative surfactants include the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1-20% by weight of the composition, e.g., 0.25-5%. Typical propellants for such administration can include esters and similar chemicals but are by no means limited to these. A carrier, such as lecithin, for intranasal delivery can also be included.

The peptides and polypeptides described herein can also be delivered with an adjuvant. Adjuvants include, but are not limited to, Toll-like receptor (TLR) agonists, Bacillus Calmette Guern (BCG), complete or incomplete Freund's adjuvant, a cytosine guanine oligodeoxynucleotide (CpG-ODN), Montanide ISA-51, Activation Gene-3 (LAG-3), aluminum phosphate, aluminum hydroxide, alum, and saponin. Adjuvant effects can also be obtained by administering one or more cytokines along with the immunogens described herein. These cytokines include, but are not limited to IL-1, IL-2, IL-7, IL-12, IL-13, IL-15, IL-18, and GM-CSF. Exemplary TLR agonists are described in Ghosh et al., 2006, Cell. Immunol., 243:48-57 and Lippincott's Illustrated Reviews: Immunology, Lippincott Williams & Wilkins; (Jul. 1, 2007), ISBN-10: 0781795435, page 17.

The peptides and polypeptides described herein can also be added to professional antigen presenting cells such as dendritic cells that have been prepared ex vivo. For example, the dendritic cells could be prepared from CD34 positive stem cells from the bone marrow, or they could be prepared from CD14 positive monocytes obtained from the peripheral blood. The dendritic cells are generated ex vivo using cytokines such as GM-CSF, IL-3, IL-4, TNF, and SCF. The cultured DC are then pulsed with peptides at various concentrations using standard methods that are well known in the art. The peptide-pulsed dendritic cells can then be administered either intravenously, subcutaneously, or intradermally, and the immunization can also include cytokines such as IL-2 or IL-12.

An antigen presenting cell (APC)-based cancer vaccine can be delivered to a patient or test animal by any suitable delivery route, which can include injection, infusion, inoculation, direct surgical delivery, or any combination thereof. In some embodiments, the cancer vaccine is administered to a human in the deltoid region or axillary region. For example, the vaccine is administered into the axillary region as an intradermal injection. In other embodiments, the vaccine is administered intravenously.

An appropriate carrier for administering APCs can be selected by one of skill in the art by routine techniques. For example, the pharmaceutical carrier can be a buffered saline solution, e.g., cell culture media, and can include DMSO for preserving cell viability.

The quantity of APCs appropriate for administration to a patient as a cancer vaccine can be based upon a variety of factors, as can the formulation of the vaccine itself. Some of these factors include the physical characteristics of the patient (e.g., age, weight, and sex), the physical characteristics of the tumor (e.g., location, size, rate of growth, and accessibility), and the extent to which other therapeutic methodologies (e.g., chemotherapy, and beam radiation therapy) are being implemented in connection with an overall treatment regimen. Notwithstanding the variety of factors one should consider in implementing the methods described herein to treat a disease condition, a mammal can be administered with from about $10^5$ to about $10^8$ APCs (e.g., $10^7$ APCs) in from about 0.05 mL to about 2 mL solution (e.g., saline) in a single administration. Additional administrations can be carried out, depending upon the above-described and other factors, such as the severity of tumor pathology. In one embodiment, from about one to about five administrations of about $10^6$ APCs is performed at two-week intervals.

APC vaccination can be accompanied by other treatments. For example, a patient receiving APC vaccination can also be receiving chemotherapy, radiation, and/or surgical therapy concurrently. Methods of treating cancer using APC vaccination in conjunction with chemotherapy are described in Wheeler et al., US Pat. Pub. No. 2007/0020297, the disclosure of which is incorporated herein by reference in its entirety. In some embodiments, a patient receiving DC vaccination has already received chemotherapy, radiation, and/or surgical treatment for the cancer. In one embodiment, a patient receiving DC vaccination is treated with a COX-2 inhibitor, as described in Yu and Akasaki, WO 2005/037995 and US 2008/0199484, the disclosure of each being incorporated herein by reference in its entirety.

The present invention is also directed to a vaccine in which an immunogen described herein is delivered or administered in the form of a polynucleotide encoding a polypeptide or fragment as disclosed herein, whereby the peptide or polypeptide or fragment is produced in vivo. The polynucleotide can be included in a suitable expression vector and combined with a pharmaceutically acceptable carrier. For example, the peptides or polypeptides could be expressed in plasmid DNA and nonreplicative viral vectors such as vaccinia, fowlpox, Venezuelan equine encephalitis virus, adenovirus, or other RNA or DNA viruses. These examples are meant to be illustrative only and should not be viewed as limiting. A wide variety of other vectors is available and are apparent to those skilled in the art from the description given herein. In this approach, a portion of the nucleotide sequence of the viral vector is engineered to express the peptides or polypeptides described herein. Vaccinia vectors and methods useful in immunization protocols are described in U.S. Pat. No. 4,722,848, the disclosure of which is incorporated herein by reference in its entirety.

Regardless of the nature of the composition given, additional therapeutic agents can also accompany the immunogens described herein. Thus, for purposes of treating tumors, compositions containing the immunogens disclosed herein can, in addition, contain other antitumor pharmaceuticals. The use of such compositions with multiple active ingredients is left to the discretion of the clinician.

A further embodiment of the present invention relates to a method for inducing a CTL response in a subject comprising administering to subjects that express HLA-A1, -A2 or -A3 supertype antigens an effective (i.e., CTL-stimulating)

amount of an immunogen described herein, e.g., an amount sufficient to induce a CTL response to tumor cells expressing at least HLA-A1, HLA-A2, or HLA-A3, as the case may be, thereby eliciting a cellular response against said tumor cells.

A still further embodiment of the present invention relates to a method for inducing a CTL response in a subject, wherein the immunogen is in the form of a polynucleotide. In one non-limiting example, the method includes administering to subjects that express HLA-A1, HLA-A2, or HLA-A3 at least one CTL epitope, wherein said epitope or epitopes are selected from a group comprising the peptides described herein, and are coded within a polynucleotide sequence that does not include the entire protein coding region, in an amount sufficient to induce a CTL response to tumor cells expressing HLA-A1, HLA-A2, or HLA-A3.

Antibodies

The immunogens described herein can be used to stimulate the production of antibodies for use in passive immunotherapy, for use as diagnostic reagents, and for use as reagents in other processes such as affinity chromatography.

The present invention also relates to antibodies that react with immunogens, such as a polypeptide comprising one or more of the epitopic peptides of SEQ ID NOs:1-21 (or a variant thereof) as described herein. Active fragments of such antibodies are also specifically contemplated. Such antibodies, and active fragments of such antibodies, for example, and Fab structure, can react with, including where it is highly selective or specific for, an immunogenic structure comprising 2, 3, 4 or more of the epitopic peptides described herein.

With the advent of methods of molecular biology and recombinant technology, it is now possible for the artisan of ordinary skill to produce antibody molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with in vitro assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the antibodies or nanobodies, or how the artisan of ordinary skill chooses to produce such antibodies or nanobodies, including recombinantly constructed or synthesized, in vitro or in vivo, by using transgenic animals, such as cows, goats and sheep, or by using cell cultures in bioreactors, or by direct chemical synthesis employing no living organisms at any stage of the process, all antibodies and nanobodies have regions capable of interacting with a structurally complementary antigenic target. The regions interacting with the target are referred to as "variable" or "V" regions and are characterized by differences in amino acid sequence from antibodies of different antigenic specificity.

The antibodies can also be wholly synthetic, wherein the polypeptide chains of the antibodies are synthesized and, possibly, optimized for binding to the polypeptides disclosed herein as being receptors. Such antibodies can be chimeric or humanized antibodies and can be fully tetrameric in structure, or can be dimeric and include only a single heavy and a single light chain. Such antibodies can also include fragments, such as Fab and F(ab')$_2$ fragments, capable of reacting with and binding to any of the polypeptides disclosed herein as being receptors.

Superagonist Peptides

The peptides and immunogens disclosed herein can also include internal mutations that render them "superantigens" or "superagonists" for T cell stimulation. Superantigen peptides can be generated by screening T cells with a positional scanning synthetic peptide combinatorial library (PS-CSL) as described in Pinilla et al., 1992, Biotechniques, 13:901-5; Borras et al., 2002, J. Immunol. Methods, 267:79-97; US 2004/0072246; and Lustgarten et al., 2006, J. Immun., 176: 1796-1805. When a native T cell epitope is known, approximately 25% of the identified variants are found to be superagonists. These can be up to 3 orders of magnitude more effective than the native ligand (Hemmer et al., 2000, J. Immunol., 164: 861-871; La Rosa et al., 2001, Blood, 97:1776-86).

Positional scanning synthetic combinatorial libraries (PS-SCLs) representing trillions of peptides of different lengths can be used as unbiased sources of peptide antigens in T cell activation assays for the identification of T cell epitopes. PS-SCL (Pinilla et al., 1992, Biotechniques, 13:901-905) are composed of systematically arranged mixtures. In the case of a single position defined PS-SCL, each compound present in a given mixture has a common individual amino acid at a given position, while the remaining positions are composed of mixtures of all 19 natural L-amino acids (cysteine omitted). The screening data of a given PS-SCL permits the identification of key residues at each position of the peptide. It is important to note, however, that the activity found for a mixture is due to the presence of specific active peptide(s) within the mixture, and not to the individual amino acids as separate entities. The combination of all amino acids defined in the most active mixtures leads to the active individual compounds.

Monitoring

The antigen-specific cellular immune responses of vaccinated subjects can be monitored by a number of different assays, such as tetramer assays, ELISPOT, and quantitative PCR. The following sections provide examples of protocols for detecting responses with these techniques. Additional methods and protocols are available. See e.g., Current Protocols in Immunology, Coligan, J. et al., Eds., (John Wiley & Sons, Inc.; New York, N.Y.).

Tetramers comprised of recombinant MHC molecules complexed with peptide can be used to identify populations of antigen-specific T cells. To detect T cells specific for antigens such as CD133, fluorochrome labeled specific peptide tetramer complexes (e.g., phycoerythrin (PE)-tHLA) containing peptides from these antigens are synthesized and provided by Beckman Coulter (San Diego, Calif.). Specific CTL clone CD8 cells are resuspended at $10^5$ cells/50 µl FACS buffer (phosphate buffer plus 1% inactivated FCS buffer). Cells are incubated with 1 µl tHLA for 30 minutes at room temperature and incubation is continued for 30 minutes at 4° C. with 10 µl anti-CD8 mAb (Becton Dickinson, San Jose, Calif.). Cells are washed twice in 2 ml cold FACS buffer before analysis by fluorescence-activated cell sorting (FACS) (Becton Dickinson).

ELISPOT assays can be used to detect cytokine secreting cells, e.g., to determine whether cells in a vaccinated patient secrete cytokine in response to antigen, thereby demonstrating whether antigen-specific responses have been elicited. ELISPOT assay kits are supplied from R & D Systems (Minneapolis, Minn.) and performed as described by the manufacturer's instructions. Responder (R) $1\times10^5$ patients' PBMC cells from before and after vaccination are plated in 96-well plates with nitrocellulose membrane inserts coated with capture Ab. Stimulator (S) cells (TAP-deficient T2 cells pulsed with antigen) are added at the R:S ratio of 1:1. After a 24-hour incubation, cells are removed by washing the plates 4 times. The detection Ab is added to each well. The plates are incubated at 4° C. overnight and the washing steps will be repeated. After a 2-hour incubation with streptavidin-AP, the plates are washed. Aliquots (100 µl) of BCIP/NBT chromogen are added to each well to develop the spots. The reaction is stopped after 60 min by washing with water. The spots are scanned and counted with computer-assisted image analysis (Cellular Technology Ltd, Cleveland, Ohio). When experimental values are significantly different from the mean number of spots against non-pulsed T2 cells (background values), as determined by a two-tailed Wilcoxon rank sum test, the background values are subtracted from the experimental values.

Quantitative PCR is another means for evaluating immune responses. To examine IFN-γ production in patients by quantitative PCR, cryopreserved PBMCs from patients' pre-vaccination and post-vaccinations samples and autologous dendritic cells are thawed in RPMI DC culture medium with 10% patient serum, washed and counted. PBMC are plated at $3 \times 10^6$ PBMCs in 2 ml of medium in 24-well plate; dendritic cells are plated at $1 \times 10^6$/ml and are pulsed 24 hour with 10 µg/ml tumor peptide in 2 ml in each well in 24 well plate. Dendritic cells are collected, washed, and counted, and diluted to $1 \times 10^6$/ml, and $3 \times 10^5$ (i.e., 300 µl solution) added to wells with PBMC (DC: PBMC=1:10). 2.3 µl IL-2 (300 IU/mL) is added every 3-4 days, and the cells are harvested between day 10 and day 13 after initiation of the culture. The harvested cells are then stimulated with tumor cells or autologous PBMC pulsed with 10 µg/ml tumor peptide for 4 hours at 37° C. On days 11-13, cultures are harvested, washed twice, then divided into four different wells, two wells using for control (without target); and another two wells CTL co-cultured with tumor cells (1:1) if tumor cells are available. If tumor cells are not available, 10 µg/ml tumor lysate is added to CTL. After 4 hours of stimulation, the cells are collected, RNA extracted, and IFN-γ and CD8 mRNA expression evaluated with a thermocycler/fluorescence camera system. PCR amplification efficiency follows natural log progression, with linear regression analyses demonstrating correlation coefficients in excess of 0.99. Based on empirical analysis, a one-cycle difference is interpreted to be a two-fold difference in mRNA quantity, and CD8-normalized IFN-γ quantities are determined. An increase of >1.5-fold in post-vaccine relative to pre-vaccine IFN-γ is the established standard for positive type I vaccine responsiveness.

Ex Vivo Methods

The following protocol can be used to produce antigen-presenting cells and/or antigen-specific CTL in vitro from patient-derived PBMC. To generate dendritic cells, the plastic adherent cells from PBMCs are cultured in AIM-V medium supplemented with recombinant human GM-CSF and recombinant human IL-4 at 37° C. in a humidified $CO_2$ (5%) incubator. Six days later, the immature dendritic cells in the cultures are stimulated with recombinant human TNF-α for maturation. Mature dendritic cells are then harvested on day 8, resuspended in PBS at $1 \times 10^6$ per mL with peptide (2 µg/mL), and incubated for 2 hours at 37° C.

Autologous CD8+ T cells are enriched from PBMCs using magnetic microbeads (Miltenyi Biotech, Auburn, Calif.). CD8+ T cells ($2 \times 10^6$ per well) are co-cultured with $2 \times 10^5$ per well peptide-pulsed dendritic cells in 2 mL/well of AIM-V medium supplemented with 5% human AB serum and 10 units/mL rhIL-7 (Cell Sciences) in each well of 24-well tissue culture plates. About 20 U/ml of IL-2 is added 24 h later at regular intervals, 2 days after each restimulation. On day 7, lymphocytes are restimulated with autologous dendritic cells pulsed with peptide in AIM-V medium supplemented with 5% human AB serum, rhIL-2, and rhIL-7 (10 units/mL each). About 20 U/ml of IL-2 is added 24 h later at regular intervals, 2 days after each restimulation. On the seventh day, after the three rounds of restimulation, cells are harvested and tested the activity of CTL. The stimulated CD8+ cultured cells (CTL) are co-cultured with T2 cells (a human TAP-deficient cell line) pulsed with 2 µg/ml CD133 peptides. After 24 hours incubation, IFN-γ in the medium is measured by ELISA assay.

Animal Models

Vaccination (e.g., DC vaccination) can be evaluated in animal models. Suitable models for cancers include injection models, in which cells of a tumor cell line are injected into the animal, and genetic models, in which tumors arise during development. In some cases, a transgenic animal (e.g., a mouse) that expresses an HLA (e.g., HLA-A2) can be used. See, e.g., Choi et al., 2002, J. Immunol. Methods, 268:35-41.

To evaluate dendritic cell vaccination in an animal model, functional dendritic cells are isolated from bone marrow derived cells of the animal and differentiated in vitro in the presence of cytokines, as detailed above. Mature dendritic cells are pulsed with tumor antigens (e.g., tumor antigens derived from the tumor cell line that will be implanted into the animal or synthetic peptides corresponding to epitopes of those antigens). Animals are implanted with cells of the tumor cell line. After implantation, animals are vaccinated with antigen-pulsed dendritic cells one or more times. Survival and immune responsiveness is measured.

Kits

The present invention is also directed to kits to treat cancers. The kits are useful for practicing the methods described herein for treating cancer with a vaccine comprising an antigen or APCs loaded with an antigen as described herein. The kit is an assemblage of materials or components, including at least one of the compositions described herein. Thus, in some embodiments, the kit includes a set of peptides for use in vaccination or preparing cells for vaccination. The kit can also include agents for preparing cells (e.g., cytokines for inducing differentiation of DC in vitro). The invention also provides kits containing a composition including a vaccine comprising dendritic cells (e.g., cryopreserved dendritic cells) loaded with the antigens as described herein.

The exact nature of the components configured in the kit depends on its intended purpose. For example, some embodiments are configured for the purpose of treating brain cancer, colon cancer, hepatocellular carcinoma, prostate cancer, multiple myeloma, and melanoma. In one embodiment the brain cancer is a glioma. In another embodiment, the brain cancer is glioblastoma multiforme (GBM). In another embodiment, the brain cancer is an astrocytoma. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use can be included in the kit. "Instructions for use" typically include a tangible expression describing the technique to be employed in using the components of the kit to effect a desired outcome, such as to treat cancer. For example, the instructions can include instructions to administer a vaccine (e.g., comprising dendritic cells loaded with the antigens described herein) to the patient. Instructions for use can also include instructions for repeated administrations of the vaccine; for example, administering the three doses of the vaccine in two week intervals.

Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as compositions described herein and the like. The packaging material is constructed by well known methods, preferably to provide a sterile, contaminant-free environment. The packaging materials employed in the kit are those customarily utilized in cancer treatments or in vaccinations. As used herein, the term "package" refers to a suitable solid matrix or material such as glass, plastic, paper, foil, and the like, capable of holding the individual kit components. Thus, for example, a package can be a glass vial used to contain suitable quantities of a composition containing a vaccine, e.g., a vaccine comprising an immunogen or dendritic cells loaded with the antigens as described herein. The packaging material generally has an external label which indicates the contents and/or purpose of the kit and/or its components.

EXAMPLES

The following Examples are illustrative and not limiting.

Example 1

Prediction and Synthesis of CD133 Epitopes

Epitopes of CD133 were predicted using the Immune Epitope free public database for predicting Class 1 MHC-peptide binding to HLA-A*0101, -A*0201 and -A*0301 using the artificial neural network (ANN) method (Nielsen et al., 2003, Protein Sci., 12:1007-17). The algorithm used be found on the World Wide Web at tools.immuneepitope.org/analyze/html/mhc_binding.html. Peptides were selected based on predicted $IC_{50}$ for HLA-A*0101 ($IC50 \leq 5000$ nM), HLA-A*0201 ($IC50 \leq 500$ nM), and HLA-A*0301 ($IC50 \leq 500$ nM). Eighty-four candidate nine-amino acid sequences of CD133 were synthesized (ProImmune Ltd., Oxford, UK) to determine whether the peptides bound to the MHCs HLA-A*0101, HLA-A*0201, and HLA-A*0301. The information generated from the Immune Epitope Database is only a general guideline. These scores are based solely on algorithms and cannot confirm whether the sequences are true or optimal T cell epitopes. Additionally, there may be some sequences that do not score well on algorithms that will be good T cell epitopes.

Example 2

Identification of HLA-A*0101 Epitopes

Eighteen of the candidate peptides were assembled with HLA-A*0101 and analyzed for MHC binding to determine their level of incorporation into MHC molecules using the REVEAL™ MHC binding assay (ProImmune Ltd., Oxford, UK). Binding to MHC molecules was compared to that of two known T-cell epitopes: an intermediate control peptide and a positive control peptide with weak and very strong binding properties, respectively. Three peptides bound to HLA-A*0101 at least 50% of the level of the positive control, as indicated on Table 1.

TABLE 1

HLA-A*0101 Binding

| SEQ ID NO | Sequence | % Positive Control |
|---|---|---|
| 1 | AVDVFLCSY | 58.58 |
| 2 | SSELESLKV | 74.14 |
| 3 | IIDPLNLFW | 91.46 |
| Intermediate Control | — | 2.25 ± 1.2 |
| Positive Control | — | 100.00 ± 15.2 |

The peptides that bound to HLA-A*0101 were synthesized as ProVE® pentamers (ProImmune Ltd., Oxford, UK) for further analysis. The pentamers were subjected to incubation and analysis at 37° C. to determine the stability of peptide-MHC complexes. Off-rates of the complexes were measured by REVEAL™ off rate analysis (ProImmune Ltd., Oxford, UK) after 0, 2, and 24 hours of incubation at 37° C. The off-rates of the peptides in terms of $t_{1/2}$ half-life values are presented in Table 2.

TABLE 2

HLA-A*0101 Off Rates

| SEQ ID NO | Sequence | $t_{1/2}$ (h) |
|---|---|---|
| 1 | AVDVFLCSY | 20.71 |
| 2 | SSELESLKV | 0.46 |
| 3 | IIDPLNLFW | 0.35 |
| Intermediate Control | — | 0.29 |
| Positive Control | — | 102.74* |

*The measurement interval of 24 hours was too short to calculate this value accurately.

Example 3

Identification of HLA-A*0301 Epitopes

Fifteen of the candidate peptides were assembled with HLA-A*0301 and analyzed for MHC binding to determine their level of incorporation into MHC molecules using the REVEAL™ MHC binding assay (ProImmune Ltd., Oxford, UK). Binding to MHC molecules was compared to that of two known T-cell epitopes: an intermediate control peptide and a positive control peptide with weak and very strong binding properties, respectively. Six peptides bound to HLA-A*0301 at at least 45% of the level of the positive control, as indicated on Table 3.

TABLE 3

HLA-A*0301 Binding

| SEQ ID NO | Sequence | % Positive Control |
| --- | --- | --- |
| 4 | KLFNKSKMK | 80.81 |
| 5 | ILAQYNTTK | 46.61 |
| 6 | YLSGKLFNK | 46.87 |
| 7 | RTRIKRSRK | 87.33 |
| 8 | LSSSLTSVK | 52.49 |
| 9 | NLFWFGIGK | 53.08 |
| Intermediate Control | — | 9.19 ± 1.5 |
| Positive Control | — | 100.00 ± 4.6 |

Five of the peptides that bound to HLA-A*0301 were synthesized as ProVE® pentamers (ProImmune Ltd., Oxford, UK) for further analysis. The pentamers were subjected to incubation and analysis at 37° C. to determine the stability of peptide-MHC complexes. Off-rates of the complexes were measured by REVEAL™ off rate analysis (ProImmune Ltd., Oxford, UK) after 0, 2, and 24 hours of incubation at 37° C. The off-rates of the peptides in terms of $t_{1/2}$ half-life values are presented in Table 4.

TABLE 4

HLA-A*0301 Off Rates

| SEQ ID NO | Sequence | $t_{1/2}$ (h) |
| --- | --- | --- |
| 4 | KLFNKSKMK | 27.81* |
| 5 | ILAQYNTTK | 2.07 |
| 7 | RTRIKRSRK | 23.92 |
| 8 | LSSSLTSVK | 1.80 |
| 9 | NLFWFGIGK | 3.35 |
| Intermediate Control | — | 0.56 |
| Positive Control | — | 49.82* |

*The measurement interval of 24 hours was too short to calculate these values accurately.

Example 4

Identification of HLA-A*0201 Epitopes

Fifty-five of the candidate peptides were assembled with HLA-A*0201 and analyzed for MHC binding to determine their level of incorporation into MHC molecules using the REVEAL™ MHC binding assay (ProImmune Ltd., Oxford, UK). Binding to MHC molecules was compared to that of two known T-cell epitopes: an intermediate control peptide and a positive control peptide with weak and very strong binding properties, respectively. Eleven peptides bound to HLA-A*0201 as well or better than the positive control, as indicated on Table 5.

TABLE 5

HLA-A*0201 Binding

| SEQ ID NO | Sequence | % Positive Control |
| --- | --- | --- |
| 10 | VLDEIKSMA | 309.26 |
| 11 | YLQWIEFSI | 112.67 |
| 12 | NLLSFAYDL | 179.71 |
| 13 | FITNNTSSV | 107.15 |
| 14 | RVLDTPYLL | 165.18 |
| 15 | SLDFAQNFI | 114.58 |
| 16 | ELVHIFLYV | 155.93 |
| 17 | LVLGSLLLL | 101.90 |
| 18 | SQLNSNPEL | 123.10 |
| 19 | ILCCVLGLL | 163.06 |
| 20 | GLLERVTRI | 131.30 |
| 21 | FLLPALIFA | 93.59 |
| Intermediate Control | — | 2.65 ± 2.1 |
| Positive Control | — | 100.00 ± 6.7 |

Twelve of the peptides that bound to HLA-A*0201 were synthesized as ProVE® pentamers (ProImmune Ltd., Oxford, UK) for further analysis. The pentamers were subjected to incubation and analysis at 37° C. to determine the stability of peptide-MHC complexes. Off-rates of the complexes were measured by REVEAL™ off rate analysis (ProImmune Ltd., Oxford, UK) after 0, 2, and 24 hours of incubation at 37° C. The off-rates of the peptides in terms of $t_{1/2}$ half-life values are presented in Table 6.

TABLE 6

HLA-A*0201 Off Rates

| SEQ ID NO | Sequence | $t_{1/2}$ (h) |
| --- | --- | --- |
| 10 | VLDEIKSMA | 1.43 |
| 11 | YLQWIEFSI | 83.00* |
| 12 | NLLSFAYDL | 1.83 |
| 13 | FITNNTSSV | 19.98 |
| 14 | RVLDTPYLL | 3.51 |
| 15 | SLDFAQNFI | 15.49 |
| 16 | ELVHIFLYV | 6.86 |
| 17 | LVLGSLLLL | 8.25 |
| 18 | SQLNSNPEL | 2.37 |
| 19 | ILCCVLGLL | 5.63 |
| 20 | GLLERVTRI | 74.30* |
| 21 | FLLPALIFA | >120* |

TABLE 6-continued

HLA-A*0201 Off Rates

| SEQ ID NO | Sequence | $t_{1/2}$ (h) |
|---|---|---|
| Intermediate Control | — | 16.18 |
| Positive Control | — | 55.67* |

*The measurement interval of 24 hours was too short to calculate these values accurately.

Example 5

Generation of Superagonist CD133 Peptides

Superagonist peptides of the CD133 epitopes described herein are produced by the methods described below. These peptide superagonists exhibit a superior capacity to induce CTL responses.

For this application T cell lines and clones are generated from peripheral blood mononuclear cells (PBMC) derived from glioma patients. Epstein Barr transformed autologous B cells are used as antigen presenting cells through all the T cell functional assays and stimulations. Blood is obtained from glioma patients and carefully layered on top of 50 ml conical tubes (polypropylene, Sarsted) in a ratio of 2 volumes per 1 volume of Histopaque (Sigma, St Louis, Mo.). Each tube is then placed in a clinical swing out centrifuge (Beckman) and spun down for 30 minutes at 400 g at room temperature. The PBMC are then collected from the interface with a transfer plastic pipette (Samco) and washed 2× with D-PBS at 250 g and 1× with culture medium (IMDM, Bio-whittaker, Walkersville, Md.) containing 8% AB human serum (Gemini Bio-products, Woodland, Calif.) at 200 g for 10 minutes each step. The supernatant is aspirated and discarded, and the cells are resuspended in culture medium.

CD8+ and CD4+ T cells are isolated from PBMC by positive selection following manufacturer's instructions (CD8 and CD4 positive selection kits, Dynal Biotech Inc., Lake Success, N.Y.). The isolated cells are used immediately for stimulation protocols.

Transformation of B cells from PBMC by Epstein Barr virus (EBV) is performed immediately after PBMC isolation. Briefly, frozen PBMCs are thawed, washed, and resuspended in CRPMI 10% FBS. 5 to 10 million PBMCs are resuspended in 2.5 ml of CRPMI 10% FBS. Then, 2.5 ml of thawed supernatant from B95.8 Marmoset cells (containing the EBV) are added to each conical tube containing the cells. The cells are incubated for 2 hours in a water bath at 37° C. CRPMI 10% FBS containing 1 µg/ml of Cyclosporin A is then added to each tube. 10 ml suspensions are transferred to T-25 flasks and incubated for 3 weeks. At this point, the cells form clumps visible to the naked eye. By microscopic examination, the cells appear large, clear and possibly hairy. These are indicators of B cell immortalization by EBV. Cells are mixed in their flasks and the 10 ml culture is split into 2 new T-25 flasks (5 ml each). 5 ml of fresh CRPMI-10 media containing 1 µg/ml cyclosporin A is added to each flask and the cultures are incubated for 1 week at 37° C. At this time point, an aliquot of each donor's cells is stained for CD19 expression (Pharmingen anti-CD19-APC stain) and analyzed by flow cytometry. The cell lines are then expanded and frozen down at 5×10$^6$/vial. Immortalized B cells are expanded in culture by splitting 1:3 in CRPMI-10 media (without cyclosporin A) in T-25 flasks once a week and incubating at 37° C., 5% $CO_2$. These lymphoblastoid B cell lines (EBV-LCL) are used as antigen presenting cells in the following T cell functional assays.

PBMC are stimulated with the reported CD133 antigens and with cancer stem cell lines in the presence of autologous dendritic cells. Briefly, T cells derived from either single well or multiple wells (bulk cultures) are used after 6-7 days of stimulation. T cell limiting dilutions are done at a concentration of 0.3, 1, 3 and 10 cells/well in 96-well round bottom plates (Corning). 1×10$^5$ irradiated autologous dendritic cells per well are added together with IL-2 and IL-7 (20 U/ml and 10 ng/ml, respectively). About five to ten times the original number of the plated cells is obtained. Wells that demonstrate growth are expanded by restimulation with a larger number of irradiated allogeneic feeders, phytohemagglutinin (PHA), and IL-2 until sufficient numbers are obtained for specificity tests. At this point, some cells are frozen while others are tested for antigen reactivity by using different readouts of T cell activation, namely cytokine production, cell killing and proliferation. Multiplex cytokine assay (Millipore, Billerica, Mass.) is performed according to the manufacturer's instructions to quantify, in an unbiased manner, a large cytokine spectrum to determine the best cytokine(s) for the evaluation of antigen specificity.

TCR profiles of the generated T cell clones are obtained to demonstrate and monitor clonality. The Vβ repertoire is determined using flow cytometry (as described above) with specific mAbs (available through Immunotech, Miami, Fla.) for cells that expand to large numbers (>10 million).

Immortalization of the antigen-responsive human T cells from PBMCs provides an advantage for the study of their fine specificity with the combinatorial libraries, because a high number of T cells are needed for the screening of the these libraries. Indeed, in order to obtain adequate data from combinatorial libraries, cells should be grown to a minimal of 30 to 100 million cells. For this reason, we the defined T cell lines and clones will be immortalized. Briefly, transduction is obtained by magnetofection in dividing T cells (recently stimulated), which are washed, counted, and plated with 100 U/ml of IL-2 in complete medium in 96 well plates (flat bottom). A mixture of the retroviral vector with Viromag R/L (OZ Biosciences) is incubated for 20 minutes before being layered onto the T cells, and the plate is then carefully set on the top of magnetic plate and incubated overnight. The next day the cells are resuspended in fresh complete medium with IL-2 and transferred to a larger well. After 48 hours the transfection efficiency is assessed by flow cytometry by staining with anti-NGFR-PE. Magnetic bead enrichment of transduced cells is performed according to Miltenyi protocols using anti-PE beads (Miltenyi).

CD133-specific T cell lines and clones are obtained within 2-4 months from the primary stimulation.

Combinatorial peptide libraries for screening for superagonist peptides are prepared as described previously in Pinilla et al., 1994, Biochem. J., 301:847-853.

T cell functional assays are performed in 96-well plates (Corning Inc., Corning, N.Y.). Each plate can accommodate 80 samples in columns 3-12, with the first 2 columns reserved for negative and positive control wells. The dispensing of samples and common reagents is accomplished using a Precision Biotek automated liquid handling instrument (Biotek, Winooski, Vt.). All samples, both libraries and individual compounds, are stored in 96-tube racks that are compatible with both the 96-well plates and the liquid handler instrumentation. Thirty plates per week are tested with the T cell functional assays. For assays that are run in duplicate, this generates approximately 1,000 data points per week. Data are acquired in the instruments specified for each type of assay and transferred to specifically designed Excel workbooks for rapid and accurate analysis.

Library mixtures are tested at a final concentration of 100 or 200 µg/ml using the general plate layout described above. Briefly, 25,000 T cells are cultured in the presence of 50,000 irradiated autologous lymphoblastoid cell lines (LCLs) and 25 µl of each mixture library at 2 mg/ml in complete RPMI. Each mixture is tested in duplicate. Control wells include T cells and LCLs without mixtures and with or without PHA (at a final concentration of 5 ug/ml). As mentioned before for antigen specificity, different readouts of T cell activation are tested to confirm the assay readout that provides the best signal for the screening with the libraries. After the screening with the library, the results are used to design individual peptides by combining the selection of the defined amino acids of the most active mixtures at each defined position. This approach provides optimized agonists and superagonist peptides of the CD133 epitopes described herein. The most active peptides are selected to determine their in vitro immunogenicity and cross reactivity with the native antigen.

Individual agonist and superagonist peptides are synthesized by the simultaneous multiple peptide synthesis method (Houghten, 1985, Proc. Natl. Acad. Sci. USA, 82:5131-35). The purity and identity of each peptide are characterized using an electrospray mass spectrometer interfaced with a liquid chromatography system.

To test the stimulatory capacity of the peptides, 25,000 T cells are cultured in the presence of 50,000 irradiated autologous LCLs and each of the individual peptides at a final concentration of 10 and 1 µg/ml. The stimulatory activity of the positive peptides is determined with dose-titration experiments to determine the concentration that yields 50% stimulatory activity (EC-50).

These studies identify superagonist peptides derived from the CD133 described herein. Strong agonist peptides recognized with EC-50 values in the nanomolar range are identified.

Example 6

Immunization with CD133 Peptides

Vaccination with CD133 epitope peptides described herein and superagonists thereof is tested for killing of tumors in humanized HLA-A2 transgenic mice. Similar methods can also be performed in mice transgenic for other HLA (see, e.g., Alexander et al., 1997, J. Immunol., 159:4753-61). The efficacy of vaccination with CD133 epitope and its superagonists with regard to peripheral cytotoxicity, intracranial tumor infiltration, and survival is tested.

Briefly, HHD mice are immunized with an epitope peptide described herein emulsified in Incomplete Freund's adjuvant and helper antigen. Bulk populations of splenocytes are tested for specific cytotoxicity against the EL4-HHD cells pulsed with the peptide, control unpulsed EL4-HHD, or EL4-HHD-peptide cells. Measurement of the peptide/HLA complex binding and stability is performed. Survival of animals vaccinated with CD133 epitope superagonists is compared.

CD133 peptides and superagonists are synthesized by N-(9-fluorenyl) methoxycarbonyl chemistry at >95% purity as indicated by analytic high-performance liquid chromatography and mass spectrometric analysis. Peptides are dissolved in PBS/10% DMSO at a concentration of 2 mg/ml and stored at −20° C. until use.

The peptides are tested in HHD mice, which are humanized with regard to HLA-A2 expression (Pascolo et al., 1997, J. Exp. Med., 185:2043-51). The HHD mice used are Dbcβ2 microglobulin null and transgenic for modified HLA-A*0201-β2 microglobulin single chain (HHD) (Eguchi et al., 2006, Cancer Res., 66:5883-91; Gross et al., 2004, J. Clin. Invest., 113:425-433).

An HHD-syngeneic tumor cell line that expresses CD133 is created. The full-length human CD133 cDNA fragment is generated by reverse transcription-PCR using forward (AGTATGGCTTTCGTTTGCTTGGC; SEQ ID NO:22) and reverse (TACCGAGCTCGGATCCACTAGT; SEQ ID NO:23) primers and CSC1 glioblastoma multiforme cancer stem cell-derived total RNA. The CD133 cDNA is then cloned into the expression plasmid pEF6/V5-His-TOPO vector (Invitrogen) to generate pEF6N5-CD133. EL4-HHD cells are then transfected with the pEF6/V5-CD133 using Cell Line Nucleofector kit T (Amaxa, Gaithersburg, Md.), and a blasticidine-resistant clone that stably expresses the highest level of CD133 based on flow-cytometry using CD133 mAb (Tessa) is selected (EL4-HHD-CD133) for further use.

Cells are stained with phycoerythrin-conjugated HLA-A*0201/peptide tetramers (10 µg/mL) in PBS containing 1% bovine serum albumin for 15 minutes at room temperature, washed once, and stained with FITC-conjugated anti-human CD8 or anti-mouse CD8 (BD Biosciences, San Diego, Calif.). Flow cytometric analyses are performed using Coulter EPICS cytometer (Beckman Coulter, Fullerton, Calif.).

To measure the peptide/HLA-A2 complex binding and stability, T2 cells ($1 \times 10^6$ cells/mL) are incubated with various concentrations (0.1-100 nmol/L) of peptides in serum-free RPMI 1640 at 37° C. overnight in an atmosphere containing 5% $CO_2$. The cells are then washed twice with PBS and stained with the BB7.2 mAb for 30 minutes at 4° C. After washing, FITC-conjugated goat anti-mouse IgG (Caltag, Burlingame, Calif.) is used as the secondary antibody. Surface expression levels of HLA-A2 are examined by flow cytometry. Peptide binding is evaluated by determining mean fluorescence intensity (MFI).

HHD mice are vaccinated (on days 0 and 7) with s.c. injections of 100 µg of peptide or superagonist emulsified in Incomplete Freund's adjuvant (IFA; Difco, Detroit, Mich.) in the presence of 140 µg of the I-Ab-restricted HBVcore128 T-helper epitope, which stimulates a CD4+ helper T-cell response. Control animals receive IFA containing HBV helper-peptide only. On day 11 after the second immunization, the animals are sacrificed, and $5 \times 10^7$ splenocytes are stimulated in vitro with the same peptide that is used for in vivo stimulation (10 µmol/L). On day 6 of culture, the bulk populations are tested for specific cytotoxicity against EL4-HHD or EL4-HHD-peptide cells.

To assess systemic protective immunity against i.c. tumor challenge, on day 7 after the second immunization, HHD mice receive an i.c. inoculation of EL4-HHD-peptide cells. Briefly, 5×104 EL4-HHD-peptide cells are stereotactically injected through an entry site at the bregma 2 mm to the right of the sagittal suture and 3 mm below the surface of the skull of anesthetized mice using a stereotactic frame. The animals are monitored daily after treatment for the manifestation of any pathologic signs.

Mice bearing i.c. EL4-HHD-peptide tumors receive immunizations on days 14 and 21 after the tumor inoculation, sacrificed by $CO_2$ asphyxiation on day 28, and perfused through the left cardiac ventricle with PBS. Brains are enzymatically digested (Walker et al., 2000, J. Immunol., 165 3128-35; Calzascia et al., 2005, Immunity, 22:175-184), and cells from each brain are resuspended in 70% Percoll (Sigma, Saint Louis, Mo.), overlaid with 37% and 30% Percoll and centrifuged for 20 minutes at 500×g. Enriched brain-infiltrating lymphocyte (BIL) populations are recovered at the 70% to 37% Percoll interface.

Survival data are compared using a log-rank test. Comparative numbers of T-cell responses are analyzed by Student's t test for two samples with unequal variances. Statistical significance is determined at the <0.05 level. Positive response is also defined as follows: the specific lysis by the responder cells against antigen-positive target cells is at least 15% and 2-fold higher than lytic levels by corresponding control conditions in at least two effector/target (E/T) ratios. Post-hoc contrasts (e.g., Student's 't' test) are performed to determine significant differences, i.e., p<0.05 between the 3 groups of animals receiving epitope vaccination, control vaccinations, and PBS vehicle control. 10 animals/group are used, sufficient to detect a 1.2 SD difference between groups at a power of 0.8 and a p=0.05.

Brain inflammation in response to vaccination is measured by performing a quantitative stereological analysis of the infiltration of T, B, and NK lymphocytes and macrophages. An immune cellular infiltrate is detected only in the intracranial tumor. Influx of CD4+, CD8+, and NK cells is observed within the tumor and peritumoral area. Increased activation of astrocytes is also observed, as evidenced by up-regulation of GFAP immunoreactivity in astrocytes.

Example 7

Induction of Immune Responses Using CD133 Superagonist Peptides

The capacity of CD133 superagonist peptides to induce CTLs capable of cross-reacting against the wild-type epitope is determined. HLA binding and stability assays are performed to determine whether the improved immunogenicity of the analog peptides is at least partially attributable to higher binding/stability of these superagonist peptides in HLA complexes that are required for specific CTL recognition. CTL assays analyzing reactivity versus peptide dose titration on T2 target cells are performed to detect whether the CTLs developed using the superagonist peptides possesses a higher functional avidity than those primed with wild-type peptide. CTL clones raised against the agonistic peptide-epitope have a more restricted T cell receptor (TCR) usage and higher TCR functional avidity than the CTL clones raised against the natural peptide-epitope.

PBMCs are obtained from glioma patients and healthy donors under an Institutional Review Board-approved protocol. HLA (e.g., HLA-A2) expression on the PBMC is validated using the monoclonal antibodies (mAb) MA2.1 (against HLA A2, B17) and BB7.2 (against HLA A2, Aw69: both from the American Type Culture Collection, Manassas, Va.) in indirect immunofluorescence assays monitored by flow cytometry.

HLA-A*0201 restricted CTL clones specific for CD133 natural and superagonist peptide-epitopes are generated in vitro. Harvested mature monocyte derived dendritic cells (mMoDC) are pulsed with natural and superagonist peptides (20 µM) and, after washing, are mixed with magnetically enriched CD8+ T cells from either thawed cryopreserved CD14 negative PBMCs or fresh PBMCs. Peptide pulsed mMoDC and enriched CD8+ T cells are mixed at a ratio of 1:20 in the presence of sCD40L (2 µg/ml) to initiate Th1-polarization of mMoDC, which boosts IL-12 production (Mailliard et al., 2002, J. Exp. Med., 195:473-483; Mailliard et al., 2004, Cancer Res., 64: 5934-37). On day three, the priming culture is supplemented with IL-2 (50 U/ml) and IL-7 (10 U/ml), and on day 12 the culture is restimulated with peptide pulsed autologous PBMC. At day 24-28, the priming culture is tested by tetramer staining for the presence of expanded primed CTL specific for the peptide used. As a positive control, priming with HLA-A*0201 restricted p24HIV-1 (SLYNVATL; SEQ ID NO:24) is run concurrently (Kan-Mitchell et al., 2006, J. Immunol., 176:6690-6701; Mitchell et al., 2007, Cancer Immunol. Immunother., 56:287-301).

For assessment of stability, patient-derived T2 cells ($1 \times 10^6$ per mL) are incubated overnight with 100 µmol/L of each peptide in serum-free RPMI 1640 at 37° C. Thereafter, the cells are washed four times to remove free peptides and incubated at 37° C. for 0, 3, or 6 hours. The cells are stained with the BB7.2 mAb to evaluate the HLA-A2 molecule expression at each time point. Peptide-induced HLA-A2 expression is evaluated by calculating the mean fluorescence of peptide-incubated T2 cells minus the mean fluorescence of T2 cells in the absence of peptide. DC50 is measured as the time required for the loss of 50% of the HLA-A2/peptide complexes stabilized at t=0.

TCR usage of CTL clones is determined by expression of variable region of β chain (V-β) of TCR. Expression of TCR-V-β and V-α among clonally expanded CD8 T cells is assessed by a real-time PCR using a fluorogenic probe (Lang et al., 1997, J. Immunol. Methods, 203:181-192). This method offers a similar degree of sensitivity to the conventional detection of TCR-V-β expression with reduced processing time. Briefly, total RNA extraction and reverse transcription are performed. In the PCR step, a V-β-specific 5' probe, common CB 3' primers, and an internal fluorogenic probe are used to amplify 26 possible V-β genes. The detection and quantitation of PCR products are done by using a 7900HT Fast Real-Time PCR System (Applied Biosystems), with which it is possible to calculate the semi-quantitative ratio of TCR V-β expression among clonally expanded CD8 T cells. Once the expression of a particular TCR V-β is determined, using the same V-β specific primer the sequence corresponding to CDR 3 is determined. This allows for delineation of the clonality of CTLs.

Tetramer decay analysis is performed to determine TCR avidity of the CTL clones (Savage et al., 1999, Immunity, 10:485-492). CTL clones are stained with tetramer (1-25 nM), as in the equilibrium binding experiments above. Cells are washed twice with FACS buffer (4% FCS and 0.1% sodium azide in PBS) and kept on ice until they are mixed with excess anti-HLA-A02 mAb (BB7.2, BD Biosciences) and then incubated at room temperature to allow for tetramer dissociation. The anti-HLA-A02 mAb is used to block rebinding of tetramer to the TCR. Dissociation is followed for 0-180 minutes, after which cells are washed quickly with ice-cold buffer to remove all unbound tetramer and blocking mAb. The cells are then fixed for flow cytometry analysis (CyanADP, Beckman-Coulter). The natural logarithm of percentage of Geometric Mean Fluorescence (GMF) at each time point (compared with 0 minutes) is plotted against time. The half-life of each pMHC multimer is derived from the slope by the equation t1/2=−ln 2/slope.

CTL activity of the in vitro primed CTL clones is measured by flow cytometry assay (Betts et al., 2003, J. Immunol. Methods, 281:65-78; Betts et al., 2004, Methods Cell Biol., 75:497-512). Briefly, the priming culture containing the CTL clone is mixed 1:1 with peptide pulsed T2 cells for 6 hours in the presence of CD107a, Monensin, and Brefeldin A. After the 6 hour incubation, cells are stained with corresponding tetramers and anti-CD8 mAb, followed by intracellular IFN-γ and TNFα staining Stained cells are run on Beckman-Coulter CyanADP (9 color, 11 parameters) for flow cytometric analysis. All the assays are run in triplicate.

To measure cytotoxicity, targets are labeled with 100 µCi of $^{51}$Cr for 60 minutes, plated in 96-well V-bottomed plates ($3\times10^3$ cell/well), and pulsed with peptides (1 µM) at 37° C. for 2 hours. Effectors are added and incubated at 37° C. for an additional 4 hours. One hundred µl of supernatant are collected, and the radioactivity is measured in a gamma counter. The percentage of specific lysis is determined as: (experimental release−spontaneous release)/(maximal release−Spontaneous Release)×100.

As a surrogate marker for CTL responses, cytokine responses, such as IFN-γ (Mailliard et al., 2004, Cancer Res., 64:5934-37; Herr et al., 2000, Blood, 96:1857-64) and IL-2 (Carrabba et al., 2003, Cancer Res., 63: 1560-67) can be monitored. IFN-γ and IL-2 secretion levels from CTL cultures stimulated with native or superagonist peptides are measured using cytokine-specific ELISA and IFN-γ enzyme-linked immunospot assays.

The relative affinity (RA) of CD133 superagonist peptides for HLA-A*0201 are measured. Briefly, T2 cells are incubated with various concentrations of peptides ranging from 100 to 0.1 µM overnight and then stained with BB7.2 mAb to quantify the surface expression of HLA-A*0201 allele. For each peptide concentration, the HLA-A*0201-specific staining is calculated as the percentage of staining obtained with 100 µM of the reference peptide HIVpol589 (IVGAETFYV; SEQ ID NO:25). The RA is determined as: RA=(concentration of each peptide that induces 20% of HLA-A*0201 expression/concentration of the reference peptide that induces 20% of HLA-A*0201 expression).

The stability of superagonist peptide/HLA-A*0201 complexes is assessed. Briefly, T2 cells are incubated overnight with 100 µM of each peptide. Cells are then incubated with Brefeldin A (Sigma, St. Louis, Mo.) at 10 µg/ml for 1 hour, washed, incubated at 37° C. for 0, 2, 4, or 6 hours in the presence of Brefeldin A (0.5 µg/ml), and then stained with BB7.2 mAb. For each time point, peptide induced HLA-A*0201 expression is calculated as: mean fluorescence of peptide preincubated T2 cells−mean fluorescence of T2 cells treated in similar conditions in the absence of peptide. DC50 is defined as the time required for the loss of 50% of the HLA-A*0201/peptide complexes stabilized at t=0.

CTL are generated from human PBMCs. PBMCs are collected by leukapheresis from healthy HLA-A*0201 volunteers. Dendritic cells are produced from adherent cells ($2\times10^6$ cells/ml) cultured for 7 days in the presence of 500 IU/ml granulocyte macrophage colony-stimulating factor (Leucomax; Schering-Plough, Kenilworth, N.J.) and 500 IU/ml IL-4 (R&D Systems, Minneapolis, Minn.) in complete medium [RPMI 1640 supplemented with 10% heat-inactivated human AB serum, 2 µM L-glutamine (Invitrogen) and antibiotics]. On day 7, dendritic cells are collected and pulsed with 40 µg/ml peptide in the presence of 3 µg/ml β2 m (Sigma) for 4 hours at 20° C. and then irradiated (4200 rad). CD8+ T cells are isolated by positive selection with immunomagnetic beads (Miltenyi Biotec, Bergisch Gladbach, Germany) according to the manufacturer's instructions. A total of $0.5\times10^6$ CD8+ T cells are cocultured with $0.25\times10^5$ dendritic cells in a final volume of 0.5 ml/well in a 48-well plate in the presence of 10 ng/ml IL-7 (R&D Systems). Human IL-10 (R&D Systems) at 10 ng/ml is added the next day, and 30 IU/ml human IL-2 (Proleukin; Chiron Corp.) is added on day two. Seven and 14 days after the primary stimulation, CD8+ T cells are restimulated with irradiated adherent cells pulsed with 10 µg/ml peptide in the presence of 3 µg/ml β2 m. Human IL-10 (10 ng/ml) and IL-2 (50 IU/ml) are added 24 and 48 hours later, respectively. Seven days after the second restimulation, individual wells from the cultures are tested for peptide specific cytotoxicity on peptide loaded T2 cells in the presence of cold K562 cells (hot/cold target ratio 1:33 ratio).

CTL are also generated from glioblastoma patients. PBMCs from a total of 30 HLA-A2+ glioma patients are evaluated for their in vitro responsiveness against wild-type and superagonist peptides. The proportion of human patients that will develop specific CTLs capable of recognizing the wild-type CD133 peptide after stimulation with the superagonist peptide is determined. It is also determined whether these CTL recognize peptide-pulsed T2 cells or HLA-A2+ cancer stem cell lines that express CD133.

Intracellular production of IFN-γ is detected. A total of $5\times10^4$ T cells are incubated with $10^5$ peptide-loaded T2 cells or with $10^5$ tumor cells in the presence of 20 µg/ml Brefeldin A at 37° C. Six hours later, the cells are stained with phycoerythrin-conjugated anti-CD8 mAb (Caltag Laboratories, Burlingame, Calif.) in PBS for 25 minutes at 4° C. and fixed with PBS 4% Paraformaldehyde (Sigma). The cells are then permeabilized with PBS+0.5% BSA+0.2% saponin (Sigma) and stained with adenomatous polyposis coli-conjugated anti-IFN-γ mAb (PharMingen, Mississauga, Ontario, Canada) for 25 minutes at 4° C. Cells are analyzed on a BD FACSCalibur™ flow cytometer (Becton Dickinson, Mountain View, Calif.).

Enzyme-linked immunosorbent spot (ELISPOT) assay kits (R & D Systems, Minneapolis, Minn.) are used to detect immune responses. Responder (R) $1\times10^5$ patients' PBMC from before and after vaccination are plated in 96-well plates with nitrocellulose membrane inserts coated with capture Ab. Stimulator (S) cells (T2 pulsed potential peptide) are added at the R:S ratio of 1:1. After a 24-hour incubation, cells are removed by washing the plates 4 times. The detection Ab is added to each well. The plates will be incubated at 4° C. overnight, and the washing steps are repeated. After a 2-hour incubation with streptavidin-alkaline phosphatase, the plates are washed. Aliquots (100 µA) of BCIP/NBT alkaline phosphatase substrate solution are added to each well to develop the spots. The reaction is stopped after 60 minutes by washing with water. The spots are scanned and counted with computer-assisted image analysis (Cellular Technology Ltd, Cleveland, Ohio). When experimental values are significantly different from the mean number of spots against non-pulsed T2 cells (background values), as determined by a two-tailed Wilcoxon rank sum test, the background values are subtracted from the experimental values. This assay provides a coefficient of variation of intra-assay for ELISPOT of less than 10%.

The superagonist-induced CTLs possess higher avidity, due to either higher affinity or stability between TCRs and peptide-MHC complexes. The higher avidity correlates with the avidity of T cell-target interactions and the antitumor responsiveness of T cells. The intensity (Yee et al., 1999, J. Immunol., 162:2227-34), or stability (Dutoit et al., 2002, J. Immunol., 168:1167-71) of specific T-cell staining with HLA tetramers, and threshold of positive staining using titrating doses of tetramers (Ercolini et al., 2005, J. Exp. Med., 201: 1591-1602) are indicative of the relative avidity of specific T cells.

Example 8

Functional Assays of Immunogenic Peptides

This example demonstrates the usefulness of some of the HLA-A2 immunogenic peptides described herein in functional assays.

HLA-A2 positive PBMC isolated by leukapheresis from two healthy human subjects were obtained from HemaCare Corporation (Van Nuys, Calif.). The PBMC from each subject were used to prepare CD8+ T cells and autologous dendritic cells for stimulation with immunogenic peptides. Following stimulation, the T cells were subjected to functional assays.

CD8+ T cells were prepared from each subject's PBMC by positive selection using CD8 MicroBeads (Miltenyi Biotec, Bergisch Gladbach, Germany), according to the manufacturer's instructions.

Autologous DC were prepared from adherent PBMC ($2 \times 10^6$ cells/ml) cultured for 5 days in the presence of 500 IU/ml granulocyte macrophage colony-stimulating factor (Leucomax; Schering-Plough, Kenilworth, N.J.) and 500 IU/ml IL-4 (R&D Systems, Minneapolis, Minn.) in complete medium [RPMI 1640 supplemented with 10% heat-inactivated human AB serum, 2 µM L-glutamine (Invitrogen) and antibiotics]. On day 5, DC maturation was induced by addition of 50 ng/ml TNF-α. On day 7, the mature DC were collected and pulsed with 20 µg/ml peptide for 4 hours at 20° C. Peptide-pulsed DC not used immediately were frozen for later use.

The peptide pulsed matured DC were diluted to $3 \times 10^5$ cells/mL in CTL complete medium and irradiated at 2800 Rads. The initial in vitro stimulation was performed at a DC:T cell ratio of 1:5 by plating 100 µL/well of each batch of DC into a 96 well round bottom tissue culture plate ($3 \times 10^4$ DC/well). One plate was prepared per peptide. To all wells, 100 µL of the CD8+ enriched T cell population was added at $1.5 \times 10^6$ cells/mL was added, resulting in a final concentration of $1.5 \times 10^5$ T-cells/well. Plates were incubated at 37° C., 5% carbon dioxide, and high humidity.

On days 7 and 14, cryopreserved peptide pulsed mature DC were thawed and used to restimulate the T-cells. Cryopreserved samples of each peptide pulsed DC batch were removed from liquid nitrogen and thawed rapidly in a 37° C. water-bath. Samples were diluted at least 1:10 with AIM V medium (Invitrogen, Carlsbard, Calif.). Samples were washed twice by centrifugation at 400 g for 7 minutes, and representative samples were evaluated for cell concentration and viability. Each DC batch was diluted to $3 \times 10^5$ cells/mL in CTL complete medium containing 20 U/mL IL-2, 10 ng/mL IL-7, and 2 µg/mL of the specific peptide, and the DC were irradiated with 2800 Rads. In vitro stimulation plates were removed carefully from the incubator and 90 µL of supernatant (no cells) were removed from each well. To each well, 100 µL of the appropriate DC batch was added. Plates were then incubated further at 37° C., 5% carbon dioxide, and high humidity.

After the second in vitro stimulation, the plates were checked daily for T-cell proliferation. When required, plates were split (one plate will become two plates) to avoid overgrowth of the CTL. Generally, this occurred on days 19, 23, 26, and 30. The plates were mixed to ensure a homogenous population, then 90 µL of each CTL well was transferred into a new 96 well U bottomed plate. When splitting was performed within 3 days of the last in vitro stimulation, 100 µL of CTL complete medium containing 20 U/mL IL-2 and 10 ng/mL IL-7 was added. If splitting was performed later than 3 days from the last in vitro stimulation, 100 µL of complete CTL medium containing 40 U/mL IL-2 and 20 ng/mL IL-7 was added. Split plates were returned to the incubator at 37° C., 5% carbon dioxide, and high humidity.

On day 21, the T cells were stimulated a fourth time. The process described for in vitro stimulations 2-3 was repeated with the exception that IL-2 was replaced with 25 ng/mL IL-15.

Stimulated CTL were assayed for staining using peptide-HLA-A2 dimers. Cells were collected 19 days after the third stimulation (subject 1) or 6 days after the fourth stimulation (subjects 1 and 2). Dimers of each peptide presented on HLA-A2 were prepared using BD™ DimerX I: Recombinant Soluble Dimeric Human HLA-A2:Ig Fusion Protein (BD Biosciences) according to the manufacturer's instructions at a 640-fold excess of peptide and 2 µg of HLA-A2:Ig protein. The HLA-A2:Ig fusion protein consists of three extracellular major histocompatibility complex (MHC) class I HLA-A2 domains that are fused to the VH regions of mouse IgG1. Immunofluorescence staining was performed essentially according to the manufacturer's instructions. The CTL were washed and resuspended in FACS staining buffer. Non-specific binding was blocked with polyclonal human IgG. Peptide-loaded HLA-A2:Ig protein was added, and the samples were incubated for 60 minutes at 4° C. The cells were washed and blocking solution of human IgG was added again. For immunofluorescence, FACS buffer containing PE-conjugated anti-mouse IgG1 was added. Following incubation at room temperature, the cells were fixed in 2% paraformaldehyde and analyzed by flow cytometry. The percentages of cells that stained positive (above background) for both dimer and CD8 are indicated in Table 7 below. SEQ ID NOs: 11 and 21 stained strongly above background, SEQ ID NOs: 28 and 29 stained moderately above background, and the SEQ ID NO:20 staining was indistinguishable from background.

TABLE 7

Peptide Dimer Staining

| SEQ ID NO | Antigen | Sequence | Subject 1 3rd stim | Subject 1 4th stim | Subject 2 4th stim |
|---|---|---|---|---|---|
| 11 | CD133 | YLQWIEFSI | 38.64 | 20.74 | 19.39 |
| 21 | CD133 | FLLPALIFA | 20.43 | 13.23 | 21.18 |
| 28 | CD133 | ILSAFSVYV | 4.15 | 0.12 | 14.08 |
| 20 | CD133 | GLLERVTRI | 0.27 | −0.41 | −0.32 |
| 29 | Mart-1a | ELAGIGILTV | 0.50 | 0.82 | 0.68 |
|  |  | no peptide | NT | 0 | 0.01 |

CTL were collected 6 days after the third and fourth stimulations for analysis by ELISPOT. Effector cells (5000 or 25,000 T cells stimulated with peptide-pulsed DC or DC without peptide) were plated in 96-well plates with nitrocellulose membrane inserts coated with anti-human IFN-γ Ab. Stimulator cells ($1 \times 10^5$ peptide-pulsed DC) were added to each well. 5 µg/ml PHA was used as a positive control. After a 16-20-hour incubation, the cells were removed by washing the plates. A biotinylated anti-human IFN-γ detection Ab (Mabtech mAb 7-B6-1 Biotin) was added to each well, and the plates were incubated at 20° C. for 2 hours. After a 1-hour incubation with avidin-phosphatase complex (Vectastain ABC Elite), the plates were washed. Aliquots of 3-amino-9-ethylcarbazole (AEC) substrate (Vectastain AEC Kit) were added to each well to develop the spots. The reaction was stopped after 4-10 minutes (when spots appeared) by washing with water. The spots were inspected visually. Wells that clearly had more spots than the negative control were indicated as positive (Table 8). For subject 1, only Mart-1a was positive; for subject 3, both Mart-1a and SEQ ID NO:11 were clearly positive.

TABLE 8

| | ELISPOT Assay | | | |
|---|---|---|---|---|
| SEQ | | Subject 1 | | Subject 2 |
| ID NO | Sequence | 3rd stim | 4th stim | 3rd stim | 4th stim |
| 11 | YLQWIEFSI | − | − | − | ++ |
| 21 | FLLPALIFA | − | − | − | − |
| 28 | ILSAFSVYV | − | − | − | − |

TABLE 8-continued

| | ELISPOT Assay | | | |
|---|---|---|---|---|
| SEQ | | Subject 1 | | Subject 2 |
| ID NO | Sequence | 3rd stim | 4th stim | 3rd stim | 4th stim |
| 20 | GLLERVTRI | − | − | − | − |
| 29 | ELAGIGILTV | − | ++ | ++ | ++ |

This example demonstrates that the immunogenic peptides disclosed herein can stimulate induction of CTL.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

---

What is claimed is:

1. An isolated peptide consisting of the amino acid sequence set forth in SEQ ID NO:21 with three or fewer amino acid substitutions within SEQ ID NO:21.

2. The isolated peptide of claim 1, wherein the peptide consists of the amino acid sequence set forth in SEQ ID NO:21 with two or fewer amino acid substitutions within SEQ ID NO:21.

3. The isolated peptide of claim 1, wherein the peptide consists of the amino acid sequence set forth in SEQ ID NO:21 with one amino acid substitution within SEQ ID NO:21.

4. The isolated peptide of claim 1, wherein the peptide consists of the amino acid sequence set forth in SEQ ID NO:21.

5. The isolated peptide of claim 1, wherein the peptide is linked to any of: an immunogenic carrier, a Toll-like receptor agonist, an immunogenic peptide known to stimulate a T helper cell type immune response, a cytokine, an antibody, a receptor ligand, a lipid, a multiple antigenic peptide, polyethylene glycol, a leader sequence, a secretory sequence, or a sequence employed for purification of the peptide.

6. A composition comprising the isolated peptide of claim 1.

7. The composition of claim 6, further comprising an adjuvant.

8. The composition of claim 7, wherein the adjuvant is selected from the group consisting of complete Freund's adjuvant, incomplete Freund's adjuvant, Montanide ISA-51, Lag-3, aluminum phosphate, aluminum hydroxide, alum, and saponin.

9. A composition comprising the isolated peptide of claim 1 linked to an immunogenic carrier.

10. The composition of claim 6, further comprising a cytokine.

11. The composition of claim 10, wherein the cytokine is selected from the group consisting of IL-1, IL-2, IL-7, IL-12, IL-13, IL-15, TNF, SCF, GM-CSF, TLR-3, TLR-4, TLR-7, and TLR-9.

12. The composition of claim 6, further comprising a liposome, an immuno-stimulating complex (ISCOM), or a slow-releasing particle.

13. The composition of claim 6, wherein the composition comprises antigen presenting cells.

14. A method of immunization comprising administering to a human subject the isolated peptide of claim 1 in an amount effective to stimulate an immune response.

15. An in vitro method for inducing a cytotoxic T lymphocyte (CTL) that is specific for a tumor cell expressing HLA-A2, the method comprising contacting a precursor CTL with the isolated peptide of claim 1 under conditions that generate a CTL response to said tumor cells.

16. A method of immunization comprising: administering to a human subject the composition of claim 6 in an amount effective to stimulate an immune response.

17. An in vitro method for inducing a cytotoxic T lymphocyte (CTL) that is specific for a tumor cell expressing HLA-A2, the method comprising contacting a precursor CTL with the composition of claim 6 under conditions that generate a CTL response to said tumor cells.

18. A method of immunization comprising: administering to a human subject the composition of claim 7 in an amount effective to stimulate an immune response.

19. An in vitro method for inducing a cytotoxic T lymphocyte (CTL) that is specific for a tumor cell expressing HLA-A2, the method comprising contacting a precursor CTL with the composition of claim 7 under conditions that generate a CTL response to said tumor cells.

20. A kit comprising the isolated peptide of claim 1.

* * * * *

UNITED STATES PATENT AND TRADEMARK OFFICE
CERTIFICATE OF CORRECTION

| | |
|---|---|
| PATENT NO. | : 8,604,167 B2 |
| APPLICATION NO. | : 13/737491 |
| DATED | : December 10, 2013 |
| INVENTOR(S) | : Manish Singh and James Bender |

It is certified that error appears in the above-identified patent and that said Letters Patent is hereby corrected as shown below:

On the Title page, Col. 2, Item (74) *Attorney, Agent, or Firm*, delete "Richarson" and insert -- Richardson --, therefor.

Signed and Sealed this
Eighth Day of April, 2014

Michelle K. Lee
*Deputy Director of the United States Patent and Trademark Office*

SEQUENCE LISTING

<160> NUMBER OF SEQ ID NOS: 35

<210> SEQ ID NO 1
<211> LENGTH: 9
<212> TYPE: PRT
<213> ORGANISM: Homo sapiens

<400> SEQUENCE: 1

Ala Val Asp Val Phe Leu Cys Ser Tyr
1               5

<210> SEQ ID NO 2
<211> LENGTH: 9
<212> TYPE: PRT
<213> ORGANISM: Homo sapiens

<400> SEQUENCE: 2

Ser Ser Glu Leu Glu Ser Leu Lys Val
1               5

<210> SEQ ID NO 3
<211> LENGTH: 9
<212> TYPE: PRT
<213> ORGANISM: Homo sapiens

<400> SEQUENCE: 3

Ile Ile Asp Pro Leu Asn Leu Phe Trp
1               5

<210> SEQ ID NO 4
<211> LENGTH: 9
<212> TYPE: PRT
<213> ORGANISM: Homo sapiens

<400> SEQUENCE: 4

Lys Leu Phe Asn Lys Ser Lys Met Lys
1               5

<210> SEQ ID NO 5
<211> LENGTH: 9
<212> TYPE: PRT
<213> ORGANISM: Homo sapiens

```
<400> SEQUENCE: 5

Ile Leu Ala Gln Tyr Asn Thr Thr Lys
1               5

<210> SEQ ID NO 6
<211> LENGTH: 9
<212> TYPE: PRT
<213> ORGANISM: Homo sapiens

<400> SEQUENCE: 6

Tyr Leu Ser Gly Lys Leu Phe Asn Lys
1               5

<210> SEQ ID NO 7
<211> LENGTH: 9
<212> TYPE: PRT
<213> ORGANISM: Homo sapiens

<400> SEQUENCE: 7

Arg Thr Arg Ile Lys Arg Ser Arg Lys
1               5

<210> SEQ ID NO 8
<211> LENGTH: 9
<212> TYPE: PRT
<213> ORGANISM: Homo sapiens

<400> SEQUENCE: 8

Leu Ser Ser Ser Leu Thr Ser Val Lys
1               5

<210> SEQ ID NO 9
<211> LENGTH: 9
<212> TYPE: PRT
<213> ORGANISM: Homo sapiens

<400> SEQUENCE: 9

Asn Leu Phe Trp Phe Gly Ile Gly Lys
1               5

<210> SEQ ID NO 10
<211> LENGTH: 9
<212> TYPE: PRT
<213> ORGANISM: Homo sapiens

<400> SEQUENCE: 10

Val Leu Asp Glu Ile Lys Ser Met Ala
1               5

<210> SEQ ID NO 11
<211> LENGTH: 9
<212> TYPE: PRT
<213> ORGANISM: Homo sapiens

<400> SEQUENCE: 11

Tyr Leu Gln Trp Ile Glu Phe Ser Ile
1               5

<210> SEQ ID NO 12
<211> LENGTH: 9
<212> TYPE: PRT
<213> ORGANISM: Homo sapiens

<400> SEQUENCE: 12

Asn Leu Leu Ser Phe Ala Tyr Asp Leu
```

<210> SEQ ID NO 13
<211> LENGTH: 9
<212> TYPE: PRT
<213> ORGANISM: Homo sapiens

<400> SEQUENCE: 13

Phe Ile Thr Asn Asn Thr Ser Ser Val
1               5

<210> SEQ ID NO 14
<211> LENGTH: 9
<212> TYPE: PRT
<213> ORGANISM: Homo sapiens

<400> SEQUENCE: 14

Arg Val Leu Asp Thr Pro Tyr Leu Leu
1               5

<210> SEQ ID NO 15
<211> LENGTH: 9
<212> TYPE: PRT
<213> ORGANISM: Homo sapiens

<400> SEQUENCE: 15

Ser Leu Asp Phe Ala Gln Asn Phe Ile
1               5

<210> SEQ ID NO 16
<211> LENGTH: 9
<212> TYPE: PRT
<213> ORGANISM: Homo sapiens

<400> SEQUENCE: 16

Glu Leu Val His Ile Phe Leu Tyr Val
1               5

<210> SEQ ID NO 17
<211> LENGTH: 9
<212> TYPE: PRT
<213> ORGANISM: Homo sapiens

<400> SEQUENCE: 17

Leu Val Leu Gly Ser Leu Leu Leu Leu
1               5

<210> SEQ ID NO 18
<211> LENGTH: 9
<212> TYPE: PRT
<213> ORGANISM: Homo sapiens

<400> SEQUENCE: 18

Ser Gln Leu Asn Ser Asn Pro Glu Leu
1               5

<210> SEQ ID NO 19
<211> LENGTH: 9
<212> TYPE: PRT
<213> ORGANISM: Homo sapiens

<400> SEQUENCE: 19

Ser Gln Leu Asn Ser Asn Pro Glu Leu
1               5

```
<210> SEQ ID NO 20
<211> LENGTH: 9
<212> TYPE: PRT
<213> ORGANISM: Homo sapiens

<400> SEQUENCE: 20

Gly Leu Leu Glu Arg Val Thr Arg Ile
 1               5

<210> SEQ ID NO 21
<211> LENGTH: 9
<212> TYPE: PRT
<213> ORGANISM: Homo sapiens

<400> SEQUENCE: 21

Phe Leu Leu Pro Ala Leu Ile Phe Ala
 1               5

<210> SEQ ID NO 22
<211> LENGTH: 23
<212> TYPE: DNA
<213> ORGANISM: Artificial Sequence
<220> FEATURE:
<223> OTHER INFORMATION: Synthetic Primer

<400> SEQUENCE: 22
agtatggctt tcgtttgctt ggc                                            23

<210> SEQ ID NO 23
<211> LENGTH: 22
<212> TYPE: DNA
<213> ORGANISM: Artificial Sequence
<220> FEATURE:
<223> OTHER INFORMATION: Synthetic Primer

<400> SEQUENCE: 23
taccgagctc ggatccacta gt                                             22

<210> SEQ ID NO 24
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 24

Ser Leu Tyr Asn Val Ala Thr Leu
 1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 25

Ile Val Gly Ala Glu Thr Phe Tyr Val
 1               5

<210> SEQ ID NO 26
<211> LENGTH: 865
<212> TYPE: PRT
<213> ORGANISM: Homo sapiens

<400> SEQUENCE: 26

Met Ala Leu Val Leu Gly Ser Leu Leu Leu Leu Gly Leu Cys Gly Asn
```

-continued

```
                1               5                  10                 15
Ser Phe Ser Gly Gly Gln Pro Ser Ser Thr Asp Ala Pro Lys Ala Trp
                20                     25                 30

Asn Tyr Glu Leu Pro Ala Thr Asn Tyr Glu Thr Gln Asp Ser His Lys
            35                 40                 45

Ala Gly Pro Ile Gly Ile Leu Phe Glu Leu Val His Ile Phe Leu Tyr
        50                 55                 60

Val Val Gln Pro Arg Asp Phe Pro Glu Asp Thr Leu Arg Lys Phe Leu
65                  70                 75                     80

Gln Lys Ala Tyr Glu Ser Lys Ile Asp Tyr Asp Lys Pro Glu Thr Val
                85                 90                 95

Ile Leu Gly Leu Lys Ile Val Tyr Tyr Glu Ala Gly Ile Ile Leu Cys
            100                105                110

Cys Val Leu Gly Leu Leu Phe Ile Ile Leu Met Pro Leu Val Gly Tyr
            115                120                125

Phe Phe Cys Met Cys Arg Cys Cys Asn Lys Cys Gly Gly Glu Met His
        130                135                140

Gln Arg Gln Lys Glu Asn Gly Pro Phe Leu Arg Lys Cys Phe Ala Ile
145                 150                155                    160

Ser Leu Leu Val Ile Cys Ile Ile Ser Ile Gly Ile Phe Tyr Gly
                165                170                175

Phe Val Ala Asn His Gln Val Arg Thr Arg Ile Lys Arg Ser Arg Lys
            180                185                190

Leu Ala Asp Ser Asn Phe Lys Asp Leu Arg Thr Leu Leu Asn Glu Thr
                195                200                205

Pro Glu Gln Ile Lys Tyr Ile Leu Ala Gln Tyr Asn Thr Thr Lys Asp
        210                215                220

Lys Ala Phe Thr Asp Leu Asn Ser Ile Asn Ser Val Leu Gly Gly Gly
225                 230                235                    240

Ile Leu Asp Arg Leu Arg Pro Asn Ile Ile Pro Val Leu Asp Glu Ile
                245                250                255

Lys Ser Met Ala Thr Ala Ile Lys Glu Thr Lys Glu Ala Leu Glu Asn
        260                265                270

Met Asn Ser Thr Leu Lys Ser Leu His Gln Gln Ser Thr Gln Leu Ser
        275                280                285

Ser Ser Leu Thr Ser Val Lys Thr Ser Leu Arg Ser Ser Leu Asn Asp
        290                295                300

Pro Leu Cys Leu Val His Pro Ser Ser Glu Thr Cys Asn Ser Ile Arg
305                 310                315                    320

Leu Ser Leu Ser Gln Leu Asn Ser Asn Pro Glu Leu Arg Gln Leu Pro
            325                330                335

Pro Val Asp Ala Glu Leu Asp Asn Val Asn Asn Val Leu Arg Thr Asp
            340                345                350

Leu Asp Gly Leu Val Gln Gln Gly Tyr Gln Ser Leu Asn Asp Ile Pro
        355                360                365

Asp Arg Val Gln Arg Gln Thr Thr Thr Val Val Ala Gly Ile Lys Arg
370                 375                380

Val Leu Asn Ser Ile Gly Ser Asp Ile Asp Asn Val Thr Gln Arg Leu
385                 390                395                    400

Pro Ile Gln Asp Ile Leu Ser Ala Phe Ser Val Tyr Val Asn Asn Thr
                405                410                415

Glu Ser Tyr Ile His Arg Asn Leu Pro Thr Leu Glu Gly Tyr Asp Ser
            420                425                430
```

-continued

Tyr Trp Trp Leu Gly Gly Leu Val Ile Cys Ser Leu Leu Thr Leu Ile
        435                 440                 445

Val Ile Phe Tyr Tyr Leu Gly Leu Leu Cys Gly Val Cys Gly Tyr Asp
450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
        515                 520                 525

Asp Thr Pro Tyr Leu Leu Asn Glu Asp Trp Glu Tyr Tyr Leu Ser Gly
530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Arg Val Leu Pro Ile
        675                 680                 685

Glu Gln Ser Leu Ser Thr Leu Tyr Gln Ser Val Lys Ile Leu Gln Arg
690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
        835                 840                 845

Asp His Val Tyr Gly Ile His Asn Pro Val Met Thr Ser Pro Ser Gln
850                 855                 860

His
865

<210> SEQ ID NO 27
<211> LENGTH: 10
<212> TYPE: PRT
<213> ORGANISM: Homo sapiens

<400> SEQUENCE: 27

Phe Leu Leu Pro Ala Leu Ile Phe Ala Val
1               5                   10

<210> SEQ ID NO 28
<211> LENGTH: 9
<212> TYPE: PRT
<213> ORGANISM: Homo sapiens

<400> SEQUENCE: 28

Ile Leu Ser Ala Phe Ser Val Tyr Val
1               5

<210> SEQ ID NO 29
<211> LENGTH: 10
<212> TYPE: PRT
<213> ORGANISM: Homo sapiens

<400> SEQUENCE: 29

Glu Leu Ala Gly Ile Gly Ile Leu Thr Val
1               5                   10

<210> SEQ ID NO 30
<211> LENGTH: 865
<212> TYPE: PRT
<213> ORGANISM: Pan troglodytes

<400> SEQUENCE: 30

Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Val Ile
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
    130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

```
Leu Ala Asp Ser Asn Phe Lys Asp Leu Arg Thr Leu Leu Asn Glu Thr
            195                 200                 205
Pro Glu Gln Ile Lys Tyr Ile Leu Ala Gln Tyr Asn Thr Thr Lys Asp
        210                 215                 220
Lys Ala Phe Thr Asp Leu Asn Ser Ile Asn Ser Val Leu Gly Gly Gly
225                 230                 235                 240
Ile Leu Asp Arg Leu Arg Pro Asn Ile Ile Pro Val Leu Asp Glu Ile
                245                 250                 255
Lys Ser Met Ala Thr Ala Ile Lys Glu Thr Lys Glu Ala Leu Glu Asn
            260                 265                 270
Met Asn Ser Thr Leu Lys Ser Leu His Gln Gln Ser Thr Gln Leu Ser
        275                 280                 285
Ser Ser Leu Thr Ser Val Lys Thr Ser Leu Arg Ser Ser Leu Asn Asp
    290                 295                 300
Pro Leu Cys Leu Val Arg Pro Ser Ser Glu Ile Cys Asn Ser Ile Arg
305                 310                 315                 320
Leu Ser Leu Ser Gln Leu Asn Ser Asn Pro Glu Leu Arg Gln Leu Pro
                325                 330                 335
Pro Val Asp Ala Glu Leu Asp Asn Val Asn Asn Val Leu Arg Thr Asp
            340                 345                 350
Leu Asp Gly Leu Val Gln Gln Gly Tyr Gln Ser Leu Asn Asp Ile Pro
        355                 360                 365
Asp Arg Val Gln Arg Gln Thr Thr Thr Val Val Ala Gly Ile Lys Arg
    370                 375                 380
Val Leu Asn Ser Ile Gly Ser Asp Ile Asp Asn Val Thr Gln Arg Leu
385                 390                 395                 400
Pro Ile Gln Asp Ile Leu Ser Glu Phe Ser Val Tyr Val Asn Asn Thr
                405                 410                 415
Glu Ser Tyr Ile His Arg Asn Leu Pro Thr Leu Glu Glu Tyr Asp Ser
            420                 425                 430
Tyr Trp Trp Leu Gly Gly Leu Val Ile Cys Ser Leu Leu Thr Leu Ile
        435                 440                 445
Val Ile Phe Tyr Tyr Leu Gly Leu Leu Cys Gly Val Cys Gly Tyr Asp
    450                 455                 460
Arg His Ala Thr Pro Thr Thr Arg Gly Cys Val Ser Asn Thr Gly Gly
465                 470                 475                 480
Val Phe Leu Met Val Gly Val Gly Leu Ser Phe Leu Phe Cys Trp Ile
                485                 490                 495
Leu Met Ile Ile Val Val Leu Thr Phe Val Phe Gly Ala Asn Val Glu
            500                 505                 510
Lys Leu Ile Cys Glu Pro Tyr Thr Ser Lys Glu Leu Phe Gln Val Leu
        515                 520                 525
Asp Thr Pro Tyr Leu Leu Asn Glu Asp Trp Glu Tyr Tyr Leu Ser Gly
    530                 535                 540
Lys Leu Phe Asn Lys Ser Lys Met Lys Leu Thr Phe Glu Gln Val Tyr
545                 550                 555                 560
Ser Asp Cys Lys Lys Asn Arg Gly Thr Tyr Gly Thr Leu His Leu Gln
                565                 570                 575
Asn Ser Phe Asn Ile Ser Glu Arg Leu Asn Ile Asn Glu His Thr Gly
            580                 585                 590
Ser Ile Ser Ser Glu Leu Glu Ser Leu Lys Val Asn Leu Asn Ile Phe
        595                 600                 605
Leu Leu Gly Ala Ala Gly Arg Lys Asn Leu Gln Asp Phe Ala Ala Cys
```

```
                610                 615                 620
Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Gln Arg Val Leu Pro Ile
                675                 680                 685

Glu Gln Ser Leu Ser Thr Leu Tyr Gln Ser Val Lys Ile Leu Gln Arg
                690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
                725                 730                 735

Glu Glu Thr Lys Lys Tyr Gly Arg Thr Ile Ile Gly Tyr Phe Glu His
                740                 745                 750

Tyr Leu Gln Trp Ile Glu Phe Ser Ile Ser Glu Lys Val Ala Ser Cys
                755                 760                 765

Lys Pro Val Ala Thr Ala Leu Asp Thr Ala Val Asp Val Phe Leu Cys
770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
                820                 825                 830

Thr Ile Pro Met Lys Asn Met Glu Asn Gly Asn Asn Gly Tyr His Lys
                835                 840                 845

Asp His Val Tyr Gly Ile His Asn Pro Val Met Thr Ser Pro Ser Gln
                850                 855                 860

His
865

<210> SEQ ID NO 31
<211> LENGTH: 841
<212> TYPE: PRT
<213> ORGANISM: Macaca mulatta

<400> SEQUENCE: 31

Met Ala Leu Val Leu Gly Ser Leu Leu Leu Leu Gly Leu Cys Gly Asn
 1               5                   10                  15

Ser Phe Ser Gly Gly Gln Pro Ser Ser Thr Asp Ala Pro Lys Ala Trp
                20                  25                  30

Asn Tyr Glu Leu Pro Ala Thr Asn Tyr Glu Thr Gln Asp Ser His Thr
                35                  40                  45

Ala Gly Pro Ile Gly Ile Leu Phe Glu Leu Val His Ile Phe Leu Tyr
        50                  55                  60

Val Val Gln Pro Arg Asp Phe Pro Glu Asp Thr Leu Arg Lys Val Ile
65                  70                  75                  80

Gln Lys Ala Arg Glu Ser Lys Ile Asp Tyr Asp Lys Pro Glu Thr Leu
                85                  90                  95

Ile Leu Gly Leu Lys Ile Ile Tyr Tyr Glu Ala Gly Ile Ile Leu Cys
                100                 105                 110

Ser Val Leu Gly Leu Leu Phe Ile Ile Leu Met Pro Leu Val Gly Tyr
```

```
            115                 120                 125
Phe Phe Cys Met Cys Arg Cys Cys Asn Lys Cys Gly Gly Glu Met His
130                 135                 140
Gln Arg Gln Lys Glu Asn Gly Leu Phe Leu Arg Lys Cys Phe Ala Ile
145                 150                 155                 160
Ser Leu Leu Val Ile Cys Ile Ile Ser Ile Gly Ile Phe Cys Gly
                165                 170                 175
Phe Val Ala Asn His Gln Val Arg Thr Arg Ile Lys Arg Ser Arg Lys
                180                 185                 190
Leu Ala Asp Ser Asn Phe Lys Asp Leu Arg Thr Leu Leu Asn Glu Thr
                195                 200                 205
Pro Glu Gln Ile Lys Tyr Ile Leu Ala Gln Tyr Asn Thr Thr Lys Asp
210                 215                 220
Lys Ala Phe Ser Asp Leu Asn Ser Ile Asn Ser Val Leu Gly Gly Gly
225                 230                 235                 240
Ile Leu Asp Arg Leu Arg Pro Asn Ile Ile Pro Val Leu Asp Glu Ile
                245                 250                 255
Lys Ser Met Ala Thr Ala Ile Lys Glu Thr Lys Glu Ala Leu Glu Asn
                260                 265                 270
Met Asn Ser Thr Leu Lys Ser Leu His Gln Gln Ser Thr Gln Leu Ser
                275                 280                 285
Ser Ser Leu Thr Ser Val Lys Thr Ser Leu Arg Ala Ser Leu Asn Asp
290                 295                 300
Pro Leu Cys Ser Val Arg Pro Ser Ser Glu Thr Cys Asn Ser Ile Arg
305                 310                 315                 320
Leu Ser Leu Ser Gln Leu Asn Ser Asn Pro Glu Leu Arg Gln Leu Pro
                325                 330                 335
Ser Val Asp Ala Glu Leu Asp Lys Val Asn Asn Val Leu Arg Thr Asp
                340                 345                 350
Leu Asp Gly Leu Val Gln Gln Gly Tyr Gln Ser Leu Asn Asp Ile Pro
                355                 360                 365
Asp Arg Val Gln Ser Gln Thr Lys Thr Val Val Ala Gly Ile Lys Arg
370                 375                 380
Val Leu Asn Ser Ile Gly Ser Asp Ile Asp Asn Val Thr Gln His Leu
385                 390                 395                 400
Pro Ile Gln Asn Ile Leu Ser Glu Phe Ser Val Tyr Val Asn Asn Thr
                405                 410                 415
Glu Ser Tyr Ile His Arg Asn Leu Pro Thr Leu Glu Glu Tyr Asp Ser
                420                 425                 430
Tyr Trp Trp Leu Gly Gly Leu Val Ile Cys Ser Leu Leu Thr Leu Ile
                435                 440                 445
Val Ile Phe Tyr Tyr Leu Gly Leu Leu Cys Gly Val Cys Gly Tyr Asp
450                 455                 460
Arg His Ala Thr Pro Thr Thr Arg Gly Cys Val Ser Asn Thr Gly Gly
465                 470                 475                 480
Val Phe Leu Met Val Gly Val Gly Leu Ser Phe Leu Phe Cys Trp Ile
                485                 490                 495
Leu Met Ile Ile Val Val Leu Thr Phe Val Phe Gly Ala Asn Val Glu
                500                 505                 510
Lys Leu Ile Cys Glu Pro Tyr Thr Ser Lys Glu Leu Phe Arg Val Leu
                515                 520                 525
Asp Thr Pro Tyr Leu Leu Asn Glu Asp Trp Glu Tyr Tyr Leu Ser Gly
530                 535                 540
```

```
Lys Leu Phe Asn Lys Ser Glu Met Lys Leu Thr Phe Gln Gln Val Tyr
545                 550                 555                 560

Ser Asp Cys Lys Lys Asn Arg Gly Thr Tyr Gly Thr Leu His Leu Glu
            565                 570                 575

Asn Ser Phe Asp Ile Ser Asp Tyr Leu Asn Ile Asn Glu His Thr Ala
        580                 585                 590

Ser Ile Ser Ser Glu Leu Glu Ser Leu Lys Val Asn Leu Asn Ile Phe
595                 600                 605

Leu Leu Gly Ala Ala Gly Arg Lys Ser Leu Gln Asp Phe Ala Ala Cys
610                 615                 620

Gly Ile Asp Arg Met Asn Tyr Asp Thr Tyr Leu Ala Gln Thr Gly Lys
625                 630                 635                 640

Ser Pro Ala Gly Val Asn Leu Leu Ser Phe Ala Tyr Asp Leu Glu Ala
            645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gln Arg Val Leu Pro Ile
        675                 680                 685

Glu Gln Ser Leu Ser Thr Leu Tyr Gln Ser Val Lys Ile Leu Gln Arg
690                 695                 700

Thr Gly Asn Gly Leu Leu Glu Arg Val Asn Arg Ile Leu Ala Ser Leu
705                 710                 715                 720

Asp Phe Ala Gln Asn Phe Ile Thr Asn Asn Ile Ser Ser Val Ile Ile
            725                 730                 735

Glu Glu Thr Lys Lys Tyr Arg Lys Thr Ile Ile Gly Tyr Phe Glu His
            740                 745                 750

Tyr Met Gln Trp Ile Glu Phe Ser Ile Ser Glu Lys Val Ala Ser Cys
        755                 760                 765

Lys Pro Val Ala Thr Ala Leu Asp Thr Ala Val Asp Val Phe Leu Cys
        770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
            805                 810                 815

Lys Tyr Tyr Arg Arg Met Asp Ser Glu Asp Val Tyr Asp Asp Val Glu
            820                 825                 830

Thr Ile Pro Met Lys Asn Pro Ser His
        835                 840

<210> SEQ ID NO 32
<211> LENGTH: 857
<212> TYPE: PRT
<213> ORGANISM: Rattus norvegicus

<400> SEQUENCE: 32

Met Ala Leu Val Phe Ser Val Leu Leu Leu Gly Leu Cys Gly Lys
 1               5                  10                  15

Met Ala Ser Gly Gly Gln Pro Ala Phe Asp Asn Thr Pro Gly Ala Leu
            20                  25                  30

Asn Tyr Glu Leu Pro Thr Thr Glu Tyr Glu Thr Gln Asp Thr Phe Asn
        35                  40                  45

Ala Gly Ile Ile Asp Pro Leu Tyr Gln Met Val His Ile Phe Leu Asn
    50                  55                  60

Val Val Gln Pro Asn Asp Phe Pro Gln Asp Leu Val Lys Lys Leu Ile
65                  70                  75                  80
```

-continued

```
Gln Lys Arg Phe Asp Ile Ser Val Asp Thr Lys Val Ala Ile Tyr
                85                  90                  95
Glu Ile Gly Val Leu Ile Cys Val Ile Leu Gly Leu Leu Phe Ile Phe
           100                 105                 110
Leu Met Pro Leu Val Gly Phe Phe Cys Met Cys Arg Cys Cys Asn
       115                 120                 125
Lys Cys Gly Gly Glu Met His Gln Arg Gln Lys Gln Asn Glu Ser Cys
       130                 135                 140
Arg Arg Lys Cys Leu Ala Ile Ser Leu Leu Leu Ile Cys Leu Leu Met
145                 150                 155                 160
Ser Leu Gly Ile Ala Phe Gly Phe Val Ala Asn Gln Gln Thr Arg Thr
                165                 170                 175
Arg Ile Gln Arg Thr Gln Lys Leu Ala Glu Ser Asn Tyr Arg Asp Leu
           180                 185                 190
Arg Ala Leu Leu Thr Glu Ala Pro Lys Gln Ile Asp Tyr Ile Leu Gly
       195                 200                 205
Gln Tyr Asn Thr Thr Lys Asn Lys Ala Phe Ser Asp Leu Asp Ser Ile
       210                 215                 220
Asp Ser Val Leu Gly Gly Arg Ile Lys Gly Gln Leu Lys Pro Lys Val
225                 230                 235                 240
Thr Pro Val Leu Glu Glu Ile Lys Ala Met Ala Thr Ala Ile Arg Gln
                245                 250                 255
Thr Lys Asp Ala Leu Gln Asn Met Ser Ser Leu Lys Ser Leu Arg
           260                 265                 270
Asp Ala Ser Thr Gln Leu Ser Thr Asn Leu Thr Ser Val Arg Asn Ser
       275                 280                 285
Ile Glu Asn Ser Leu Asn Ser Asn Asp Cys Ala Ser Asp Pro Ala Ser
       290                 295                 300
Lys Ile Cys Asp Ser Leu Arg Pro Gln Leu Ser Asn Leu Gly Ser Asn
305                 310                 315                 320
His Asn Gly Ser Gln Leu Pro Ser Val Asp Arg Glu Leu Asn Thr Val
                325                 330                 335
Asn Asp Val Asp Arg Thr Asp Leu Glu Ser Leu Val Lys Arg Gly Tyr
           340                 345                 350
Met Ser Ile Asp Glu Ile Pro Asn Met Ile Gln Asn Gln Thr Gly Asp
       355                 360                 365
Val Ile Lys Asp Val Lys Lys Thr Leu Asp Ser Val Ser Ser Lys Val
       370                 375                 380
Lys Asn Met Ser Gln Ser Ile Pro Val Glu Glu Val Leu Leu Gln Phe
385                 390                 395                 400
Ser His Tyr Leu Asn Asp Ser Asn Arg Tyr Ile His Glu Ser Leu Pro
                405                 410                 415
Arg Val Glu Glu Tyr Asp Ser Tyr Trp Trp Leu Gly Gly Leu Ile Val
           420                 425                 430
Cys Phe Leu Leu Thr Leu Ile Val Thr Phe Phe Tyr Leu Gly Leu Leu
       435                 440                 445
Cys Gly Val Phe Gly Tyr Asp Lys Arg Ala Thr Pro Thr Arg Arg Gly
       450                 455                 460
Cys Val Ser Asn Thr Gly Gly Ile Phe Leu Met Ala Gly Val Gly Phe
465                 470                 475                 480
Ser Phe Leu Phe Cys Trp Ile Leu Met Ile Leu Val Val Leu Thr Phe
                485                 490                 495
Val Val Gly Ala Asn Val Glu Lys Leu Leu Cys Glu Pro Tyr Glu Asn
           500                 505                 510
```

```
Lys Lys Leu Leu Gln Val Leu Asp Thr Pro Tyr Leu Leu Asn Asp Gln
        515                 520                 525

Trp Gln Phe Tyr Leu Ser Gly Ile Leu Leu Lys Asn Pro Asp Ile Asn
530                 535                 540

Met Thr Phe Glu Gln Val Tyr Arg Asp Cys Lys Arg Gly Arg Gly Val
545                 550                 555                 560

Tyr Ala Thr Phe Gln Leu Glu Asn Val Phe Asn Ile Thr Glu Asn Phe
                565                 570                 575

Asn Ile Glu Arg Leu Ser Glu Asp Ile Val Lys Glu Leu Glu Lys Leu
            580                 585                 590

Asn Val Asn Ile Asp Ser Ile Glu Leu Leu Asp Lys Thr Gly Arg Lys
        595                 600                 605

Ser Leu Glu Asp Phe Ala Gln Ser Gly Ile Asp Arg Ile Asn Tyr Ser
    610                 615                 620

Met Tyr Leu Gln Glu Ala Glu Lys Pro Pro Thr Lys Val Asp Leu Leu
625                 630                 635                 640

Thr Phe Ala Ser Phe Leu Glu Thr Glu Ala Asn Gln Leu Pro Asp Gly
                645                 650                 655

Asn Leu Lys Gln Ala Phe Leu Met Asp Ala Gln Asn Ile Arg Ala Ile
            660                 665                 670

His Gln Gln His Val Pro Pro Val Gln Gln Ser Leu Asn Ser Leu Lys
        675                 680                 685

Gln Ser Val Trp Ala Leu Lys Gln Thr Ser Ser Lys Leu Pro Glu Glu
    690                 695                 700

Val Lys Lys Val Leu Ala Ser Leu Asp Ser Ala Gln His Phe Leu Thr
705                 710                 715                 720

Ser Asn Leu Ser Ser Ile Val Ile Gly Glu Thr Lys Lys Phe Gly Arg
                725                 730                 735

Thr Ile Ile Gly Tyr Phe Glu His Tyr Leu Gln Trp Val Leu Tyr Ala
            740                 745                 750

Ile Thr Glu Lys Met Thr Ser Cys Lys Pro Met Ile Thr Ala Met Asp
        755                 760                 765

Ser Ala Val Asn Gly Ile Leu Cys Ser Tyr Val Ala Asp Pro Leu Asn
    770                 775                 780

Leu Phe Trp Phe Gly Ile Gly Lys Ala Thr Met Leu Leu Leu Pro Ala
785                 790                 795                 800

Val Ile Ile Ala Ile Lys Leu Ala Lys Tyr Tyr Arg Arg Met Asp Ser
                805                 810                 815

Glu Asp Val Tyr Asp Asp Val Glu Thr Val Pro Met Lys Asn Leu Glu
            820                 825                 830

Asn Gly Ser Asn Gly Tyr His Lys Asp His Leu Tyr Gly Val His Asn
        835                 840                 845

Pro Val Met Thr Ser Pro Ser Arg Tyr
    850                 855

<210> SEQ ID NO 33
<211> LENGTH: 867
<212> TYPE: PRT
<213> ORGANISM: Mus musculus

<400> SEQUENCE: 33

Met Ala Leu Val Phe Ser Ala Leu Leu Leu Gly Leu Cys Gly Lys
1               5                   10                  15

Ile Ser Ser Glu Gly Gln Pro Ala Phe His Asn Thr Pro Gly Ala Met
                20                  25                  30
```

Asn Tyr Glu Leu Pro Thr Thr Lys Tyr Glu Thr Gln Asp Thr Phe Asn
            35                  40                  45

Ala Gly Ile Val Gly Pro Leu Tyr Lys Met Val His Ile Phe Leu Ser
 50                  55                  60

Val Val Gln Pro Asn Asp Phe Pro Leu Asp Leu Ile Lys Lys Leu Ile
 65                  70                  75                  80

Gln Asn Lys Lys Phe Asp Ile Ser Val Asp Ser Lys Glu Pro Glu Ile
                    85                  90                  95

Ile Val Leu Ala Leu Lys Ile Ala Leu Tyr Glu Ile Gly Val Leu Ile
                100                 105                 110

Cys Ala Ile Leu Gly Leu Leu Phe Ile Ile Leu Met Pro Leu Val Gly
            115                 120                 125

Cys Phe Phe Cys Met Cys Arg Cys Cys Asn Lys Cys Gly Gly Glu Met
    130                 135                 140

His Gln Arg Gln Lys Gln Asn Ala Pro Cys Arg Arg Lys Cys Leu Gly
145                 150                 155                 160

Leu Ser Leu Leu Val Ile Cys Leu Leu Met Ser Leu Gly Ile Ile Tyr
                165                 170                 175

Gly Phe Val Ala Asn Gln Gln Thr Arg Thr Arg Ile Lys Gly Thr Gln
                180                 185                 190

Lys Leu Ala Lys Ser Asn Phe Arg Asp Phe Gln Thr Leu Leu Thr Glu
            195                 200                 205

Thr Pro Lys Gln Ile Asp Tyr Val Val Glu Gln Tyr Thr Asn Thr Lys
    210                 215                 220

Asn Lys Ala Phe Ser Asp Leu Asp Gly Ile Gly Ser Val Leu Gly Gly
225                 230                 235                 240

Arg Ile Lys Asp Gln Leu Lys Pro Lys Val Thr Pro Val Leu Glu Glu
                245                 250                 255

Ile Lys Ala Met Ala Thr Ala Ile Lys Gln Thr Lys Asp Ala Leu Gln
            260                 265                 270

Asn Met Ser Ser Ser Leu Lys Ser Leu Gln Asp Ala Ala Thr Gln Leu
    275                 280                 285

Asn Thr Asn Leu Ser Ser Val Arg Asn Ser Ile Glu Asn Ser Leu Ser
    290                 295                 300

Ser Ser Asp Cys Thr Ser Asp Pro Ala Ser Lys Ile Cys Asp Ser Ile
305                 310                 315                 320

Arg Pro Ser Leu Ser Ser Leu Gly Ser Ser Leu Asn Ser Ser Gln Leu
                325                 330                 335

Pro Ser Val Asp Arg Glu Leu Asn Thr Val Thr Glu Val Asp Lys Thr
            340                 345                 350

Asp Leu Glu Ser Leu Val Lys Arg Gly Tyr Thr Thr Ile Asp Glu Ile
    355                 360                 365

Pro Asn Thr Ile Gln Asn Gln Thr Val Asp Val Ile Lys Asp Val Lys
    370                 375                 380

Asn Thr Leu Asp Ser Ile Ser Ser Asn Ile Lys Asp Met Ser Gln Ser
385                 390                 395                 400

Ile Pro Ile Glu Asp Met Leu Leu Gln Val Ser His Tyr Leu Asn Asn
                405                 410                 415

Ser Asn Arg Tyr Leu Asn Gln Glu Leu Pro Lys Leu Glu Glu Tyr Asp
            420                 425                 430

Ser Tyr Trp Trp Leu Gly Gly Leu Ile Val Cys Phe Leu Leu Thr Leu
    435                 440                 445

Ile Val Thr Phe Phe Phe Leu Gly Leu Leu Cys Gly Val Phe Gly Tyr

```
              450                 455                 460
Asp Lys His Ala Thr Pro Thr Arg Arg Gly Cys Val Ser Asn Thr Gly
465                 470                 475                 480

Gly Ile Phe Leu Met Ala Gly Val Gly Phe Gly Phe Leu Phe Cys Trp
                    485                 490                 495

Ile Leu Met Ile Leu Val Val Leu Thr Phe Val Val Gly Ala Asn Val
                    500                 505                 510

Glu Lys Leu Leu Cys Glu Pro Tyr Glu Asn Lys Lys Leu Leu Gln Val
                    515                 520                 525

Leu Asp Thr Pro Tyr Leu Leu Lys Glu Gln Trp Gln Phe Tyr Leu Ser
530                 535                 540

Gly Met Leu Phe Asn Asn Pro Asp Ile Asn Met Thr Phe Glu Gln Val
545                 550                 555                 560

Tyr Arg Asp Cys Lys Arg Gly Arg Gly Ile Tyr Ala Ala Phe Gln Leu
                    565                 570                 575

Glu Asn Val Val Asn Val Ser Asp His Phe Asn Ile Asp Gln Ile Ser
                    580                 585                 590

Glu Asn Ile Asn Thr Glu Leu Glu Asn Leu Asn Val Asn Ile Asp Ser
                    595                 600                 605

Ile Glu Leu Leu Asp Asn Thr Gly Arg Lys Ser Leu Glu Asp Phe Ala
610                 615                 620

His Ser Gly Ile Asp Thr Ile Asp Tyr Ser Thr Tyr Leu Lys Glu Thr
625                 630                 635                 640

Glu Lys Ser Pro Thr Glu Val Asn Leu Leu Thr Phe Ala Ser Thr Leu
                    645                 650                 655

Glu Ala Lys Ala Asn Gln Leu Pro Glu Gly Lys Pro Lys Gln Ala Phe
                    660                 665                 670

Leu Leu Asp Val Gln Asn Ile Arg Ala Ile His Gln His Leu Leu Pro
                    675                 680                 685

Pro Val Gln Gln Ser Leu Asn Thr Leu Arg Gln Ser Val Trp Thr Leu
                    690                 695                 700

Gln Gln Thr Ser Asn Lys Leu Pro Glu Lys Val Lys Lys Ile Leu Ala
705                 710                 715                 720

Ser Leu Asp Ser Val Gln His Phe Leu Thr Asn Asn Val Ser Leu Ile
                    725                 730                 735

Val Ile Gly Glu Thr Lys Lys Phe Gly Lys Thr Ile Leu Gly Tyr Phe
                    740                 745                 750

Glu His Tyr Leu His Trp Val Phe Tyr Ala Ile Thr Glu Lys Met Thr
                    755                 760                 765

Ser Cys Lys Pro Met Ala Thr Ala Met Asp Ser Ala Val Asn Gly Ile
770                 775                 780

Leu Cys Gly Tyr Val Ala Asp Pro Leu Asn Leu Phe Trp Phe Gly Ile
785                 790                 795                 800

Gly Lys Ala Thr Val Leu Leu Pro Ala Val Ile Ala Ile Lys
                    805                 810                 815

Leu Ala Lys Tyr Tyr Arg Arg Met Asp Ser Glu Asp Val Tyr Asp Asp
                    820                 825                 830

Val Glu Thr Val Pro Met Lys Asn Leu Glu Ile Gly Ser Asn Gly Tyr
                    835                 840                 845

His Lys Asp His Leu Tyr Gly Val His Asn Pro Val Met Thr Ser Pro
                    850                 855                 860

Ser Arg Tyr
865
```

<210> SEQ ID NO 34
<211> LENGTH: 822
<212> TYPE: PRT
<213> ORGANISM: Canis familiaris

<400> SEQUENCE: 34

```
Met Ala Leu Leu Leu Gly Phe Leu Leu Leu Glu Leu Cys Trp Asp
  1               5                  10                  15

Thr Ser Ala Leu Gly Pro Leu Ser Ser Thr Lys Gly Ser Asp Gly Leu
             20                  25                  30

Glu Phe Glu Leu Pro Ala Thr Asn Tyr Glu Thr Lys Asp Ser Asn Gln
         35                  40                  45

Ala Gly Pro Ile Ser Val Leu Phe Gln Ile Val Gln Val Phe Leu Gln
     50                  55                  60

Val Val Gln Pro His Pro Phe Pro Glu Asp Ile Leu Arg Lys Ile Leu
 65                  70                  75                  80

Gln Lys Lys Phe Asp Phe Ser Thr Asp Tyr Asp Lys Ile Ile Tyr Tyr
                 85                  90                  95

Glu Ile Gly Ile Ile Ile Cys Ala Val Leu Gly Leu Leu Phe Val Ile
            100                 105                 110

Leu Met Pro Leu Val Gly Phe Cys Phe Gly Leu Cys Arg Cys Cys Asn
        115                 120                 125

Lys Cys Gly Gly Glu Met His Gln Arg Gln Lys Lys Asn Gly Ala Phe
    130                 135                 140

Leu Arg Lys Tyr Phe Thr Val Ser Leu Leu Val Ile Cys Ile Phe Ile
145                 150                 155                 160

Ser Val Gly Ile Ile Tyr Gly Phe Val Ala Asn His His Leu Arg Thr
                165                 170                 175

Arg Ile Glu Lys Thr Arg Lys Leu Ala Glu Ser Asn Leu Lys Asp Leu
            180                 185                 190

Arg Thr Leu Leu Ile Gly Thr Pro Ala Gln Ile Asn Tyr Val Leu Ser
        195                 200                 205

Gln Tyr Ala Ser Thr Lys Glu Lys Ala Phe Ser Asp Leu Asp Asn Ile
    210                 215                 220

Lys Ser Leu Leu Gly Gly Ile His Asp Gln Leu Arg Pro Lys Val
225                 230                 235                 240

Ile Pro Val Leu Asp Asp Ile Lys Ala Met Ala Glu Ala Ile Lys Glu
                245                 250                 255

Thr Arg Glu Ala Leu Leu Asn Val Asn Asn Thr Leu Lys Glu Leu Lys
            260                 265                 270

Met Ser Thr Ala Gln Leu Asn Thr Ser Leu Ser Asp Val Lys Arg Asn
        275                 280                 285

Leu Glu Gln Ser Leu Asn Asp Pro Met Cys Ser Val Pro Pro Val Ala
    290                 295                 300

Thr Thr Cys Asn Asn Ile Arg Met Ser Leu Gly Gln Leu Asp Asp Asn
305                 310                 315                 320

Thr Asn Leu Gly Gln Leu Pro Ser Leu Asp Lys Gln Ile Asp Asn Ile
                325                 330                 335

Asn Asn Val Leu Gln Thr Asp Leu Ser Ser Leu Val Gln Lys Gly Tyr
            340                 345                 350

Lys Ser Phe Asn Asp Ile Pro Glu Met Val Gln Asn Gln Thr Thr Asp
        355                 360                 365

Ile Val Ser Asp Val Lys Arg Thr Leu Asn Ser Leu Gly Ser Asp Ile
    370                 375                 380
```

```
Glu Asn Met Ser Glu Gln Ile Pro Ile Gln Asp Lys Leu Ser Asp Phe
385                 390                 395                 400

Ile Gly Tyr Ile Asn Asp Thr Glu Thr Tyr Ile His Arg Asn Leu Pro
            405                 410                 415

Thr Leu Glu Glu Tyr Asp Ser Tyr Arg Trp Leu Gly Gly Leu Ile Val
        420                 425                 430

Cys Cys Leu Leu Thr Leu Ile Val Val Phe Tyr Tyr Leu Gly Leu Met
        435                 440                 445

Cys Gly Thr Phe Gly Tyr Asp Arg His Ala Thr Pro Thr Arg Arg Gly
        450                 455                 460

Cys Val Ser Asn Thr Gly Gly Ile Phe Leu Met Val Gly Val Gly Ile
465                 470                 475                 480

Ser Phe Leu Phe Cys Trp Ile Leu Met Thr Ile Val Val Leu Thr Phe
            485                 490                 495

Val Ile Gly Gly Asn Met Glu Lys Leu Val Cys Glu Pro Tyr Gln Asn
        500                 505                 510

Arg Lys Leu Phe Gln Ile Leu Asp Thr Pro Tyr Leu Leu Asn Glu Asn
        515                 520                 525

Trp Lys Tyr Tyr Leu Ser Gly Met Val Leu Asp Lys Pro Asp Ile Asn
530                 535                 540

Leu Thr Phe Glu Gln Val Tyr Ser Asp Cys Lys Glu Asn Lys Gly Ile
545                 550                 555                 560

Tyr Ser Thr Leu Lys Leu Glu Asn Thr Tyr Asn Ile Ser Glu His Leu
            565                 570                 575

Asn Ile Gln Glu His Ala Arg Asn Leu Ser Asn Asp Phe Lys Asn Met
            580                 585                 590

Asn Val Asn Ile Asp Asn Ile Val Leu Leu Asp Ala Ala Gly Arg Lys
            595                 600                 605

Asn Leu Met Asp Phe Ser Ser Ser Gly Val Asp Thr Ile Asp Tyr Asn
            610                 615                 620

Val Tyr Leu Ala Glu Met Gly Lys Thr Pro Thr Lys Val Asn Leu Leu
625                 630                 635                 640

Ser Phe Ala Asp Asp Leu Asp Thr Lys Ala Asn Asn Leu Pro Gln Gly
                645                 650                 655

Ser Leu Lys Gln Ser Leu Lys Asn Asn Ala Gln Asn Leu Lys Thr Ile
            660                 665                 670

His His Gly Gln Val Met Pro Leu Glu Gln Ser Met Ser Thr Ile Asn
        675                 680                 685

Gln Ser Ile Lys Glu Leu Gln His Lys Ser Ser Gly Leu Arg Val Lys
        690                 695                 700

Val Ala Asn Ile Leu Ser Ser Leu Asp Ser Ala Gln Asp Phe Leu Gln
705                 710                 715                 720

Thr Arg Ile Ser Ser Val Ile Val Lys Glu Ser Ser Lys Tyr Gly Asn
                725                 730                 735

Met Ile Ile Gly Tyr Phe Glu His Tyr Leu Gln Trp Val Lys Ile Ser
            740                 745                 750

Ile Thr Glu Gln Ile Ala Ala Cys Lys Pro Val Ala Thr Ala Leu Asp
        755                 760                 765

Ser Ala Val Asp Val Phe Leu Cys Ser Tyr Ile Asp Pro Met Asn
770                 775                 780

Leu Phe Trp Phe Gly Ile Gly Lys Ala Thr Ile Phe Leu Leu Pro Ala
785                 790                 795                 800

Ile Ile Phe Ala Val Lys Leu Ala Lys Tyr Tyr Arg Arg Met Asp Ser
                805                 810                 815
```

```
Glu Asp Val Tyr Asp Glu
            820

<210> SEQ ID NO 35
<211> LENGTH: 889
<212> TYPE: PRT
<213> ORGANISM: Bos taurus

<400> SEQUENCE: 35

Met Ala Leu Leu Leu Gly Phe Leu Leu Leu Gly Leu Cys Glu Asp
  1               5                  10                  15

Thr Leu Ser Glu Glu Leu Ser Ser Gly Tyr Arg Pro Asp Gly Leu
             20                  25                  30

Glu Phe Gln Leu Pro Pro Thr Ser Tyr Gln Thr Ser Asp Ser Tyr Asp
             35                  40                  45

Pro Gly Leu Ala Gly Phe Phe Gln Ile Val Arg Phe Val Gln
         50                  55                  60

Ile Val Gln Pro Asn Ala Phe Pro Glu Asp Ile Leu Arg Lys Ile Ile
 65                  70                  75                  80

Gln Lys Lys Phe Asp Leu Ser Lys Glu Tyr Asp Lys Pro Glu Asn Val
                 85                  90                  95

Val Leu Thr Leu Lys Ile Ile Tyr Tyr Glu Ile Gly Ile Ile Ile Cys
            100                 105                 110

Ala Ala Leu Gly Leu Leu Phe Val Ile Leu Met Pro Leu Val Gly Phe
            115                 120                 125

Phe Phe Cys Leu Cys Arg Cys Cys Asn Lys Cys Gly Gly Glu Met His
            130                 135                 140

Gln Arg Gln Lys Lys Ser Gly Pro Phe Leu Lys Lys Tyr Phe Thr Ile
145                 150                 155                 160

Ser Leu Leu Val Ile Cys Val Phe Ile Ser Ile Gly Ile Ile Tyr Gly
                165                 170                 175

Phe Ala Ala Asn His Tyr Met Arg Thr Asn Val Glu Glu Thr Arg Lys
            180                 185                 190

Leu Ser Glu Ser Asn Leu Asn Asp Leu Arg Thr Leu Leu Asn Val Val
            195                 200                 205

Pro Gly Gln Ile Asp Tyr Ile Leu Asp Gln Phe Thr Leu Pro Lys Glu
        210                 215                 220

Lys Ala Phe Asp Asp Leu Asp Asn Ile Asn Leu Leu Val Gly Gly Ser
225                 230                 235                 240

Ile Tyr Glu Arg Leu Lys Pro Lys Val Leu Pro Val Leu Lys Asp Ile
                245                 250                 255

Lys Asp Leu Ala Glu Asp Gly Lys Gly Phe Phe Pro Pro Leu Val Ser
            260                 265                 270

Pro Val Gly Ala Ser Val Leu Lys Gln Ala Val Phe Leu Thr Asp Met
            275                 280                 285

Lys Thr Asn Arg Asp Thr Leu Val Arg Met Asn Thr Val Leu Thr Asp
        290                 295                 300

Met Lys Gln Ser Ser Ala Gln Leu Arg Thr Ser Leu Arg Asp Val Lys
305                 310                 315                 320

Thr Asn Met Glu Gln Thr Leu Met Asp Pro Gln Cys Ser Ser Pro Ala
                325                 330                 335

Ala Ala Pro Thr Cys Asp Ser Ile Arg Lys Ser Leu Ser Val Leu Asp
            340                 345                 350

Gly Ser Ala Asn Phe Asp His Leu Pro Ser Leu Asp Gly His Ile Thr
            355                 360                 365
```

```
Gln Leu Asp Gly Leu Leu Gln Thr Asp Leu Ser Gly Leu Val Gln Lys
    370                 375                 380

Ala Asn Glu Ser Leu Ser Asn Ile Pro Glu Glu Val Gln Asn Gln Thr
385                 390                 395                 400

Arg Asp Phe Ile Ser Glu Phe Lys Lys Thr Leu Asn Ser Leu Gln Ser
                405                 410                 415

Asp Val Lys Asn Ile Ser Thr Lys Ile Pro Ile Gln Lys Thr Leu Ser
                420                 425                 430

Asn Phe Val Arg Tyr Ile Asn Asp Ser Glu Asp Tyr Ile Leu Gln Tyr
            435                 440                 445

Leu Pro Thr Met Glu Glu Cys Asp Ser Tyr Arg Trp Leu Val Cys Leu
450                 455                 460

Val Ile Cys Cys Leu Leu Thr Leu Ile Leu Ile Phe Tyr Leu Leu Gly
465                 470                 475                 480

Leu Leu Cys Gly Thr Leu Gly Tyr Asp Gln Lys Ala Thr Pro Thr Arg
                485                 490                 495

Arg Gly Cys Val Ser Asn Thr Gly Leu Leu Leu Met Val Gly Val
            500                 505                 510

Gly Leu Ser Phe Phe Ser Trp Ile Ile Met Thr Ile Val Val Leu
            515                 520                 525

Thr Phe Val Thr Gly Gly Asn Met Glu Lys Leu Val Cys Glu Pro Tyr
530                 535                 540

Arg Asn Lys Lys Leu Phe Gln Val Leu Asp Thr Pro Tyr Leu Leu Asn
545                 550                 555                 560

Glu Asp Trp Lys Tyr Tyr Leu Ser Gly Leu Val Phe Asn Lys Pro Asp
                565                 570                 575

Ile Asn Leu Thr Phe Glu Gln Val Tyr Ser Asp Cys Lys Glu Asn Lys
            580                 585                 590

Gly Leu Tyr Ala Thr Leu Lys Leu Asp His Ile Tyr Asn Val Ser Glu
            595                 600                 605

Gln Leu Asn Ile Thr Lys His Thr Gly Asp Ile Asn Ser Asn Leu Glu
    610                 615                 620

Asn Met Asn Ile Arg Ile Glu Asp Ile Glu Leu Leu Asp Lys Thr Gly
625                 630                 635                 640

Met Lys Thr Leu Met Asp Leu Arg Ser Ser Gly Ile Asp Asp Ile Asp
                645                 650                 655

Tyr Ala Ala Tyr Leu Asn Ala Thr Glu Arg Ser Pro Thr Arg Val Asn
                660                 665                 670

Leu Ile Ser Phe Ala Asn Asn Leu Arg Arg Lys Ala Asn Gln Leu Pro
            675                 680                 685

Ser Gly Asn Leu Lys Thr Ser Leu Lys Ser His Thr Asp Thr Leu Thr
    690                 695                 700

Asn Ile His Glu Asn Gln Val Val Pro Leu Gln Asn Ser Met Asn Ala
705                 710                 715                 720

Met His Gln Gln Met Lys Gly Leu Gln Tyr Arg Thr Ser Gly Leu Lys
                725                 730                 735

Val Arg Val Ser Thr Thr Ile Phe Phe Leu Asn Ser Thr Gln Asp Phe
                740                 745                 750

Leu Thr Ser Gln Leu Ser Glu Val Val Glu Glu Ser Lys Gln Phe
            755                 760                 765

Gly Asn Lys Ile Ile Ser Tyr Phe Glu Arg Tyr Leu Gln Trp Val Glu
    770                 775                 780

Met Ala Ile Thr Gln Gln Phe Ala Ala Cys Arg Pro Val Ala Thr Ala
```

-continued

```
785                 790                 795                 800
Leu Asp Ser Ala Val Asn Val Phe Leu Cys Ser Tyr Ile Val Asp Pro
                805                 810                 815

Leu Asn Leu Phe Trp Phe Gly Val Gly Lys Ala Thr Ile Leu Leu Leu
            820                 825                 830

Pro Ala Val Ile Phe Ala Val Lys Leu Ala Lys Tyr Phe Arg Arg Met
            835                 840                 845

Tyr Ser Glu Asp Val Tyr Glu Asp Glu Pro Val Asn Lys Val Gln Ser
        850                 855                 860

Lys Pro Arg Ala Gln Thr Val Pro Arg Val Gln Thr Val Pro Met Val
865                 870                 875                 880

Gln Thr Val Pro Met Thr Lys Ala Leu
                885
```